(12) United States Patent
Wanders et al.

(10) Patent No.: US 10,345,217 B2
(45) Date of Patent: Jul. 9, 2019

(54) FLOWCELL SYSTEMS AND METHODS FOR PARTICLE ANALYSIS IN BLOOD SAMPLES

(71) Applicant: Iris International, Inc., Chatsworth, CA (US)

(72) Inventors: Bart J. Wanders, Trabuco Canyon, CA (US); Thomas H. Adams, Encinitas, CA (US); Gregory A. Farrell, Ridgewood, NJ (US); Warren Groner, Somers, NY (US); Xiaodong Zhao, San Diego, CA (US)

(73) Assignee: Iris International, Inc., Chatsworth, CA (US)

( * ) Notice: Subject to any disclaimer, the term of this patent is extended or adjusted under 35 U.S.C. 154(b) by 0 days.

(21) Appl. No.: 15/880,328

(22) Filed: Jan. 25, 2018

(65) Prior Publication Data

US 2018/0149576 A1    May 31, 2018

Related U.S. Application Data

(63) Continuation of application No. 15/047,971, filed on Feb. 19, 2016, now Pat. No. 9,909,973, which is a
(Continued)

(51) Int. Cl.
*G01N 35/08* (2006.01)
*G01N 33/00* (2006.01)
(Continued)

(52) U.S. Cl.
CPC ............ *G01N 15/1404* (2013.01); *G01N 1/30* (2013.01); *G01N 15/147* (2013.01);
(Continued)

(58) Field of Classification Search
CPC ............ G01N 15/1404; G01N 15/147; G01N 2015/0065; G01N 2015/1452;
(Continued)

(56) References Cited

U.S. PATENT DOCUMENTS 3,822,095 A    7/1974   Hirschfield
4,338,024 A    7/1982   Bolz et al.
(Continued)

FOREIGN PATENT DOCUMENTS

CA      2349995 A1     12/2001
CN      1265195 A       8/2000
(Continued)

OTHER PUBLICATIONS

Anonymous, "Coulter VCS Reticulocyte method", Internet Citation, Oct. 25, 1996, pp. 1-2, retrieved from: www.cyto.purdue.edu-cdroms-cyto2-6-coulter-ss000126.html.
(Continued)

*Primary Examiner* — Dean Kwak
(74) *Attorney, Agent, or Firm* — Kilpatrick Townsend & Stockton LLP

(57) ABSTRACT

The present disclosure relates to apparatus, systems, compositions, and methods for analyzing a sample containing particles. In some aspects the system comprises an analyzer which may be a visual analyzer. In one aspect, this disclosure relates to a particle imaging system comprising a flowcell through which a sample containing particles is caused to flow, and a high optical resolution imaging device which captures images for image analysis of samples. Other compositions, methods and features of this disclosure are disclosed herein.

18 Claims, 26 Drawing Sheets

Related U.S. Application Data continuation of application No. 14/216,533, filed on Mar. 17, 2014, now Pat. No. 9,322,752.

(60) Provisional application No. 61/799,152, filed on Mar. 15, 2013.

(51) Int. Cl.

| | | |
|---|---|---|
| *G01N 31/00* | (2006.01) | |
| *G01N 15/14* | (2006.01) | |
| *G01N 33/50* | (2006.01) | |
| *G01N 33/80* | (2006.01) | |
| *G01N 1/30* | (2006.01) | |
| *G01N 21/53* | (2006.01) | |
| *G01N 33/49* | (2006.01) | |
| G01N 15/00 | (2006.01) | |
| G01N 15/10 | (2006.01) | |
| G01N 21/05 | (2006.01) | |

(52) U.S. Cl.
CPC ..... *G01N 15/1434* (2013.01); *G01N 15/1463* (2013.01); *G01N 15/1468* (2013.01); *G01N 15/1475* (2013.01); *G01N 21/53* (2013.01); *G01N 33/49* (2013.01); *G01N 33/4915* (2013.01); *G01N 33/5091* (2013.01); *G01N 33/5094* (2013.01); *G01N 33/80* (2013.01); G01N 2015/0065 (2013.01); G01N 2015/1037 (2013.01); G01N 2015/1411 (2013.01); G01N 2015/1413 (2013.01); G01N 2015/1452 (2013.01); G01N 2015/1486 (2013.01); G01N 2021/058 (2013.01)

(58) Field of Classification Search
CPC ........... G01N 15/1434; G01N 15/1463; G01N 15/1475; G01N 2015/1037; G01N 2015/1411; G01N 2015/1413; G01N 2015/1486; G01N 33/5094; G01N 2021/058
USPC .............................................. 422/73; 436/10
See application file for complete search history.

(56) References Cited

U.S. PATENT DOCUMENTS

| | | | |
|---|---|---|---|
| 4,428,669 A | 1/1984 | Bessis | |
| 4,732,479 A | 3/1988 | Tanaka et al. | |
| 5,159,403 A | 10/1992 | Kosaka | |
| 5,308,526 A | 5/1994 | Dias | |
| 5,436,978 A | 7/1995 | Kasdan | |
| 5,457,526 A | 10/1995 | Kosaka | |
| 5,585,246 A | 12/1996 | Dubrow | |
| 5,633,503 A | 5/1997 | Kosaka | |
| 5,812,419 A * | 9/1998 | Chupp | G01N 35/1004 702/20 |
| 5,822,447 A | 10/1998 | Kasdan | |
| 5,880,835 A | 3/1999 | Yamazaki et al. | |
| 5,889,881 A | 3/1999 | MacAulay | |
| 6,184,976 B1 | 2/2001 | Park et al. | |
| 6,184,978 B1 | 2/2001 | Kasdan et al. | |
| 6,424,415 B1 | 7/2002 | Kasdan et al. | |
| 6,441,894 B1 | 8/2002 | Manian et al. | |
| 6,590,646 B2 | 7/2003 | Kasdan et al. | |
| 6,632,676 B1 | 10/2003 | Crews et al. | |
| 6,825,926 B2 | 11/2004 | Turner et al. | |
| 7,822,276 B2 | 10/2010 | Turner et al. | |
| 7,824,916 B2 | 11/2010 | Fujimoto | |
| 8,445,284 B2 | 5/2013 | Lapen et al. | |
| 8,564,776 B2 | 10/2013 | Graves | |
| 9,276,349 B2 | 3/2016 | Yoshida et al. | |
| 9,279,750 B2 | 3/2016 | Cremins | |
| 9,316,653 B2 | 4/2016 | Farrell et al. | |
| 9,857,361 B2 | 1/2018 | Wanders et al. | |
| 2002/0028471 A1 | 3/2002 | Oberhardt | |
| 2004/0070757 A1 | 4/2004 | Moore | |
| 2004/0180444 A1 | 9/2004 | Rannikko et al. | |
| 2005/0106739 A1* | 5/2005 | Cabuz | G01N 15/1404 436/63 |
| 2006/0148028 A1 | 7/2006 | Noda et al. | |
| 2007/0020721 A1 | 1/2007 | Yoshida | |
| 2007/0111276 A1 | 5/2007 | Lefevre et al. | |
| 2008/0019584 A1 | 1/2008 | Lindberg et al. | |
| 2008/0138852 A1 | 6/2008 | Winkelman et al. | |
| 2008/0283722 A1 | 11/2008 | Uchiyama et al. | |
| 2009/0011430 A1 | 1/2009 | Ateya et al. | |
| 2009/0158823 A1 | 6/2009 | Kaduchak et al. | |
| 2009/0178716 A1 | 7/2009 | Kaduchak et al. | |
| 2009/0269799 A1 | 10/2009 | Winkelman et al. | |
| 2009/0325217 A1 | 12/2009 | Luscher | |
| 2010/0000325 A1 | 1/2010 | Kaduchak | |
| 2010/0178666 A1 | 7/2010 | Leshansky et al. | |
| 2010/0284602 A1 | 11/2010 | Winkelman et al. | |
| 2011/0014645 A1 | 1/2011 | Winkelman et al. | |
| 2011/0070606 A1 | 3/2011 | Winkelman et al. | |
| 2011/0076712 A1* | 3/2011 | Gilligan | G01N 15/1404 435/29 |
| 2011/0128545 A1 | 6/2011 | Cox | |
| 2012/0035061 A1 | 2/2012 | Bransky | |
| 2012/0092667 A1* | 4/2012 | Tsukii | G01N 15/1434 356/338 |
| 2012/0103112 A1 | 5/2012 | Vrane et al. | |
| 2012/0301883 A1 | 11/2012 | Pagano et al. | |
| 2012/0322099 A1 | 12/2012 | Lapen et al. | |
| 2013/0070249 A1 | 3/2013 | Choi et al. | |
| 2014/0113324 A1 | 4/2014 | Di Carlo | |
| 2014/0273068 A1 | 9/2014 | Wanders et al. | |
| 2014/0273076 A1 | 9/2014 | Adams et al. | |

FOREIGN PATENT DOCUMENTS

| | | |
|---|---|---|
| CN | 1739018 A | 2/2006 |
| EP | 0 286 088 A2 | 10/1988 |
| EP | 0 468 100 A1 | 1/1992 |
| EP | 0 486 747 A2 | 5/1992 |
| EP | 0 556 971 A2 | 8/1993 |
| EP | 0 656 540 A2 | 6/1995 |
| EP | 1264205 A2 | 12/2002 |
| EP | 1761817 A1 | 3/2007 |
| EP | 2028264 A1 | 2/2009 |
| EP | 2030062 A1 | 3/2009 |
| GB | 1 557 691 A | 12/1979 |
| GB | 2121976 A | 1/1984 |
| GB | 1 471 976 A | 4/1997 |
| JP | 2003-005088 A | 1/2003 |
| WO | 99-05504 A2 | 2/1999 |
| WO | 00-11449 A1 | 3/2000 |
| WO | 01-48455 A2 | 7/2001 |
| WO | 2014/146051 A1 | 9/2014 |
| WO | 2014145983 A1 | 9/2014 |
| WO | 2014145989 A1 | 9/2014 |
| WO | 2014/146063 A9 | 11/2014 |

OTHER PUBLICATIONS

Bain, Barbara J. "Blood Cells, A Practical Guide", Blackwell Publishing, 4th Editions, 2007, ISBN-10:1-4051-4265-0, pp. 34-36.
Cubaud, et al. "High-viscosity fluid threads in weakly diffusive microfluidic systems," New Journal of Physics, Institute of Physics Publishing, vol. 11 No. 7. Jul. 31, 2009. 14 pages.
Harned, et al. 1946, vol. 68:966-967.
Kachel et al, Uniform Lateral Orientation, Cause by Flow Forces, of Flat Particles in Flow-Through Systems, Journal of Histochemistry and Cytochemistry, Jan. 1, 1977, pp. 774-780, vol. 25, No. 7, Histochemical Society, New York, NY, US.
Wietzorrek, et al. "A New Multiparameter Flow Cytometer: Optical and Electrical Cell Analysis in Combination With Video Microscopy in Flow", Apr. 1, 1999 retrieved from: http:onlinelibrary,wiley.com-store , 11 pages.
Wu et al. Biomedical Microdevices, 2005, 7(1 ):13-20.

(56) References Cited

OTHER PUBLICATIONS

Zhigang, et al. "Rapid Mixing Using Two-Phase Hydraulic Focusing in Microchannels," Biomedical Microdevices, Kluwer Academic Publishers, BO. vol. 7, No. 1. Mar. 1, 2005. 15 pages.
International Search Report and Written Opinion for Application No. PCT-US2014-030942 dated Oct. 14, 2014, all pages.
International Preliminary Report on Patentability for Application No. PCT-US2014-030942 dated Sep. 24, 2015, all pages.
International Search Report and Written Opinion of PCT-US2014-030850 dated Jun. 27, 2014, 22 pages.
International Preliminary Report on Patentability of PCT-US2014-030850 dated Sep. 24, 2015, all pages.
International Search Report and Written Opinion of PCT-US2014-030851 dated Jul. 16, 2014, all pages.
International Preliminary Report on Patentability of PCT-US2014-030851 dated Sep. 24, 2015, all pages.
International Preliminary Report on Patentability of PCT-US2014-030928 dated Sep. 24, 2015, all pages.
International Search Report and Written Opinion of PCT-US2014-030928 dated Jun. 18, 2014, all pages.
Office Action for JP Application No. 2016-502584 dated Jan. 9, 2018, 14 pages.

\* cited by examiner

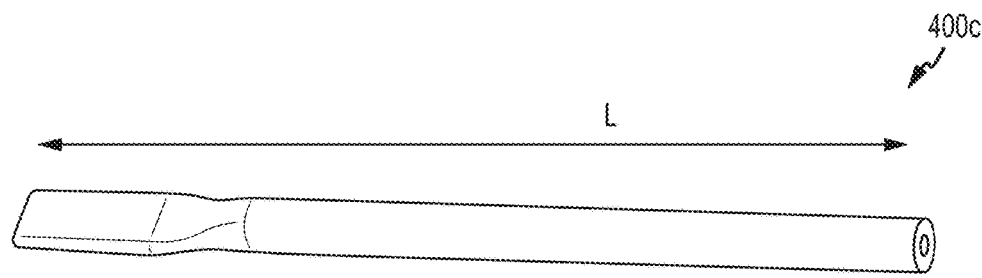
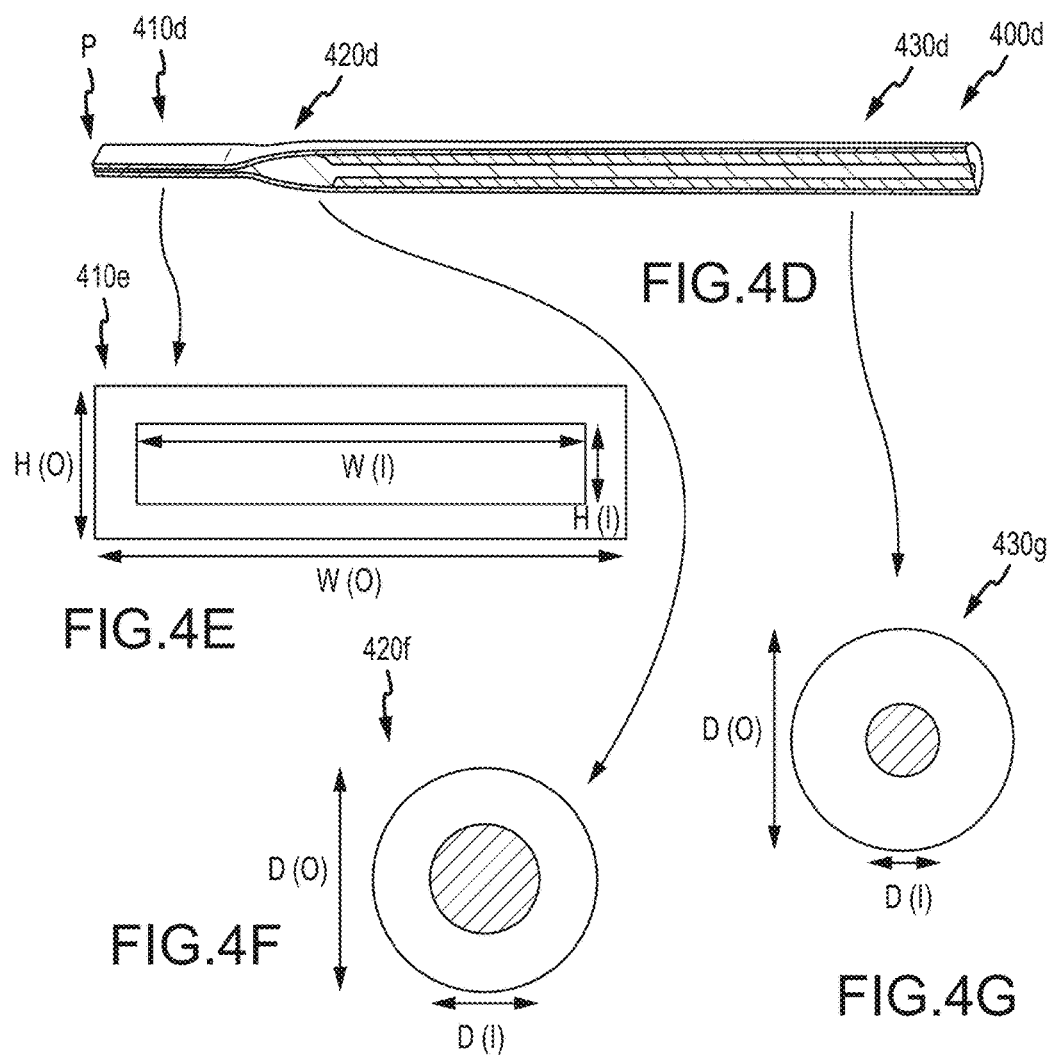

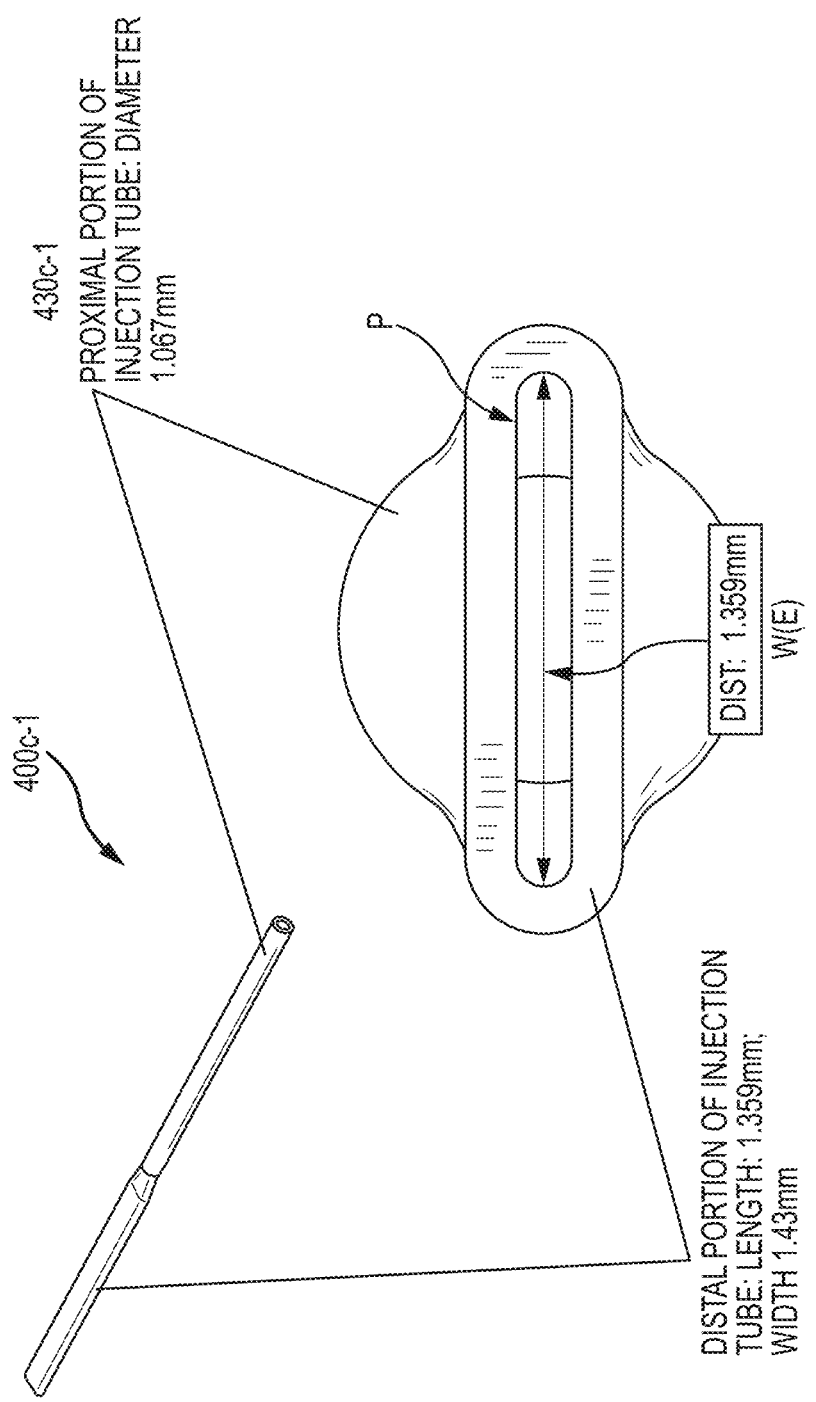

RBCs IN SAMPLE STREAM
WITH CONVENTIONAL SHEATH

RBCs IN SAMPLE STREAM
WITH PIOAL

RBCs IN SAMPLE STREAM AT 20X
MAGNIFICATION WITH CONVENTIONAL SHEATH

RBCs IN SAMPLE STREAM AT 20X
MAGNIFICATION WITH PIOAL

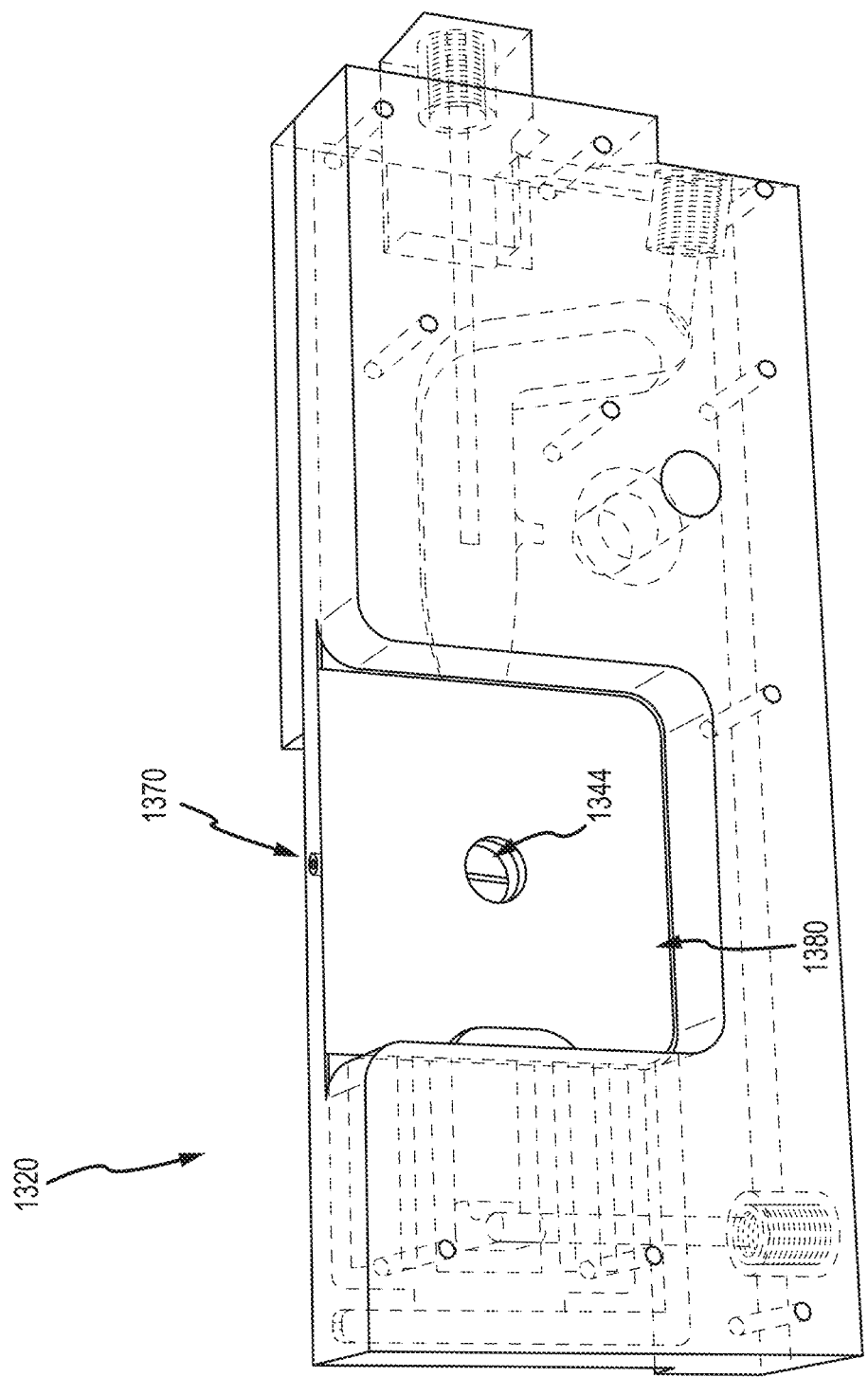

FLOWCELL SYSTEMS AND METHODS FOR PARTICLE ANALYSIS IN BLOOD SAMPLES

CROSS-REFERENCES TO RELATED APPLICATIONS

This application is a continuation of U.S. patent application Ser. No. 15/047,971, filed Feb. 19, 2016, entitled "FLOWCELL SYSTEMS AND METHODS FOR PARTICLE ANALYSIS IN BLOOD SAMPLES," which is a continuation of U.S. patent application Ser. No. 14/216,533, filed Mar. 17, 2014, entitled "FLOWCELL SYSTEMS AND METHODS FOR PARTICLE ANALYSIS IN BLOOD SAMPLES," (now U.S. Pat. No. 9,322,752, issued Apr. 26, 2016), which is a nonprovisional of and claims the benefit of priority to U.S. Provisional Patent Application No. 61/799,152, filed Mar. 15, 2013, entitled "ANALYSIS OF PARTICLES IN FLUID SAMPLES," the entire contents of each of which is herein incorporated by reference in its entirety. This application is also related to U.S. patent application Ser. Nos. 14/215,834, 14/216,811, 14/217,034, and 14/216,339 and International Patent Application Nos. PCT/US14/30928, PCT/US14/30850, and PCT/US14/30851, all filed Mar. 17, 2014. The content of each of these filings is incorporated herein by reference.

BACKGROUND OF THE INVENTION

This disclosure relates to the field of apparatus, systems, compositions, and methods for analysis of particles, including imaging of particles in fluid samples, using wholly or partly automated devices to discriminate and quantify particles such as blood cells in the sample. The present disclosure also relates to a particle and/or intracellular organelle alignment liquid (PIOAL) useful for analyzing particles in a sample from a subject, methods for producing the liquid, and methods for using the liquid to detect and analyze particles. Compositions, systems, devices and methods useful for conducting image-based biological fluid sample analysis are also disclosed. The compositions, systems, devices, and methods of the present disclosure are also useful for detecting, counting and characterizing particles in biological fluids such as red blood cells, reticulocytes, nucleated red blood cells, platelets, and for image and morphologically-based white blood cell differential counting, categorization, sub-categorization, characterization and/or analysis.

Blood cell analysis is one of the most commonly performed medical tests for providing an overview of a patient's health status. A blood sample can be drawn from a patient's body and stored in a test tube containing an anticoagulant to prevent clotting. A whole blood sample normally comprises three major classes of blood cells including red blood cells (erythrocytes), white blood cells (leukocytes) and platelets (thrombocytes). Each class can be further divided into subclasses of members. For example, five major types or subclasses of white blood cells (WBCs) have different shapes and functions. White blood cells may include neutrophils, lymphocytes, monocytes, eosinophils, and basophils. There are also subclasses of the red blood cell types. The appearances of particles in a sample may differ according to pathological conditions, cell maturity and other causes. Red blood cell subclasses may include reticulocytes and nucleated red blood cells.

A blood cell count estimating the concentration of RBCs, WBCs or platelets can be done manually or using an automatic analyzer. When blood cell counts are done manually, a drop of blood is applied to a microscope slide as a thin smear. Traditionally, manual examination of a dried, stained smear of blood on a microscope slide has been used to determine the number or relative amounts of the five types of white blood cells. Histological dyes and stains have been used to stain cells or cellular structures. For example, Wright's stain is a histologic stain that has been used to stain blood smears for examination under a light microscope. A Complete Blood Count (CBC) can be obtained using an automated analyzer, one type of which counts the number of different particles or cells in a blood sample based on impedance or dynamic light scattering as the particles or cells pass through a sensing area along a small tube. The automated CBC can employ instruments or methods to differentiate between different types of cells that include RBCs, WBCs and platelets (PLTs), which can be counted separately. For example, a counting technique requiring a minimum particle size or volume might be used to count only large cells. Certain cells such as abnormal cells in the blood may not be counted or identified correctly. Small cells that adhere to one another may be erroneously counted as a large cell. When erroneous counts are suspected, manual review of the instrument's results may be required to verify and identify cells.

Automated blood cell counting techniques can involve flow cytometry. Flow cytometry involves providing a narrow flow path, and sensing and counting the passage of individual blood cells. Flow cytometry methods have been used to detect particles suspended in a fluid, such as cells in a blood sample, and to analyze the particles as to particle type, dimension, and volume distribution so as to infer the concentration of the respective particle type or particle volume in the blood sample. Examples of suitable methods for analyzing particles suspended in a fluid include sedimentation, microscopic characterization, counting based on impedance, and dynamic light scattering. These tools are subject to testing errors. On the other hand, accurate characterization of types and concentration of particles may be critical in applications such as medical diagnosis.

In counting techniques based on imaging, pixel data images of a prepared sample that may be passing through a viewing area are captured using a microscopy objective lens coupled to a digital camera. The pixel image data can be analyzed using data processing techniques, and also displayed on a monitor.

Aspects of automated diagnosis systems with flowcells are disclosed in U.S. Pat. No. 6,825,926 to Turner et al. and in U.S. Pat. Nos. 6,184,978; 6,424,415; and 6,590,646, all to Kasdan et al., which are hereby incorporated by reference as if set forth fully herein.

Automated systems using dynamic light scattering or impedance have been used to obtain a complete blood count (CBC): total white blood cell count (WBC), total cellular volume of red blood cells (RBC distribution), hemoglobin HGB (the amount of hemoglobin in the blood); mean cell volume (MCV) (mean volume of the red cells); MPV (mean PLT volume); hematocrit (HCT); MCH (HGB/RBC) (the average amount of hemoglobin per red blood cell); and MCHC (HGB/HCT) (the average concentration of hemoglobin in the cells). Automated or partially automated processes have been used to facilitate white blood cell five part differential counting and blood sample analyses.

Although such currently known particle analysis systems and methods, along with related medical diagnostic techniques, can provide real benefits to doctors, clinicians, and patients, still further improvements are desirable. Embodiments of the present invention provide solutions for at least some of these outstanding needs.

BRIEF SUMMARY OF THE INVENTION

Embodiments of the present invention relate to apparatus, systems, compositions, and methods for analyzing a prepared sample containing particles. In some aspects the system comprises an analyzer which may be a visual analyzer. In some aspects, the apparatus contains a visual analyzer and a processor. In one aspect, this disclosure relates to an automated particle imaging system in which a liquid sample containing particles of interest is caused to flow through a flowcell having a viewport through which a high optical resolution imaging device captures an image. In some aspects the high optical resolution imaging device comprises a camera such as a digital camera. In one aspect the high optical resolution imaging device comprises an objective lens.

The flowcell is coupled to a source of sample fluid, such as a prepared sample, and to a source of particle and/or intracellular organelle alignment liquid (PIOAL). The system permits capture of focused images of particles in a sample in flow. In some embodiments the images can be used in automated, high throughput processes for categorizing and subcategorizing particles. An exemplary visual analyzer may include a processor to facilitate automated analysis of the images. In some cases, the visual analyzer can be used in methods of this disclosure to provide automated image-based WBC differential counting or other blood sample particle analysis protocols. In some cases, the methods of this disclosure relate to automated identification of morphological abnormalities for determining, diagnosing, prognosing, predicting, and/or supporting a diagnosis of whether a subject is healthy or has a disease, condition, abnormality and/or infection and for monitoring whether a subject is responsive or non-responsive to treatment.

In one aspect, embodiments of the present invention encompass methods for imaging particles using a particle analysis system that is configured for combined viscosity and geometric hydrofocusing. The particles can be included within first and second sample fluids of a blood fluid sample. Exemplary methods may include flowing a sheath fluid along a flowpath of a flowcell of the particle analyzer, and the sheath fluid can have a viscosity that is different from a viscosity of the blood fluid sample. In some cases, the sheath fluid has a sheath fluid viscosity that differs from the sample fluid viscosity by a viscosity difference, and the viscosity difference has a value in a predetermined viscosity difference range. Methods may also include injecting the first sample fluid from a sample fluid injection tube into the flowing sheath fluid within the flowcell so as to provide a sample fluid stream having a first thickness adjacent the injection tube. The flowpath of the flowcell can have a decrease in flowpath size such that thickness of the sample fluid stream decreases from the initial thickness to a second thickness adjacent an image capture site. Methods can further include imaging a first plurality of the particles from the first sample fluid at the image capture site of the flowcell, and initiating sample fluid transients by terminating injection of the first sample fluid into the flowing sheath fluid and injecting the second sample fluid into the flowing sheath fluid. What is more, methods can include imaging a second plurality of the particles from the second sample fluid at the image capture site of the flowcell. The imaging of the second plurality of particles can be performed substantially after the sample fluid transients and within 4 seconds of the imaging of the first plurality the particles. In some cases, the decrease in flowpath size is defined by a proximal flowpath portion having a proximal thickness, and distal flowpath portion having a distal thickness less than the proximal thickness. A downstream end of the sample fluid injection tube can be positioned distal to the proximal flowpath portion. The viscosity difference between the sheath and blood fluid samples, in combination with the decrease in flowpath size, can be effective to hydrofocus the first and second sample fluids at the image capture site, while a viscosity agent in the sheath fluid retains viability of cells in the first and second sample fluids leaving structure and content of the cells intact when the cells extend from the sample fluid stream into the flowing sheath fluid.

In some methods, the injection tube can include an internal volume based on a ratio of a flow area cross-section of the injection tube to a flow area cross-section of the flowcell, a ratio of the flow area cross-section of the injection tube to an outer diameter of the flowcell, or a ratio of the flow area cross-section of the injection tube to a flow area cross-section of the sample stream. In some cases, the decrease in flowpath size can be defined by opposed walls of the flowpath angling radially inwardly along the flowpath generally symmetric about a transverse plane that bisects the sample fluid stream first and second thicknesses. In some cases, symmetry in the decrease in flowpath size is effective to limit red blood cells imaging orientation misalignment in the blood fluid sample to less than about 20%. In some cases, the blood fluid sample includes spherical particles, and a viscosity differential between the sample fluid and the sheath fluid is effective to align intracellular organelles of the spherical particles within a focal plane at the image capture site of the flowcell. In some cases, a distal portion of the sample fluid injection tube is positioned at an axial separation distance from the image capture site, and the axial separation distance has a value within a range from about 16 mm to about 26 mm. In some cases, the injection tube has an internal volume of less than about 30 µL.

In some methods, the injection tube has a proximal portion having a first flow cross-section area and a distal portion having a second flow cross-section area, and the flow cross-section area of the proximal portion is greater than 1.5 times the flow cross-section area of the distal portion. In some methods, the injection tube has a central portion disposed between the proximal portion and the distal portion, the central portion has a third flow cross-section, and the third flow cross section is greater than the first and second flow cross-sections.

In some methods, a distal portion of the sample fluid injection tube includes an outlet port having a height and a width, and the height can be less than the width. In some cases, the height is about 150 µm and the width is about 1350 µm. In some cases, the height has a value within a range from about 50 µm to about 250 µm and the width has a value within a range from about 500 µm to about 3000 µm.

In some methods, a ratio of the sheath fluid flow rate to the sample fluid flow rate is about 70. In some cases, the ratio of the sheath fluid flow rate to the sample fluid flow rate is about 200. In some cases, the sheath fluid has a flow rate of about 35 µL/s and the sample fluid has a flow rate of about 0.5 µL/s. In some cases, the sample fluid has a velocity of between about 20 and 200 mm/second at the image capture site. In some cases, the sheath fluid velocity and the fluid sample velocity may differ at a flowpath position near the injection tube tube exit port, and the sheath fluid velocity and the fluid sample velocity may be the same at the image capture site. In some cases, the first thickness of the sample fluid stream is about 150 µm, for example where the sample fluid exits the injection tube. In some cases, the second thickness of the sample fluid stream is within a range from about 2 µm to about 10 µm, for example where the sample fluid stream flows through the image capture site. In some cases, the second thickness of the sample fluid stream is within a range from about 2 µm to about 4 µm. In some cases, a ratio of the first thickness of the sample fluid stream to the second thickness of the sample fluid stream has a value within a range from about 20:1 to about 70:1. In some cases, a ratio of the first thickness of the sample fluid stream to the second thickness of the sample fluid stream has a value within a range from about 5:1 to about 200:1. In some cases, a ratio of the proximal thickness of the proximal flowpath portion to the distal thickness of the distal flowpath portion has a geometric thinning value selected from the group consisting of 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 125:1, 130:1, 140:1, 150:1, 160:1, 170:1, 180:1, 190:1, and 200:1. In some cases, the flowcell has a minimum compression ratio of about 50:1 and a maximum compression ratio of about 125:1.

In some methods, the flowcell is oriented so that the sample fluid and the sheath fluid flowing within the flowcell flow against gravity. In some cases, the flowcell is oriented so that the sample fluid and the sheath fluid flowing within the flowcell flow with gravity. Exemplary methods may also include removing bubbles from the flowing sample fluid. In some cases, the first sample fluid reaches a stabilized state within about 1 to 3 seconds following injection of the first sample fluid from the sample fluid injection tube into the flowing sheath fluid. In some cases, the first sample fluid reaches a stabilized state within less than 1 second following injection of the first sample fluid from the sample fluid injection tube into the flowing sheath fluid. In some cases, the first sample fluid reaches a stabilized state within about 1.8 seconds from injection of the first sample fluid from the sample fluid injection tube into the flowing sheath fluid. In some cases, the sample fluid has a transit time through the flowcell within a range from about 1 to 4 seconds. In some cases, the sample fluid has a transit time through the flowcell within a range from about 2 to 4 seconds. In some cases, the image capture site has a field of view of between about 150 µm×150 µm and 400 µm×400 µm. In some cases, the first sample fluid has a volume in a range from about 50 to about 150 µL. In some cases, a proximal portion of the injection tube is coupled to a sample port of a sample inlet fitting.

In another aspect, embodiments of the present invention encompass particle analysis systems that perform combined viscosity and geometric hydrofocusing for imaging particles in a blood fluid sample. The particles can be included within first and second sample fluids. Exemplary systems can include a flowcell having a flowpath configured for transmitting a flow of the sheath fluid. The sheath fluid can have a viscosity that is different from a viscosity of the blood fluid sample. In some cases the sheath fluid viscosity is greater than the blood fluid sample viscosity. In some cases, the sheath fluid has a sheath fluid viscosity that differs from the sample fluid viscosity by a viscosity difference, and the viscosity difference has a value in a predetermined viscosity difference range. Systems may also include a sample fluid injection system in fluid communication with the flowpath. The sample fluid injection system can be configured for injecting the sample fluids into the flowing sheath fluid within the flowcell so as to provide a sample fluid stream having a first thickness adjacent the injection tube. The flowpath of the flowcell can have a decrease in flowpath size such that thickness of the sample fluid stream decreases from the initial thickness to a second thickness adjacent an image capture site. Further, systems can include an image capture device aligned with the image capture site so as to image a first plurality of the particles from the first sample fluid at the image capture site of the flowcell. What is more, systems can include a processor coupled with the sample fluid injector system and the image capture device. The processor can be configured to terminate injection of the first sample fluid into the flowing sheath fluid and injecting the second sample fluid into the flowing sheath fluid such that sample fluid transients are initiated, and to image a second plurality of the particles from the second sample fluid at the image capture site of the flowcell after the sample fluid transients and within 4 seconds of the imaging of the first plurality the particles. In exemplary systems, the viscosity difference between the sheath and blood fluid samples, in combination with the decrease in flowpath size, is effective to hydrofocus the first and second sample fluids at the image capture site of the flowcell, while a viscosity agent in the sheath fluid retains viability of cells in the first and second sample fluids leaving structure and content of the cells intact when the cells extend from the sample fluid stream into the flowing sheath fluid.

In some systems, the injection tube includes an internal volume based on a ratio of a flow area cross-section of the injection tube to a flow area cross-section of the flowcell, a ratio of the flow area cross-section of the injection tube to an outer diameter of the flowcell, or a ratio of the flow area cross-section of the injection tube to a flow area cross-section of the sample stream. In some cases, the decrease in flowpath size is defined by opposed walls of the flowpath angling radially inwardly along the flowpath generally symmetric about a transverse plane that bisects the sample fluid stream first and second thicknesses. In some cases, symmetry in the decrease in flowpath size is effective to limit red blood cells imaging orientation misalignment in the blood fluid sample to less than about 20%. In some cases, a distal portion of the sample fluid injection tube is positioned at an axial separation distance from the image capture site, and the axial separation distance has a value within a range from about 16 mm to about 26 mm. In some cases, the injection tube includes a proximal portion having a first flow cross-section area and a distal portion having a second flow cross-section area, and the flow cross-section area of the proximal portion is greater than 1.5 times the flow cross-section area of the distal portion. In some cases, the sample fluid has a transit time through the flowcell within a range from about 1 to 4 seconds. In some cases, the sample fluid has a transit time through the flowcell within a range from about 2 to 4 seconds. In some cases, the flowcell is configured to receive the sheath fluid from a sheath fluid source into the flowpath in a first flow direction that is perpendicular to second flow direction of the sheath fluid along the flowpath at the imaging site. In some cases, the flowcell includes an autofocus target for the image capture device.

The above described and many other features and attendant advantages of embodiments of the present invention will become apparent and further understood by reference to the following detailed description when considered in conjunction with the accompanying drawings.

BRIEF DESCRIPTION OF THE DRAWINGS

FIGS. 4A, 4B-1, and 4B-2 depict aspects of flowcells according to embodiments of the present invention.

FIGS. 4A-1 and 4A-2 depict cross-section views of sheath fluid (e.g. PIOAL) envelope and sample fluidstream dimensions within a flowcell at a cannula exit port and an image capture site, respectively, according to embodiments of the present invention.

FIGS. 4C-4G, 4C-1, and 4D-1 depict aspects of cannula configurations according to embodiments of the present invention.

FIG. 4L-1 depicts aspects of fluid flow velocity within a flowcell according to embodiments of the present invention.

FIGS. 13A, 13B, and 13C depict aspects of flowcell temperature sensors according to embodiments of the present invention.

DETAILED DESCRIPTION OF THE INVENTION

Figure 1:
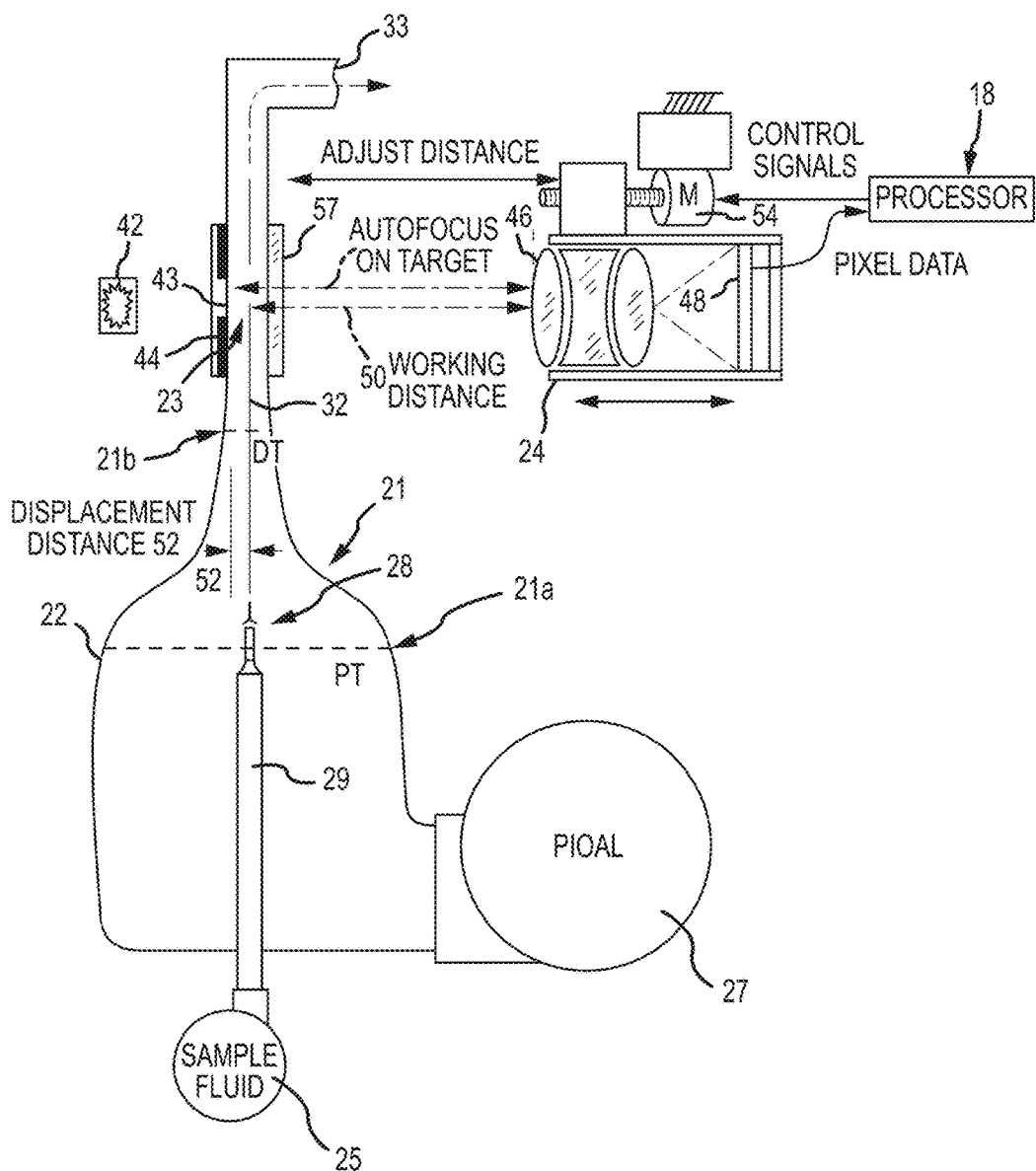
FIG. 1 is a schematic illustration, partly in section and not to scale, showing operational aspects of an exemplary flowcell, autofocus system and high optical resolution imaging device for sample image analysis using digital image processing.

The present disclosure relates to apparatus, systems, compositions, and methods for analyzing a sample containing particles. In one embodiment, the invention relates to an automated particle imaging system which comprises an analyzer which may be, for example, a visual analyzer. In some embodiments, the visual analyzer may further comprise a processor to facilitate automated analysis of the images.

According to this disclosure, a system comprising a visual analyzer is provided for obtaining images of a sample comprising particles suspended in a liquid. The system may be useful, for example, in characterizing particles in biological fluids, such as detecting and quantifying erythrocytes, reticulocytes, nucleated red blood cells, platelets, and white blood cells, including white blood cell differential counting, categorization and subcategorization and analysis. Other similar uses such as characterizing blood cells from other fluids are also contemplated.

The discrimination of blood cells in a blood sample is an exemplary application for which the subject matter is particularly well suited. The sample is prepared by automated techniques and presented to a high optical resolution imaging device as a thin ribbon-shaped sample stream to be imaged periodically while the ribbon-shaped sample stream flows across a field of view. The images of the particles (such as blood cells) can be distinguished from one another, categorized, subcategorized, and counted, using pixel image data programmed processing techniques, either exclusively automatically or with limited human assistance, to identify and count cells or particles. In addition to the cell images, which can be stored and made available in the case of unusual or critical features of particles, the output data includes a count of the occurrences of each particular category and/or subcategory of cell or particle distinguished in the recorded sample images.

The counts of the different particles found in each image can be processed further, for example used to accumulate accurate and statistically significant ratios of cells of each distinguished category and/or subcategory in the sample as a whole. The sample used for visual discrimination can be diluted, but the proportions of cells in each category and/or subcategory are represented in the diluted sample, particularly after a number of images have been processed.

The apparatus and methods disclosed herein are useful in discriminating and quantifying cells in samples based on visual distinctions. The sample can be a biological sample, for example, a body fluid sample comprising white blood cells, including without limitation, blood, serum, bone marrow, lavage fluid, effusions, exudates, cerebrospinal fluid, pleural fluid, peritoneal fluid, and amniotic fluid. In some embodiments, the sample can be a solid tissue sample, e.g., a biopsy sample that has been treated to produce a cell suspension. The sample may also be a suspension obtained from treating a fecal sample. A sample may also be a laboratory or production line sample comprising particles, such as a cell culture sample. The term sample may be used to refer to a sample obtained from a patient or laboratory or any fraction, portion or aliquot thereof. The sample can be diluted, divided into portions, or stained in some processes.

In one aspect, the systems, compositions and methods of this disclosure provide surprisingly high quality images of cells in a flow. In one aspect, the visual analyzer can be used in methods of this disclosure to provide automated image based WBC differential counting. In certain embodiments, the methods of this disclosure relate to automated identification of visual distinctions, including morphological features and/or abnormalities for determining, diagnosing, prognosing, predicting, and/or supporting a diagnosis of whether a subject is healthy or has a disease, condition, abnormality and/or infection and/or is responsive or non-responsive to treatment. The system may further comprise a particle counter in some embodiments. Applications include categorizing and/or subcategorizing, and counting cells in a fluid sample, such as a blood sample. Other similar uses for counting additional types of particles and/or particles in other fluid samples are also contemplated. The system, compositions, and methods of this invention can be used for real-time categorization and subcategorization and viewing of images using any suitable automated particle recognition algorithm. The captured images for each sample can be stored to be viewed at a later date.

In another aspect, the apparatus, compositions, and methods of this invention provide surprisingly more accurate image based cell categorization and subcategorization and flagging which reduces the manual review rate compared to the manual review rate when using current automated analyzers. The systems, compositions, and methods reduce the manual review rate and permit the manual review to be performed on the instrument. In addition, the systems, compositions, and methods of this disclosure also reduce the percentage of samples flagged during automated analysis as requiring manual review.

The present disclosure further relates to systems, methods and compositions for combining a complete blood count (CBC) counter with an analyzer, such as a visual analyzer, in order to obtain a CBC and an image based expanded white blood cell differential count and an image based expanded platelet count, thereby extending the effective detection range for counting platelets.

Accordingly, in some embodiments, the present disclosure provides an apparatus and a method for analyzing a sample containing particles, for example, blood cells. According to this disclosure, a visual analyzer is provided for obtaining images of a sample comprising particles suspended in a liquid. In some embodiments, the visual analyzer comprises a flowcell and an autofocus component, in which a liquid sample containing particles of interest is caused to flow through a flowcell having a viewport through which a camera coupled to an objective lens captures digital images of particles. The flowcell is coupled to a source of sample fluid, such as a diluted and/or treated blood sample or other bodily fluid sample as described herein, and to a source of a clear sheath fluid, or particle and/or intracellular organelle alignment liquid (PIOAL).

In one embodiment, the apparatus also comprises a particle counter having at least one detection range, as well as an analyzer, and a processor. The analyzer and the processor are configured to provide additional information to correct counting, categorization, and subcategorization errors associated with the particle counter, and further determine accurate particle count or concentration of different categories and/or subcategories of particles in the sample.

The instant disclosure provides methods and compositions useful for particle and/or intracellular organelle alignment in conducting image-based sample analysis. In some embodiments, this disclosure relates to methods and compositions for combined counting and imaging system with the ability to perform a complete blood count (CBC) and an image based expanded white blood cell (WBC) differential able to identify and count cell types, such as WBCs, RBCs, and/or platelets, including, for example, neutrophils, lymphocytes, monocytes, eosinophils, basophils, reticulocytes, nucleated RBCs, blasts, pro-myelocytes, myelocytes, or metamyelocytes, and to provide image based information for WBC counts and morphologies, red blood cell (RBC) counts and morphologies and platelet (PLT) counts and morphologies.

In other embodiments, this disclosure relates to a PIOAL that can be used in image based analysis of particles as described herein. Cell category and/or subcategory count in blood samples is used in this disclosure as nonlimiting examples of the sort of samples that may be analyzed. In some embodiments, cells present in samples may also include bacterial or fungal cells as well as white blood cells, red blood cells and/or platelets. In some embodiments, particle suspensions obtained from tissues or aspirates may be analyzed.

The discrimination of blood cells in a blood sample is an exemplary application for which the subject matter is particularly well suited. The sample is prepared by automated techniques and presented to a high optical resolution imaging device as a ribbon-shaped sample stream to be imaged periodically while the sample flows across a field of view. The images of the particles (such as blood cells) can be distinguished from one another, categorized, subcategorized, and/or counted, using pixel image data programmed processing techniques, either exclusively automatically or with limited human assistance, to identify and count cells or particles. In addition to the cell images, which can be stored and made available in the case of unusual or critical features, the output data includes a count of the occurrences of each particular category and/or subcategory of cell or particle distinguished in the recorded sample images. The counts of the different particles found in each image can be processed further, for example used to accumulate accurate and statistically significant proportionate ratios, or functions thereof of cells of each distinguished category and/or subcategory in the sample as a whole. The sample used for visual discrimination can also be highly diluted, but the proportions of cells in each category and/or subcategory are represented in the distribution for the diluted sample, particularly after a number of images have been processed.

In some aspects, samples are presented, imaged and analyzed in an automated manner. In the case of blood samples, the sample may be substantially diluted with a suitable diluent or saline solution, which reduces the extent to which the view of some cells might be hidden by other cells in an undiluted or less-diluted sample. The cells can be treated with agents that enhance the contrast of some cell aspects, for example using permeabilizing agents to render cell membranes permeable, and histological stains to adhere in and to reveal features, such as granules and the nucleus. In some embodiments it may be desirable to stain an aliquot of the sample for counting and characterizing particles which include reticulocytes, nucleated red blood cells, and platelets, and for white blood cell differential, characterization and analysis. In other embodiments, samples containing red blood cells may be diluted before introduction to the flowcell and imaging.

The particulars of sample preparation apparatus and methods for sample dilution, permeabilizing and histological staining, generally are accomplished using precision pumps and valves operated by one or more programmable controllers, and are not central to this disclosure. Examples can be found in patents assigned to International Remote Imaging Systems, Inc., such as U.S. Pat. No. 7,319,907, concerning programmable controls. Likewise, techniques for distinguishing among certain cell categories and/or subcategories by their attributes such as relative size and color can be found in U.S. Pat. No. 5,436,978 in connection with white blood cells. The disclosures of these patents are hereby incorporated by reference.

To facilitate the capacity, speed and effectiveness by which particles such as cells are categorized and/or subcategorized, it is advantageous to provide clear high quality images of the blood cells for automated analysis by the data processing system. According to the present disclosure, a prepared sample stream is arranged in a thin ribbon having a stable position between opposite walls of a flowcell. The positioning of the sample stream and its flattening into a thin ribbon shape may be achieved by flow between layers of a PIOAL introduced into the flowcell that differs in viscosity from the sample fluid and is flowed through a symmetrical flow channel.

The PIOAL has a suitable viscosity and density, and flow rates at the point of introduction to the flowcell of the sample are such that the sample fluid flattens into a thin ribbon. The ribbon-shaped sample stream is carried along with the PIOAL, to pass in front of a viewing port where an objective lens and a light source are arranged to permit viewing of the ribbon-shaped sample stream. The sample fluid is introduced, for example, injected at a point where the flowpath of the PIOAL narrows symmetrically. As a result, the sample fluid stream is flattened and stretched into a thin ribbon. A PIOAL of this disclosure may be used as the sheath fluid with any visual analyzer of this disclosure. In one embodiment, the PIOAL can be introduced into an end of the flowcell to carry along the sample fluid toward the discharge.

The dimension of the ribbon-shaped sample stream in the viewing zone is affected by geometric thinning of the PIOAL flowpath and differential linear velocity of the sample fluid and PIOAL resulting in thinning and stretching of the ribbon-shaped sample stream. The initial differential linear velocity of the sample to PIOAL may range from 0.5:1 to 5:1. The PIOAL flowpath cross section may be thinned by reducing the depth by a factor of about 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 125:1, 130:1, 140:1, 150:1, 160:1, 170:1, 180:1, 190:1, or 200:1. In one embodiment, the geometric thinning is 40:1. In one embodiment, the geometric thinning is 30:1. Factors taken into account are transit time through the flowcell, desired rate of sample throughput, achieving a ribbon-shaped sample stream thickness comparable to particle size, obtaining alignment of particles and organelles, achieving in focus content of particles, balancing pressure, flow, and viscosity within operational limits, optimizing ribbon-shaped sample stream thickness, obtaining a desired linear velocity, manufacturability considerations, and volumes of sample and PIOAL required.

The length and volume of the cannula and the cross-section flattening may be selected to reduce the period of sample flow instability, thereby increasing throughput. In some embodiments the period of flow instability may be less than about 3, 2.75, 2.5, 2.25, 2, 1.75, 1.5 1.25, or less than about 1 second. A smaller cannula volume may also reduce the time and volume of diluent needed to clean the cannula between sample runs. In some embodiments the transit time through the flowcell is 1, 2, 3, or 4 seconds, or any range in between any two of those times. In some embodiments the transit time may be less than 4, 3 or 2 seconds.

The viscosities and the flow rates of the sample fluid and the PIOAL and the contour of the flowcell are arranged such that the PIOAL flow flattens and stretches the sample flow into a flat ribbon consistently through the viewing zone at a dependable location. The sample fluid stream may be compressed to approximately 2 to 3 μm in fluid flow thickness. Several blood cell types have diameters larger than the stream thickness. Shear forces in the direction parallel to the direction of the flow cause an increase of an image projection of the particles under imaging conditions in the focal plane of the high optical resolution imaging device and/or causing the intraparticle structures, for example, intracellular structures, organelles or lobes, to be positioned, repositioned, and/or better-positioned to be substantially parallel to the direction of flow. The high optical resolution imaging device depth of field is up to 7 μm, for example, 1-4 μm.

The flow cross section of the PIOAL, with the ribbon-shaped sample stream carried along, is constant through a viewing zone in front of a viewing port through which the objective lens is directed. The objective lens may be the objective component of a high optical resolution imaging device or the digital image capture device. The ribbon-shaped sample stream follows a path across the viewing zone at a known and repeatable position within the flowcell, for example, at a known and repeatable distance from two walls of the flowcell, being discharged downstream.

Optical information from the particles in the sample are detected by a detecting section in the analyzer, when the ribbon-shaped sample stream is carried through the viewing zone in front of the viewing port, thereby generating data from the particles/cells contained in the sample. The use of this analyzer allows capture, processing, categorization and subcategorization and counting of cells and/or particles contained in samples. The PIOAL liquid can be prepared by the addition of viscosity modifying agent, buffer agent, pH adjusting agent, antimicrobial agent, ionic strength modifier, surfactant, and/or a chelating agent. Exemplary functional components and/or features of the analyzer in the present disclosure can include, for example, the ability to acquire and/or process data from image analysis, sample staining processing, image processing, and/or particle image identification, counting, and/or categorization and subcategorization.

In one embodiment this disclosure is based on the surprising and unexpected discovery that the addition of a suitable amount of a viscosity agent in the PIOAL significantly improves particle/cell alignment in a flowcell, leading to a higher percentage of in-focus cells, or cellular components, and higher quality images of cells and/or particles in flow. The addition of the viscosity agent increases the shear forces on cells like RBCs, which improves the alignment of the cells in a plane substantially parallel to the flow direction, which results in image optimization. This also results in positioning, repositioning, and/or better-positioning of intraparticle structures such as intracellular structures, organelles or lobes substantially parallel to the direction of flow, which results in image optimization. The viscosity agent also reduces misalignment of cells, generally, but not limited to cells that are smaller in diameter than the flow stream.

Alignment of cells that are smaller in diameter than the flow stream, for example, red blood cells may be obtained by for example, increasing the viscosity of the PIOAL, or by increasing the flow speed ratio. This results in alignment of the RBCs parallel to the direction of the flow and to the focal plane FP (e.g. as depicted in FIG. 4K). In some embodiments, a reduction in RBC misalignment and/or increase in RBC alignment is achieved by increasing the viscosity of the PIOAL.

The ribbon-shaped sample stream thickness can be affected by the relative viscosities and flow rates of the sample fluid and the PIOAL. The source of the sample and/or the source of the PIOAL, for example comprising precision displacement pumps, can be configured to provide the sample and/or the PIOAL at controllable flow rates for optimizing the dimensions of the ribbon-shaped sample stream, namely as a thin ribbon at least as wide as the field of view of the high optical resolution imaging device or the digital image capture device.

The flow cross section of the PIOAL, with the ribbon-shaped sample stream carried along, is constant through a viewing zone in front of a viewing port through which the high optical resolution imaging device is directed. The ribbon-shaped sample stream follows a path across the viewing zone at a known and repeatable distance from either of the front and rear walls of the flowcell, being discharged downstream of that.

The term high optical resolution imaging device can include devices that are capable of obtaining particles images with sufficient visual distinctions to differentiate morphological features and/or changes. Exemplary high optical resolution imaging devices can include devices with an optical resolution of 1 um or lower, including for example, 0.4 to 0.5 um, such as for example, 0.46 um.

In some embodiments, the images obtained in any of the compositions and/or methods of this invention may be digitized images. In some embodiments, the images obtained are microscopy images. In certain embodiments, the images may be obtained manually. In other embodiments, at least part of the procedure for obtaining the images is automated. In some embodiments, the images may be obtained using a visual analyzer comprising a flowcell, a high optical resolution imaging device or the digital image capture device, optionally with an autofocus feature.

In one embodiment, the images provide information relating to the cytosolic, cell nucleus and/or nuclear components of the cell. In one embodiment, the images provide information relating to the granular component and/or other morphological features of the cell. In one embodiment, the images provide information relating to cytosolic, nuclear and/or granular components of the cell. The granular and/or nuclear images and/or features are determinative for cell categorization and subcategorization both independently or in combination with each other.

In one aspect of the methods of this invention, the cells contacted with particle contrast agent composition and/or imaged are nucleated red blood cells. In yet another aspect, the methods of this invention relate to a method for performing image-based red blood cell categorization and sub-categorization comprising: a) imaging a portion of the red blood cells; and b) determining the morphology of the imaged red blood cells. As used herein, red blood cells (RBC) can include, for example, normal or abnormal red blood cells, reticulocytes, nucleated red blood cells, and/or malaria-infected cells. In some embodiments, the imaging is performed using the apparatus of this disclosure such as an apparatus comprising a particle counter, a visual analyzer and a processor.

As used herein, an exemplary complete blood count (CBC) can include a test panel typically requested by a doctor or other medical professional that provides information about the particles and/or cells in a patient's blood sample. Exemplary cells that circulate in the bloodstream can be generally divided into three types: including but not limited to, for example, white blood cells (e.g., leukocytes), red blood cells (e.g., erythrocytes), and platelets (e.g., thrombocytes).

As used herein, abnormally high or low counts may indicate the presence of disease, disorder, and/or condition. Thus, a CBC is one of the commonly performed blood tests in medicine, as it can provide an overview of a patient's general health status. Accordingly, a CBC is routinely performed during annual physical examinations.

As used herein, typically a phlebotomist collects the blood sample from the subject, the blood is generally drawn into a test tube typically containing an anticoagulant (e.g., EDTA, sometimes citrate) to stop it from clotting. The sample is then transported to a laboratory. Sometimes the sample is drawn off a finger prick using a Pasteur pipette for immediate processing by an automated counter. In one embodiment, the particle image is acquired while the particle is enveloped in a sheath fluid or PIOAL. In certain embodiments, the blood sample may be viewed on a slide prepared with a sample of the patient's blood under a microscope (a blood film, or peripheral smear). In certain embodiments, the complete blood count is performed by an automated analyzer.

As used herein, in general, blood analyzers can aspirate a very small amount of the specimen through narrow tubing. Sensors can detect the count and/or the number of cells passing through the tubing, and can identify the type of cell. Exemplary sensors may include detectors of light (e.g., visible, UV or IR) and/or electrical impedance. Exemplary detection parameters may include size, volume, and/or cellular features. In certain embodiments, the sensors can detect visible and non-visible light in a wavelength spectrum ranging from about 200 nm to about 10000 nm. In certain embodiments, the sensors can detect a wavelength of between about between 380 nm and about 760 nm, As used herein, data/parameters of a blood count can include, for example, total red blood cells; hemoglobin—the amount of hemoglobin in the blood; hematocrit or packed cell volume (PCV); mean corpuscular volume (MCV)—the average volume of the red cells (anemia is classified as microcytic or macrocytic based on whether this value is above or below the expected normal range. Other conditions that can affect MCV include thalassemia, reticulocytosis and alcoholism); mean corpuscular hemoglobin (MCH)—the average amount of hemoglobin per red blood cell, in picograms; mean corpuscular hemoglobin concentration (MCHC)—the average concentration of hemoglobin in the cells; red blood cell distribution width (RDW)—the variation in cellular volume of the RBC population; total white blood cells; neutrophil granulocytes (may indicate bacterial infection, typically increased in acute viral infections). Due to the segmented appearance of the nucleus, neutrophils are sometimes referred to as "segs" The nucleus of less mature neutrophils is not segmented, but has a band or elongated shape. Less mature neutrophils—those that have recently been released from the bone marrow into the bloodstream—are known as "bands". Other data/parameters for a blood count can also include, for example, lymphocytes (e.g., increased with some viral infections such as glandular fever, and in chronic lymphocytic leukemia (CLL), or decreased by HIV infection); monocytes (may be increased in bacterial infection, tuberculosis, malaria, Rocky Mountain spotted fever, monocytic leukemia, chronic ulcerative colitis and regional enteritis; eosinophil granulocytes (e.g., increased in parasitic infections, asthma, or allergic reaction); basophil granulocytes (e.g., increased in bone marrow related conditions such as leukemia or lymphoma.

As used herein, data/parameters of a blood count can also include, for example, data associated with platelets, including platelet numbers, information about their size and the range of sizes in the blood; mean platelet volume (MPV)—a measurement of the average size of platelets.

In another aspect of the methods of this invention, the cells contacted with particle contrast agent composition and/or imaged are abnormal cells, such as malaria-infected cells, atypical lymphocytes. In some aspects of this invention, the cells are abnormal cells which can be used to identify, predict, diagnose, prognose, or support a diagnosis of a condition, disease, infection and/or syndrome.

In another aspect of the methods of this invention, the cells are platelets.

Unless expressly indicated otherwise, references to "particle" or "particles" made in this disclosure will be understood to encompass any discrete or formed object dispersed in a fluid. As used herein, "particle" can include all measurable and detectable (e.g., by image and/or other measurable parameters) components in biological fluids. The particles are of any material, any shape and any size. In certain embodiments, particles can comprise cells. Examples of particles include but are not limited to cells, including blood cells, fetal cells, epithelials, stem cells, tumor cells, or bacteria, parasites, or fragments of any of the foregoing or other fragments in a biological fluid. Blood cells may be any blood cell, including any normal or abnormal, mature or immature cells which potentially exist in a biological fluid, for example, red blood cells (RBCs), white blood cells (WBCs), platelets (PLTs) and other cells. The members also include immature or abnormal cells. Immature WBCs may include metamyelocytes, myelocytes, pro-myelocytes and blasts. In addition to mature RBCs, members of RBCs may include nucleated RBCs (NRBCs) and reticulocytes. PLTs may include "giant" PLTs and PLT clumps. Blood cells and formed elements are further described elsewhere in this disclosure.

Exemplary particles can include formed elements in biological fluid samples, including for example, spherical and non-spherical particles. In certain embodiments, the particles can comprise non-spherical components. The image projection of non-spherical components can be maximized in the focal plane of the high optical resolution imaging device. In certain embodiments, the non-spherical particles are aligned in the focal plane of the high optical resolution imaging device (aligned in a plane substantially parallel to the direction of the flow). In some embodiments, platelets, reticulocytes, nucleated RBCs, and WBCs, including neutrophils, lymphocytes, monocytes, eosinophils, basophils, and immature WBCs including blasts, pro-myelocytes, myelocytes, or metamyelocytes are counted and analyzed as particles.

As used herein, detectable and measurable particle parameters can include, for example, visual and/or non-image based indices of size, shape, symmetry, contour and/or other characteristics.

The sample can be an isolated and/or prepared biological sample, including for example, a body fluid sample, a blood, serum, cerebrospinal fluid, pleural fluid, peritoneal fluid, saliva, seminal fluid, tears, sweat, milk, amniotic fluid, lavage fluid, bone marrow aspirate, effusions, exudates, or other sample obtained from a subject (e.g., biopsy sample that has been treated to produce a cell suspension, or a laboratory or production line sample comprising particles). In some embodiments, the sample can be a solid tissue sample, e.g., a biopsy sample that has been treated to produce a cell suspension. The sample may also be a suspension obtained from treating a fecal sample. A sample may also be a laboratory, chemical, industrial or production line sample comprising particles, such as a cell culture sample. The term sample may be used to refer to a sample obtained from a patient or laboratory or any fraction, portion or aliquot thereof. The sample can be diluted, divided into portions, or treated with a contrast agent in some processes.

The methods disclosed herein are applicable to samples from a wide range of organisms, including mammals, e.g., humans, non-human primates (e.g., monkeys), horses, cows or other livestock, dogs, cats or other mammals kept as pets, rats, mice, or other laboratory animals; birds, e.g., chickens; reptiles, e.g., alligators; fish, e.g., salmon and other farmed species; and amphibians.

The samples can be obtained by any conventional method, e.g., excretion, draw, harvesting, aspirate, or a biopsy. The sample can be from a subject considered to be healthy, for example, a sample collected as part of a routine physical examination. The sample can also be from a subject who has, who is at risk for, or who is suspected of having a disorder. The disorder can be the result of a disease, a genetic abnormality, an infection, an injury or unknown causes. Alternatively or in addition, the methods can be useful for monitoring a subject during the course of treatment for a disorder. Where there are signs of non-responsiveness to treatment and/or therapy, a clinician can choose an alternative or adjunctive agent. Depending upon the condition of the subject and the particular disorder, if any, samples can be collected once (or twice, three times, etc.) daily, weekly, monthly, or yearly.

The particles can vary depending upon the sample. The particles can be biological cells, for example, blood cells, fetal cells, stem cells, tumor cells or fragments thereof. In some embodiments the particles can be an infectious agent, for example, a virus or bacterium.

Reference to "blood cells" made in this disclosure will be understood to encompass any normal or abnormal, mature or immature cells which potentially exist in a biological fluid, for example, red blood cells (RBCs), white blood cells (WBCs), platelets (PLTs) and other cells. In general, normal RBCs, PLTs, and WBCs have a particle diameter in the range of 6-8 µm, 2-3 µm, and 8-15 µm, respectively. Normal RBCs, PLTs and WBCs are present in whole blood samples from normal patients in an approximate concentration range of $3.9-5.7 \times 10^{12}$ cells/L, $1.4-4.5 \times 10^{11}$ cells/L, $3.5-11 \times 10^{9}$ cells/L, respectively. See, Barbara J. Bain, Blood Cells, A Practical Guide, 4th ed., Blackwell Publishing, 2007, 34-36.

Reference to a "formed element" will be understood to encompass non-fluid elements present in biological fluid samples. Formed elements include, for example, classes of blood cells based on scientific classification or physiological function including erythrocytes (RBCs), leukocytes (WBCs) and platelets (PLTs), WBC clumps, subclasses of leukocytes, which include mature lymphocytes, and immature leukocytes such as monocytes, neutrophils, eosinophils, basophils. "Formed elements" for use herein will also include particles such as microorganisms, bacteria, fungi, parasites, or fragments thereof or other cell fragments. Major members of WBCs include but are not limited to neutrophils, lymphocytes, monocytes, eosinophils, and basophils. The members also include immature or abnormal cells. For example, immature WBCs may include metamyelocytes, myelocytes, pro-myelocytes. In addition to mature RBCs, members of RBCs may include nucleated RBCs (NRBCs) and reticulocytes. PLTs may include regular PLTs, and "giant" PLTs whose size is close to that of regular WBCs. Reference to a "member" or "members" of a category and/or subcategory of particles made in this disclosure will be understood to encompass individual particles within a category or sub-category of particles.

Unless expressly indicated otherwise, reference to a "category" of particles made in this disclosure will be understood to encompass a group of particles detected using at least one detection criterion measured, detected or derived such as size, shape, texture, or color. In some embodiments the members of at least one category and/or subcategory of particles counted by the apparatus of this disclosure will be the same type of formed element.

Such particles may be detected in a "channel." Reference to "channel" made in this disclosure will be understood to encompass a portion of the particle counter comprising a detector coupled to a signal source, providing an output that varies with greater or lesser detection of particles that meet at least one channel detection criterion. For example, a channel detection criterion can be based on size or volume of the particles. In some embodiments, the number of channels in a particle counter is one. In some other embodiments, the number of the channels in a particle counter is two or more.

One category and/or subcategory of particles detected in one channel of particle counter may comprise different classes and subclasses of particles, and grouped members of particles in two or more subclasses. Reference to a "category" of particles made in this disclosure will be understood to encompass a grouping of particles corresponding to criteria measured, detected or derived such as size, shape, texture, or color. In some embodiments the members of at least one category and/or subcategory of particles counted by the apparatus of this disclosure will be the same type of formed element.

As used herein, the term high optical resolution imaging device can include devices that are capable of obtaining particles images with sufficient visual distinctions to differentiate morphological features and/or changes. Exemplary high optical resolution imaging devices can include devices with an optical resolution of 1 um or lower, including for example, 0.4 to 0.5 um, such as for example, 0.46 um.

As used herein, the particle contrast agent compositions can be adapted for use in combination with a particle and/or intracellular organelle alignment liquid (PIOAL) in a visual analyzer for analyzing particles in a sample from a subject. The exemplary PIOAL is useful, as an example, in methods for automated recognition of different types of particles in a sample from a subject.

In another aspect, the cells may be enveloped in PIOAL when images are obtained. Suitable exemplary intracellular organelle alignment liquids are described herein.

As used herein, "alignment" can be characterized in part by the alignment of spherical and/or non-spherical particles. For example, particles such as non-spherical particles may be aligned in a plane substantially parallel to the direction of the flow. In certain embodiments, alignment of the non-spherical particles is characterized by the orientation of the particles increase an image projection of the non-spherical particles under imaging conditions in the focal plane of the high optical resolution imaging device. Particles such as spherical particles may have an increase in the amount of the in focus intraparticle contents of the particles and cells which is effective to generate visual distinctions for particle categorization and subcategorization. The intraparticle structures of particles such as spherical particles may be positioned, repositioned and/or better-positioned to be substantially parallel to the direction of flow. For example, intracellular structures, organelles or lobes may also be positioned, repositioned, and/or better-positioned to be substantially parallel to the direction of flow.

Reference to a "class" of particles made in this disclosure will be understood to encompass a group of particles based on scientific classification. For example, three major classes of blood cells exist in a whole blood sample, including RBCs, WBCs and PLTs.

Reference to a "member" or "members" of particles made in this disclosure will be understood to encompass particles in one category or subcategory of particles. For example, each category of blood cells can be further divided into subcategories or members. Major members of WBCs include but are not limited to neutrophils, lymphocytes, monocytes, eosinophils, and basophils. The members also include immature or abnormal cells. For example, immature WBCs may include metamyelocytes, myelocytes, and promyelocytes. In addition to mature RBCs, members of RBCs may include nucleated RBCs (NRBCs) and reticulocytes. PLTs may include regular PLTs, and "giant" PLTs whose size is close to that of regular WBCs.

Reference to "immature cells" will be understood to encompass cells in a certain developmental stage, for example, inside the bone marrow or shortly after release from bone marrow but before full development into a mature cell.

Reference to "abnormal cells" will be understood to encompass cells with irregular morphological characteristics or cells associated with a certain disease or condition, or irregularities associated which may in some instances be associated with certain diseases or conditions. Examples of certain disease include but are not limited to erythrocytosis, polycythemia, anemia, erythroblastopenia, leukocytosis, leukopenia, lymphocytosis, lymphocytopenia, granulocytosis, granulocytopenia or agranulocytosis, neutrophilia, neutropenia, eosinophilia, eosinopenia, basophilia, basopenia, thrombocytosis, thrombocytopenia, and pancytopenia. A class of cells may increase or decrease in the bloodstream. In some conditions, abnormal cells much larger than regular white cells exist at a small concentration in a blood sample. Variations in size, shape, color, and/or intracellular structures may be associated with certain diseases or conditions.

Reference to "count" of particles or "particle count" made in this disclosure will be understood to encompass the numbers of particles obtained from one channel of a particle counter. Reference to "concentration" of a class or a member of particles made in this disclosure will be understood to mean the numbers of the particles per unit volume (e.g., per liter) or per sample of a known volume. For example, a particle counter may provide counts or concentrations or other count based function for categories of particles, while a visual analyzer may provide counts, concentrations, ratios or other concentration based parameters for each category or subcategory of particles.

Reference to "ratio" made in this disclosure will be understood to encompass any quantitative and/or proportionate ratio of two categories/subcategories, classes or members of particles. Examples of such a ratio include but are not limited to a ratio by concentration, weight, and/or by numbers of particles. Typically the ratio concerns the numerical fraction of the count of one category, class or member over the count of another such category, class or member. In some embodiments, determinations using weighted counts or weighted and/or proportionate ratios may also be made.

Hematology—Particle Analysis System

Turning now to the drawings, FIG. 1 schematically shows an exemplary flowcell 22 for conveying a sample fluid through a viewing zone 23 of a high optical resolution imaging device 24 in a configuration for imaging microscopic particles in a sample flow stream 32 using digital image processing. Flowcell 22 is coupled to a source 25 of sample fluid which may have been subjected to processing, such as contact with a particle contrast agent composition and heating. Flowcell 22 is also coupled to one or more sources 27 of a particle and/or intracellular organelle alignment liquid (PIOAL), such as a clear glycerol solution having a viscosity that is greater than the viscosity of the sample fluid.

The sample fluid is injected through a flattened opening at a distal end 28 of a sample feed tube 29, and into the interior of the flowcell 22 at a point where the PIOAL flow has been substantially established resulting in a stable and symmetric laminar flow of the PIOAL above and below (or on opposing sides of) the ribbon-shaped sample stream. The sample and PIOAL streams may be supplied by precision metering pumps that move the PIOAL with the injected sample fluid along a flowpath that narrows substantially. The PIOAL envelopes and compresses the sample fluid in the zone 21 where the flowpath narrows. Hence, the decrease in flowpath thickness at zone 21 can contribute to a geometric focusing of the sample stream 32. The sample fluid ribbon 32 is enveloped and carried along with the PIOAL downstream of the narrowing zone 21, passing in front of, or otherwise through the viewing zone 23 of, the high optical resolution imaging device 24 where images are collected, for example, using a CCD 48. Processor 18 can receive, as input, pixel data from CCD 48. The sample fluid ribbon flows together with the PIOAL to a discharge 33.

As shown here, the narrowing zone 21 can have a proximal flowpath portion 21a having a proximal thickness PT and a distal flowpath portion 21b having a distal thickness DT, such that distal thickness DT is less than proximal thickness PT. The sample fluid can therefore be injected through the distal end 28 of sample tube 29 at a location that is distal to the proximal portion 21a and proximal to the distal portion 21b. Hence, the sample fluid can enter the PIOAL envelope as the PIOAL stream is compressed by the zone 21. wherein the sample fluid injection tube has a distal exit port through which sample fluid is injected into flowing sheath fluid, the distal exit port bounded by the decrease in flowpath size of the flowcell.

The digital high optical resolution imaging device 24 with objective lens 46 is directed along an optical axis that intersects the ribbon-shaped sample stream 32. The relative distance between the objective 46 and the flowcell 33 is variable by operation of a motor drive 54, for resolving and collecting a focused digitized image on a photosensor array.

According to some embodiments, the system can operate to hydrofocus the sample fluid ribbon 32. The term hydrofocus or hydrofocusing can refer to a focusing effect which is influenced by a viscosity difference between the sheath and sample fluids, a geometric narrowing transition zone of the flowcell, and a velocity difference between the sheath and sample fluids. Hydrodynamic flow results from the velocity difference between the sample and sheath fluid streams, which affects the flow ribbon thickness and shape. Flowcell A practical embodiment of flowcell 22 is further depicted in FIGS. 2 and 3. As shown here, flowcell 22 can be coupled with a sample source 25 and also to a source 27 of PIOAL material. The sample fluid is injected into the flowcell 22 via the cannula 29, for example through a distal exit port 31 of the cannula 29. Typically, the PIOAL sheath fluid is not in a laminar flow state as it travels through a curved channel section 41 in the flowcell from the source 27 toward the viewing zone 23. However, the flowcell 22 can be configured so that the PIOAL sheath fluid is or becomes laminar, or presents a flat velocity profile, as it flows past the distal exit port 31 where sample fluid is introduced into the flowing sheath fluid. The sample fluid and the PIOAL can flow along the flowcell 22 in a direction generally indicated by arrow A, and then out of the flowcell 22 via discharge 33. The flowcell 22 defines an internal flowpath 20 that narrows symmetrically (e.g. at transition zone 21) in the flow direction A. The symmetry of the flowpath contributes to a robust and centered flow of the sample stream. The flowcell 22 is configured to direct a flow 32 of the sample enveloped with the PIOAL through a viewing zone 23 in the flowcell, namely behind viewing port 57. Associated with the viewport 57 is an autofocus pattern 44. Flowcell 22 also has a rounded or recessed seat 58 which is configured to accept or receive a microscope objective (not shown).

According to some embodiments, the autofocus pattern 44 can have a position that is fixed relative to the flowcell 22, and that is located at a displacement distance from the plane of the ribbon-shaped sample stream 32. In the embodiment shown here, the autofocus pattern (target 44) is applied directly to the flowcell 22 at a location that is visible in an image collected through viewport 57 by a high optical resolution imaging device (not shown). Flowcell 22 can be constructed from a single piece of material. Alternatively, flowcell 22 can be constructed of a first or upper section or layer 22a and a second or lower section or layer 22b. As shown here, a glass or transparent window pane 60 is attached to or integral with the first section 22a. The pane 60 can define at least a portion of the sample flowpath within the flowcell. Light from light source 42 can travel through an aperture or passage of the autofocus pattern 44 so as to illuminate sample particles flowing within the flow stream 32.

In some cases, the thickness of pane 60 can have a value within a range from about 150 μm to about 170 μm. As noted above, the pane 60 can define or form part of the flowpath or sheath (e.g. PIOAL) channel. By using a thin pane 60, it is possible to place the microscope objective very close to the sample fluid ribbon, and hence obtain highly magnified images of particles flowing along the flowpath.

Figure 3:
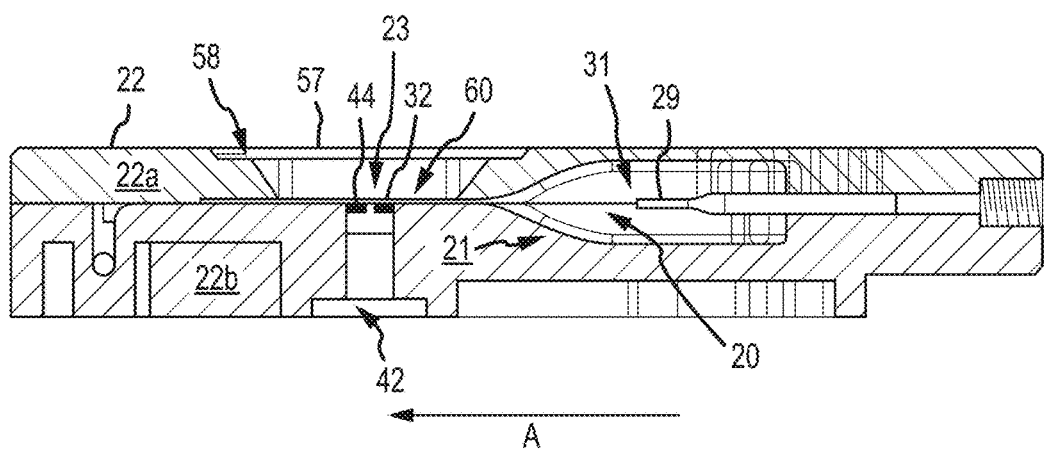
FIG. 3 is a longitudinal median section view along lines 3-3 of the flowcell shown in FIG. 2.
Figure 3A:
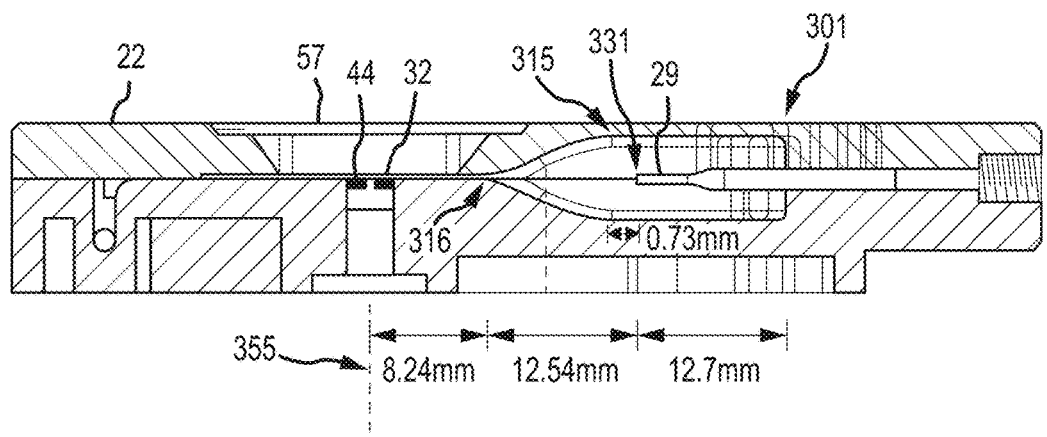
FIGS. 3A and 3B provide additional section views of flowcells according to embodiments of the present invention.
Figure 3B:
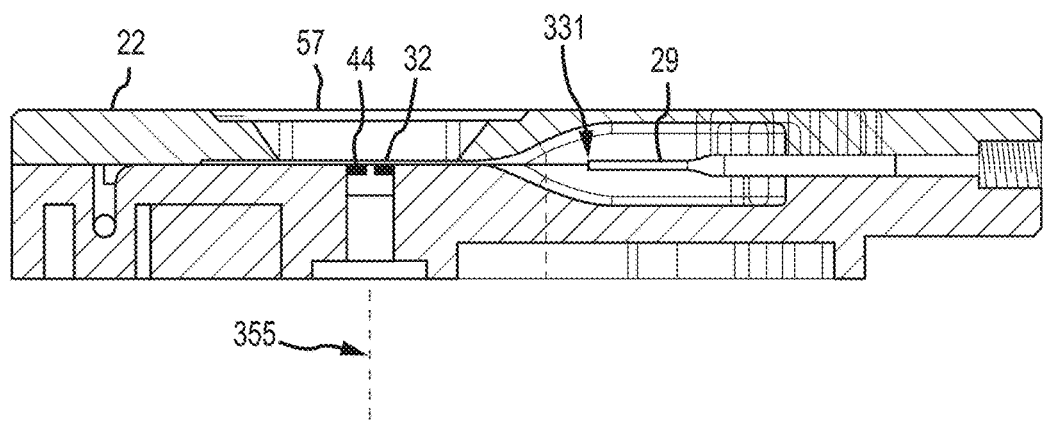

FIG. 3A depicts aspects of a flowcell embodiment, where a distance between the imaging axis 355 and the distal transition zone portion 316 is about 8.24 mm. A distance between the distal transition zone portion 316 and the cannula exit port 331 is about 12.54 mm. A distance between the cannula exit port 331 and the sheath fluid entrance 301 is about 12.7 mm. A distance between the cannula exit port 331 and a proximal transition zone portion 318 is about 0.73 mm. FIG. 3B depicts aspects of a flowcell embodiment where the cannula exit port has been moved to a more distal location relative transition zone, as compared to the FIG. 3A embodiment. As shown here, the cannula distal end is advanced into the narrowing transition zone of the flowcell, and a distance between the imaging axis 355 and the distal transition zone portion 316 is within a range from about 16 mm to about 26 mm. In some case, the distance between the imaging axis 355 and the distal transition zone portion 316 is about 21 mm.

With returning reference to FIG. 1, the flowcell internal contour (e.g. at transition zone 21) and the PIOAL and sample flow rates can be adjusted such that the sample is formed into a ribbon shaped stream 32. The stream can be approximately as thin as or even thinner than the particles that are enveloped in the ribbon-shaped sample stream.

White blood cells may have a diameter around 10 µm, for example. By providing a ribbon-shaped sample stream with a thickness less than 10 µm, the cells may be oriented when the ribbon-shaped sample stream is stretched by the sheath fluid, or PIOAL. Surprisingly stretching the ribbon-shaped sample stream along a narrowing flowpath within PIOAL layers of different viscosity than the ribbon-shaped sample stream, such as higher viscosity, advantageously tends to align non-spherical particles in a plane substantially parallel to the flow direction, and apply forces on the cells, improving the in-focus contents of intracellular structures of cells. The optical axis of the high optical resolution imaging device 24 is substantially normal (perpendicular) to the plane of the ribbon-shaped sample stream. The linear velocity of the ribbon-shaped sample stream at the point of imaging may be, for example, 20-200 mm/second. In some embodiments, the linear velocity of the ribbon-shaped sample stream may be, for example, 50-150 mm/second.

The ribbon-shaped sample stream thickness can be affected by the relative viscosities and flow rates of the sample fluid and the PIOAL. The source 25 of the sample and/or the source 27 of the PIOAL, for example comprising precision displacement pumps, can be configured to provide the sample and/or the PIOAL at controllable flow rates for optimizing the dimensions of the ribbon-shaped sample stream 32, namely as a thin ribbon at least as wide as the field of view of the high optical resolution imaging device 24.

In one embodiment, the source 27 of the PIOAL is configured to provide the PIOAL at a predetermined viscosity. That viscosity may be different than the viscosity of the sample, and can be higher than the viscosity of the sample. The viscosity and density of the PIOAL, the viscosity of the sample material, the flow rate of the PIOAL and the flow rate of the sample material are coordinated to maintain the ribbon-shaped sample stream at the displacement distance from the autofocus pattern, and with predetermined dimensional characteristics, such as an advantageous ribbon-shaped sample stream thickness.

In a practical embodiment, the PIOAL has a higher linear velocity than the sample and a higher viscosity than the sample, thereby stretching the sample into the flat ribbon. The PIOAL viscosity can be up to 10 centipoise.

Figure 2:
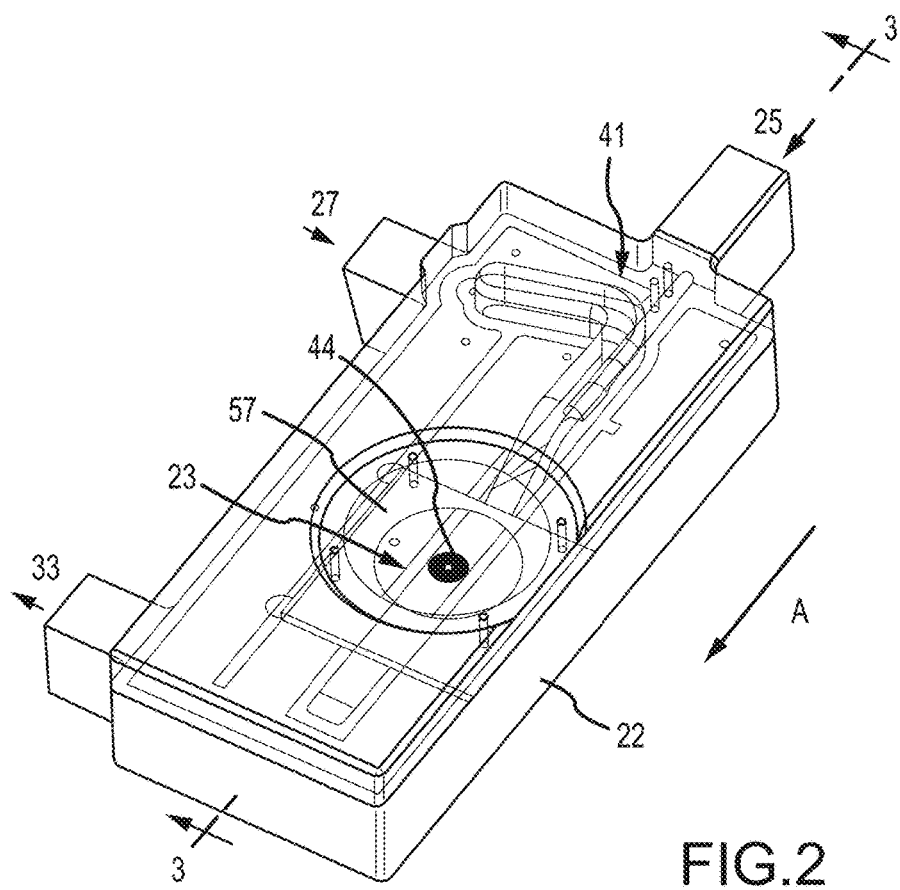
FIG. 2 is a perspective illustration of a flowcell according to an exemplary embodiment.

Referring also to FIGS. 2 and 3, the internal flowpath of the flowcell narrows downstream of the point of injection of the ribbon-shaped sample stream into the PIOAL, to produce a ribbon-shaped sample stream thickness, for example, up to 7 µm, and/or the internal flowpath produces a ribbon-shaped sample stream width of 500-3,000 µm. In exemplary embodiments, as depicted in FIG. 1, the internal flowpath of the flowcell begins a narrowing transition zone upstream of the point of injection of the sample stream into the PIOAL.

In another embodiment the internal flowpath narrows to produce a ribbon-shaped sample stream thickness of 2-4 µm in thickness, and/or the internal flowpath results in the ribbon-shaped sample stream of 2000 µm in width. These dimensions are particularly useful for hematology. The thickness of the stream in this case is less than the diameter of some particles, such as red blood cells in their relaxed state. Accordingly, those particles can become reoriented to face their wider a dimension to the imaging axis, which is helpful in revealing distinguishing characteristics.

The linear velocity of the ribbon-shaped sample stream can be limited sufficiently to prevent motion blurring of the digitized image at the image exposure time of the photosensor array. The light source can optionally be a strobe light that is flashed to apply high incident amplitude for a brief time. Inasmuch as the autofocus pattern 44 and the image are in the same field of view, the light source is configured to illuminate the ribbon-shaped sample stream and the autofocus pattern simultaneously. However in other embodiments, the field of view for imaging and for autofocus can be different, e.g., illuminated and/or imaged separately.

The subject developments have method as well as apparatus aspects. A method of focusing a visual analyzer comprises focusing a high optical resolution imaging device 24, which may be a digital high optical resolution imaging device or the digital image capture device, on an autofocus pattern 44 fixed relative to a flowcell 22, wherein the autofocus pattern 44 is located at a displacement distance 52 from a ribbon-shaped sample stream 32. The digital high optical resolution imaging device 24 has an objective with an optical axis that intersects the ribbon-shaped sample stream 32. A relative distance between the objective and the flowcell 22 is varied by operation of a motor drive 54, whereas the distance along the optical axis between the high optical resolution imaging device and the point of optimal focus is known. The digital high optical resolution imaging device is configured to resolve and collect a digitized image on a photosensor array. The motor drive is operated to focus on the autofocus pattern in an autofocus process. The motor drive then is operated over the displacement distance, thereby focusing the high optical resolution imaging device on the ribbon-shaped sample stream.

The method further can further include forming the ribbon-shaped sample stream into a ribbon-shape. The ribbon shape is presented such that the optical axis of the high optical resolution imaging device is substantially perpendicular to the ribbon-shaped sample stream, namely normal to the plane of the ribbon-shaped stream.

Figure 4:
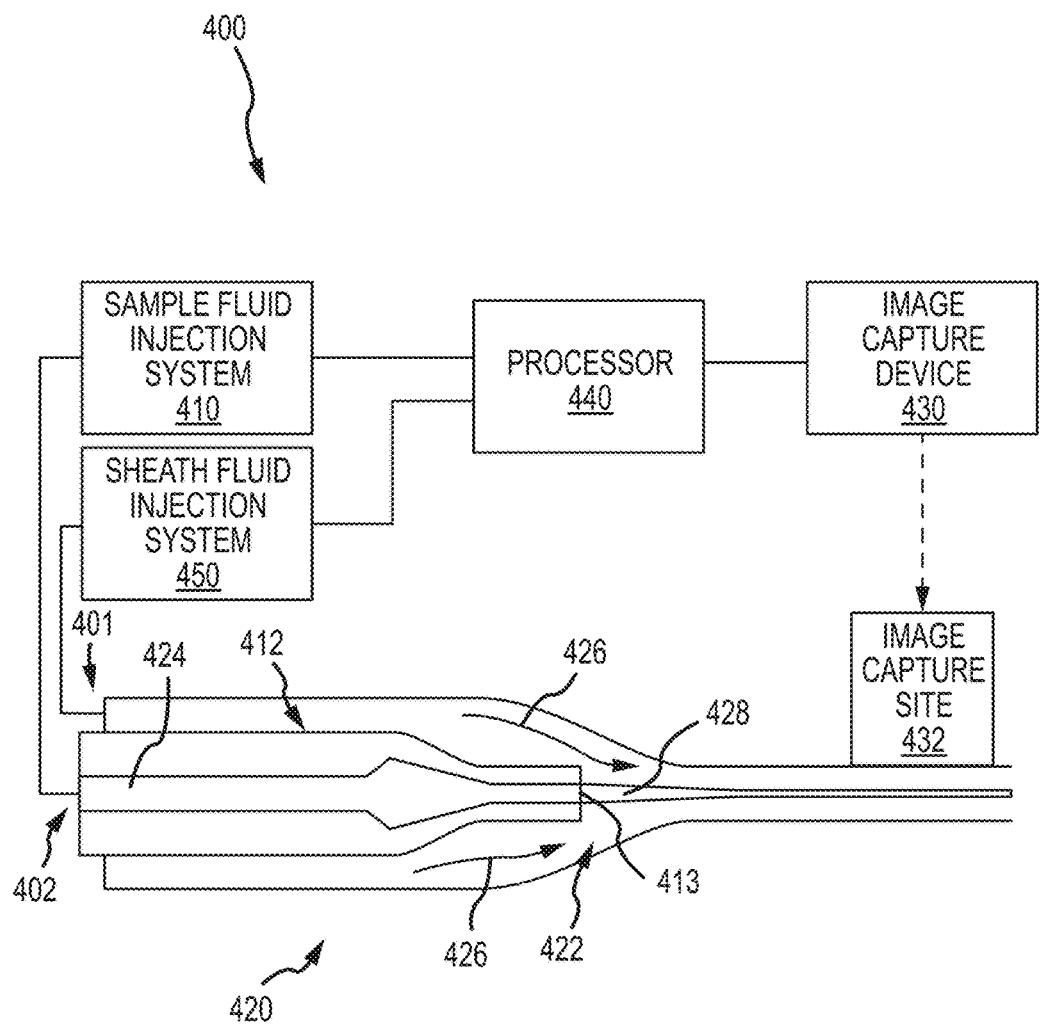
FIG. 4 depicts aspects of an analyzer system according to embodiments of the present invention.

FIG. 4 depicts aspects of a system 400 for imaging particles in a blood fluid sample. As shown here, system 400 includes a sample fluid injection system 410, a flowcell 420, and image capture device 430, and a processor 440. The flowcell 420 provides a flowpath 422 that transmits a flow of the sheath fluid, optionally in combination with the sample fluid. According to some embodiments, the sample fluid injection system 410 can include or be coupled with a cannula or tube 412. The sample fluid injection system 410 can be in fluid communication with the flowpath 422 (e.g. via sample fluid entrance 402), and can operate to inject sample fluid 424 through a distal exit port 413 of the cannula 412 and into a flowing sheath fluid 426 within the flowcell 420 so as to provide a sample fluid stream 428. For example, the processor 440 may include or be in operative association with a storage medium having a computer application that, when executed by the processor, is configured to cause the sample fluid injection system 410 to inject sample fluid 424 into the flowing sheath fluid 426. As shown here, sheath fluid 426 can be introduced into the flowcell 420 by a sheath fluid injection system 450 (e.g. via sheath fluid entrance 401). For example, the processor 440 may include or be in operative association with a storage medium having a computer application that, when executed by the processor, is configured to cause the sheath fluid injection system 450 to inject sheath fluid 426 into the flowcell 420.

The sample fluid stream 428 has a first thickness T1 adjacent the injection tube 412. The flowpath 422 of the flowcell having a decrease in flowpath size such that the thickness of the sample fluid stream 428 decreases from the initial thickness T1 to a second thickness T2 adjacent an image capture site 432. The image capture device 430 is aligned with the image capture site 432 so as to image a first plurality of the particles from the first sample fluid at the image capture site 432 of the flowcell 420.

The processor 440 is coupled with the sample fluid injector system 410, the image capture device 430, and optionally the sheath fluid injection system 450. The processor 440 is configured to terminate injection of the first sample fluid into the flowing sheath fluid 426 and begin injection of the second sample fluid into the flowing sheath fluid 426 such that sample fluid transients are initiated. For example, the processor 440 may include or be in operative association with a storage medium having a computer application that, when executed by the processor, is configured to cause the sample fluid injection system 410 to inject the second sample fluid into the flowing sheath fluid 426 such that sample fluid transients are initiated.

Further, the processor 440 is configured to initiate capture of an image a second plurality of the particles from the second sample fluid at the image capture site 432 of the flowcell 420 after the sample fluid transients and within 4 seconds of the imaging of the first plurality the particles. For example, the processor 440 may include or be in operative association with a storage medium having a computer application that, when executed by the processor, is configured to cause the image capture device 430 to initiate capture of an image a second plurality of the particles from the second sample fluid at the image capture site 432 of the flowcell 420 after the sample fluid transients and within four seconds of the imaging of the first plurality the particles.

Figure 4A:
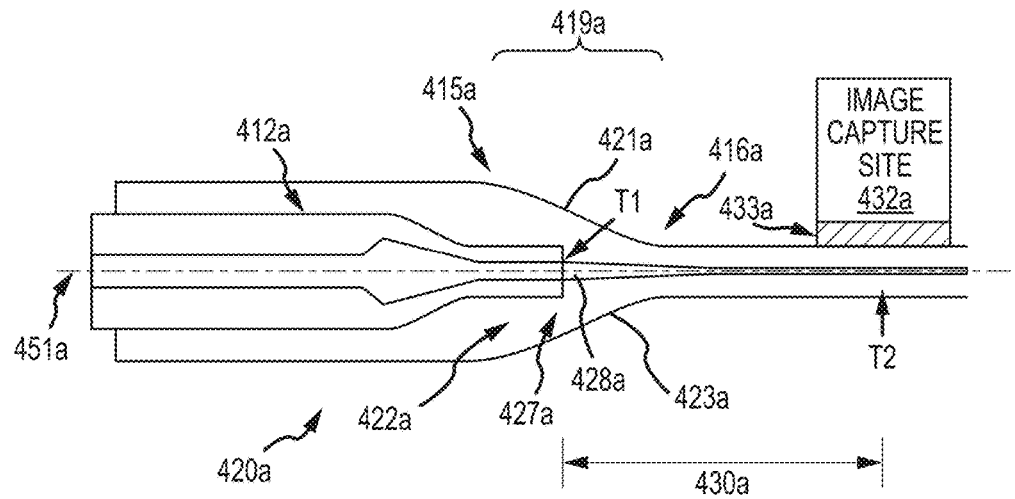

As shown in the flowcell embodiment depicted in FIG. 4A, a decrease in flowpath size (e.g. at transition zone 419*a*) can be defined by opposed walls 421*a*, 423*a* of the flowpath 422*a*. The opposed walls 421*a*, 423*a* can angle radially inward along the flowpath 422*a*, generally symmetric about a transverse plane 451*a* that bisects the sample fluid stream 428*a*. The plane 451*a* can bisect the sample stream 428*a* where the sample stream has a first thickness T1, at a location where the sample stream 428*a* exits a distal portion 427*a* of the cannula or sample injection tube 412*a*. Similarly, the plane 451*a* can bisect the sample stream 428*a* where the sample stream has a second thickness T2, at a location where the sample stream 428*a* passes the image capture site 432*a*. According to some embodiments, the first thickness T1 has a value of about 150 μm and the second thickness T2 has a value of about 2 μm. In such cases, the compression ratio of the sample ribbon stream is 75:1. According to some embodiments, the first thickness T1 has a value within a range from about 50 μm to about 250 μm and the second thickness T2 has a value within a range from about 2 μm to about 10 μm. As the sample stream fluid flows through the flowcell, the ribbon thins out as it accelerates and is stretched. Two features of the flowcell can contribute to thinning of the sample fluid ribbon. First, a velocity difference between the sheath fluid envelope and the sample fluid ribbon can operate to reduce the thickness of the ribbon. Second, the tapered geometry of the transition zone can operate to reduce the thickness of the ribbon.

As depicted in FIG. 4A (as well as in FIGS. 4 and 4B-1), the transition zone 419*a* can be defined by an angular transitions at the proximal (415*a*) and distal (416*a*) portions. It is also understood that the transition zone 419*a* can instead present smooth or curved transitions at the proximal (415*a*) and distal (416*a*) portions, similar to the smooth or curved transitions as depicted in FIGS. 1, 3, 3A, 3B, and 4B-2).

Typically, the first thickness T1 is much larger than the size of the sample particles, and hence the particles are contained entirely within the sample ribbon stream. However, the second thickness T2 may be smaller than the size of certain sample particles, and hence those particles may extend out of the sample fluid and into surrounding sheath fluid. As shown in FIG. 4A, the sample ribbon stream can flow generally along the same plane as it exits the cannula and travels toward the image capture site.

The flowcell can also provide a separation distance 430*a* between the distal cannula portion 427*a* and the image capture site 432*a*. According to some embodiments, the distal portion 427*a* of the sample fluid injection tube 412*a* can be positioned at an axial separation distance 430*a* from the image capture site 432*a*, where the axial separation distance 432*a* has a value of about 21 mm. In some cases, the axial separation distance 430*a* has a value within a range from about 16 mm to about 26 mm.

The axial separation distance 430*a* between the cannula exit port and image capture site can impact the transition time for the sample fluid as the fluid travels from the exit port to the image capture site. For instance, a relatively shorter axial separation distance 430*a* can contribute to a shorter transition time, and a relatively longer axial separation distance 430*a* can contribute to a longer transition time.

The position of the exit port at the cannula distal portion 427*a* relative to the flowpath transition zone 419*a*, or relative to the proximal portion 415*a* of the flowpath transition zone 419*a*, can also inference the transition time for the sample fluid as the fluid travels from the exit port to the image capture site. For example, the sheath fluid may have a relatively slower speed at the proximal portion 415*a*, and a relatively faster speed at a location between the proximal portion 415*a* and the distal portion 416*a*. Hence, if the cannula exit port at distal portion 427*a* is positioned at the proximal portion 415*a*, it will take a longer amount of time for the sample fluid to reach the image capture site, not only because the travel distance is longer, but also because the initial speed of the sample fluid after it exits the cannula distal port is slower (due to the slower sheath fluid speed). Put another way, the longer the sample fluid is present in the thicker portion (e.g. near proximal portion 415*a*) of the flowcell, the longer it takes the sample to reach the image capture site. Conversely, if the cannula exit port at distal portion 427*a* is positioned distal to the proximal portion 415*a* (e.g. at a central location between proximal portion 415*a* and distal portion 416*a*, as depicted in FIG. 4A), it will take a shorter amount of time for the sample fluid to reach the image capture site, not only because the travel distance is shorter, but also because the initial speed of the sample fluid after it exits the cannula distal port is faster (due to the faster sheath fluid speed). As discussed elsewhere herein, the sheath fluid is accelerated as it flows through the transition zone 419*a*, due to the narrowing cross-sectional area of the zone 419*a*.

According to some embodiments, with a shorter transition time, more time is available for image collection at the image capture site. For example, as the duration of the transition time from the cannula distal tip to the imaging area decreases, it is possible to process more samples in a specific amount of time, and relatedly it is possible to obtain more images in a specific amount of time (e.g. images per minute).

Although there are advantages associated with positioning the exit port of the cannula distal portion 427*a* more closely to the image capture site 432*a*, it is also desirable to maintain a certain distance between the port and the capture site. For example, as depicted in FIG. 3, an optical objective or front lens of an imaging device can be positioned in the seat 58 of the flowcell 22. If the exit port 31 of the cannula is too close to the seat 58, then the sample fluid may not be sufficient stabilized after it is injected into the sheath fluid so as to provide desired imaging properties at the image capture site. Similarly, it may be desirable to maintain the tapered transition region 21 at a distance from the viewing zone 23, so that the tapered region does not interfere with the positioning of the seat 58 which receives the image capture device objective.

With continuing reference to FIG. 4A, the downstream end 427a of the sample fluid injection tube 412a can be positioned distal to a proximal portion 415a of the flowpath transition zone 419a. Relatedly, the downstream end 427a of the sample fluid injection tube 412a can be positioned proximal to a distal portion 416a of the flowpath transition zone 419a. Hence, according to some embodiments, the sample fluid can be injected from the injection cannula 412a and into the flowcell at a location within the transition zone 419a.

According to some embodiments, symmetry in the decrease in flowpath size (e.g. at flowpath transition zone 419a) operates to limit particle misalignment in the blood fluid sample. For example, such symmetry can be effective to limit red blood cells imaging orientation misalignment in the blood fluid sample to less than about 20%.

According to some embodiments, methods disclosed herein are operable to the flagging rate during blood count analysis to below 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6% or 5% of samples.

According to some embodiments, the image capture site 432a has a field of view 433a of between about 150 μm×150 μm and 400 μm×400 μm. In some cases, the image capture site 432a has a field of view 433a of about 275 μm×275 μm. In some cases, the field of view can be defined in terms of length times width. If expressed as surface area, a 275 μm×275 μm field of view has an area of 75,625 μm$^2$. According to some embodiments, the field of view can be determined by the imaging device objective and its magnification. In some cases, the field of view can correspond to the extent of the field (area) that is imaged by the collection optics (e.g. objective, tube lens, and camera). In some cases, the field of view is much smaller than the viewing port of transparent area at the image capture site.

FIGS. 4A-1 and 4A-2 illustrate the effects of hydrofocusing on the sample stream as it travels from the cannula exit port to the image capture site. As shown in FIG. 4A-1, the sample stream can have a height H(S) of about 150 μm and a width W(S) of about 1350 μm. Further, the PIOAL sheath stream can have a height H(P) of about 6000 μm and a width W(P) of about 4000 μm. Subsequent to the hydrofocusing, as shown in FIG. 4A-2, the sample stream can have a height H(S) of about 2 μm and a width W(S) of about 1350 μm. Further, the PIOAL sheath stream can have a height H(P) of about 150 μm and a width W(P) of about 4000 μm. In one embodiment, the cross sectional area of the PIOAL sheath stream at the cannula exit is 40 times larger than the cross sectional area near the image capture site.

According to some embodiments, it can be useful to determine the cross-section of the flowcell channel at the image capture site. This can correspond to the PIOAL sheath stream height H(P) of about 150 μm and a width W(P) of about 4000 μm as depicted in FIG. 4A-2. It can also be useful to determine the volumetric flow rate of the combined sample and sheath fluid streaming through the flowcell at the image capture site. When the cross-section area and the flow rate are known, it is possible to determine the velocity of the combined sample and sheath fluid at the image capture site.

According to some embodiments, the flow of the sample and sheath fluids through the flowcell can be approximated with a parallel plate profile model. Relatedly, the flow rate in the center of the sample fluid stream (e.g. as depicted in FIG. 4A-2), can be about 1.5 times the average flow rate of the combined sample and sheath fluid stream.

According to some embodiments, the cross-sectional area of the sample flow at the cannula exit (e.g. W(S)×H(S) in FIG. 4A-1) is 40 times larger than the cross-sectional area of the sample flow at the imaging site (e.g. W(S)×H(S) in FIG. 4A-2). The volumetric flow rate of sheath fluid at the imaging area can be about 45 μL/second. The volumetric flow rate of sample fluid at the imaging area can be about 0.232 μL/second. In some cases, the cross-sectional area of the combined sheath and sample streams at the imaging site is 600,000 μm$^2$. In some cases, the average flowstream velocity at the imaging site is 75 mm/second.

The flow rate or velocity can be determined as the rate that results in clear and focused cellular images. Exemplary flow rates and velocities were discovered based on flow rates of the two samples that were observed to achieve certain sample flowstream ribbon shapes or characteristics at the imaging site. For example, at flow rate of about 75 mm/sec (or within a range from 20-200 mm/sec), the cells do not flow too slow such that there are overlaps of cells in consecutive images, and the cells do not flow too fast such that ghosting effects are created (blurred image). Relatedly, by avoiding excessively high flow rates, it is possible to conserve more reagent and sample. According to some embodiments, an optimal or desired linear velocity can be achieved by either changing the volumetric flow (pump rate) or the shape of cannula.

The flow velocity of the sample stream through the image capture zone can also be related to the performance of the image capture device relative to the flowcell function. For example, if the sample stream if flowing too quickly, it may be difficult to obtain clear images of particles contained in the sample (e.g. the shutter speed of the image capture device may be too low, thus producing a blurred image). Similarly, if the sample stream is flowing too slowly, the image capture device may obtain consecutive images of the same particle (e.g. the same particle remains in the capture frame during two image captures). In some embodiments, the velocity of the sample ribbon can be modulated (e.g. by adjusting any of a variety of the flowcell operational parameters) relative to the image capture rate, so that there is minimal flow between frame captures, and hence a high percentage of the sample is imaged.

According to some embodiments, the particle analysis system and associated components can be configured so that as the sheath fluid and fluid sample flow through the flowcell, the sheath fluid can flow at a sheath fluid volumetric rate of 45 μL/s and the fluid sample can flow at a fluid sample volumetric flow rate of 0.232 μL/s (or within a range from 0.2 to 0.35 μL/s). In some cases, the ratio of the sheath fluid flow rate to the sample fluid flow rate is about 200. In some cases, the ratio of the sheath fluid flow rate to the sample fluid flow rate has a value within a range from about 70 to 200. In some cases, the ratio of the sheath fluid flow rate to the sample fluid flow rate is about 193. In some cases, the ratio of the sheath fluid flow rate to the sample fluid flow rate is about 70. In some instances, a ratio of sheath fluid volume to fluid sample volume flowing within the flowcell can be within a range from 25:1 to 250:1.

According to some embodiments, the system and associated components can be configured so that as sheath and fluid sample flow through the flowcell 420, the sheath fluid can flow at a sheath fluid velocity of 75 mm/sec before the imaging area and the fluid sample can flow at a fluid sample velocity of 130 mm/sec before the imaging area. In some instances, a ratio of sheath fluid volume to fluid sample volume flowing within the flowcell can be within a range from 100:1 to 200:1.

In some instances, a flowcell can have a minimum compression ratio of about 50:1 and a maximum compression ratio of about 125:1. In some cases, the minimum compression ratio can be about 30:1 or 20:1. This compression ratio refers to the ratio of flow stream thicknesses H(S):H(S) when comparing FIG. 4A-1 to FIG. 4A-2. This compression ratio can be influenced by a combination of geometric compression (e.g. the ratio of the sheath fluid thicknesses H(P):H(P) when comparing FIG. 4A-1 to FIG. 4A-2, which can also correspond generally to the dimensions of the flowcell narrowing tapered transition zone 419a shown in FIG. 4A) and a hydrodynamic compression (e.g. also corresponding to a difference in velocity). According to some embodiments, the geometric compression ratio is about 40:1.

Figures 1, 2, 4B:
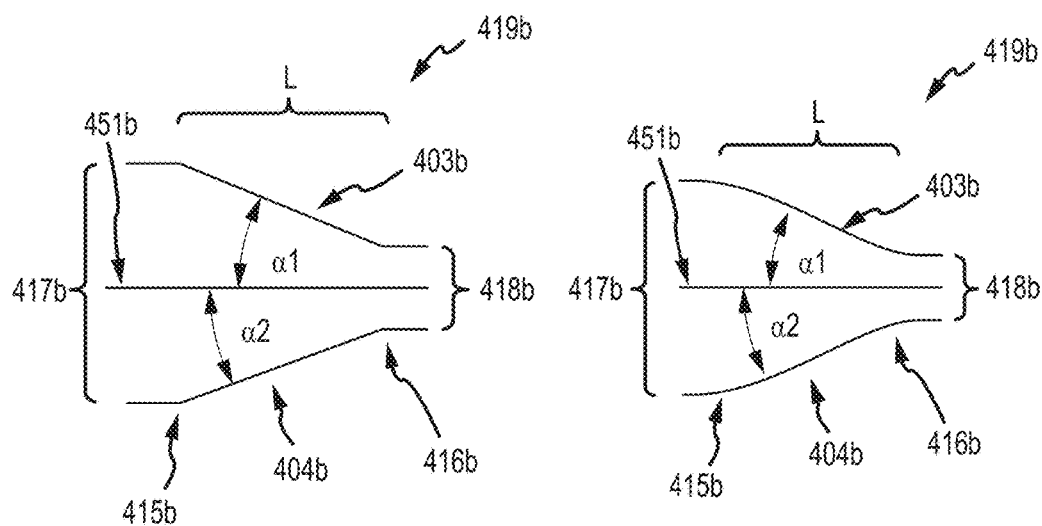
Figures 1, 4A:
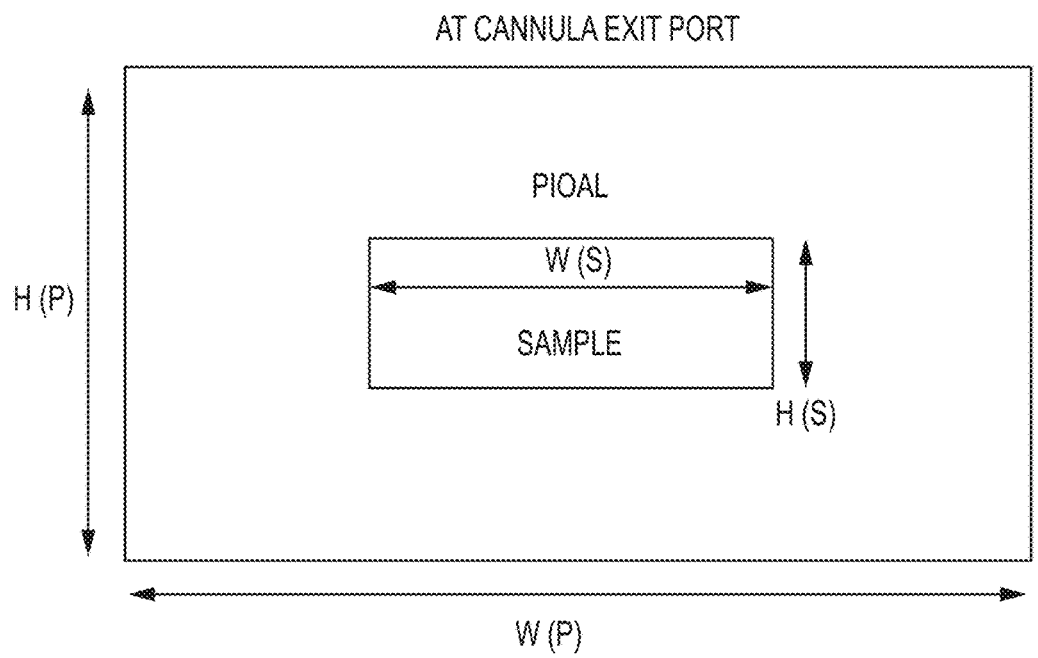
Figures 2, 4A:
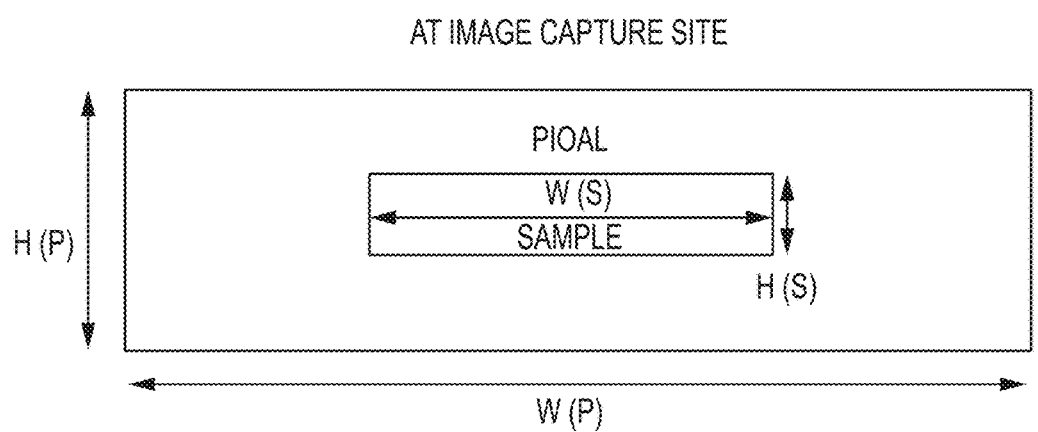

The decrease in flowpath size, corresponding to the transition zone, can be defined by a proximal flowpath portion having a proximal thickness or height, and a distal flowpath portion having a distal thickness or height that is less than the proximal thickness or height. For example, as shown in the partial views of FIGS. 4B-1 and 4B-2, the transition zone 419b of the flowpath can have a length L between a proximal portion 415b and a distal portion 416b, where the proximal portion 415b has a proximal height 417b, and the distal portion 416b has a distal height 418b. As depicted in FIG. 4B-2, and as noted elsewhere herein, the shape or contour of the transition zone can be curved or smooth, and for example can be provided in the shape of an S-curve, a sigmoidal curve, or a tangent curve. According to some embodiments, the proximal height 417b has a value of about 6000 µm. In some cases, the proximal height 417b has a value within a range from about 3000 µm to about 8000 µm. According to some embodiments, the distal height 418b has a value of about 150 µm. In some cases, the distal height 418b has a value within a range from about 50 µm to about 400 µm.

The geometry of the transition zone 419a can provide a first angle α1 between the first flowpath boundary 403b and the bisecting transverse plane 451b, and a second angle α2 between the second flowpath boundary 404b and the bisecting transverse plane 451b. In some cases, angle α1 is about 45 degrees and angle α2 is about 45 degrees. In some cases, angle α1 has a value within a range from about 10 degrees to about 60 degrees. In some cases, angle α2 has a value within a range from about 10 degrees to about 60 degrees. According to some embodiments, angles α1 and α2 have the same value. The angles α1 and α2 can be selected so as to maintain laminar flow or minimize turbulence of the sample fluid as it travels from proximal portion 415b to distal portion 416b, which in turn can enhance alignment of particles within the sample along the transverse plane 451b. As noted above with reference to FIG. 4A, the distal and proximal boundaries or portions of the transition zone may be curved or smooth, instead of angled.

Figures 1, 4D:
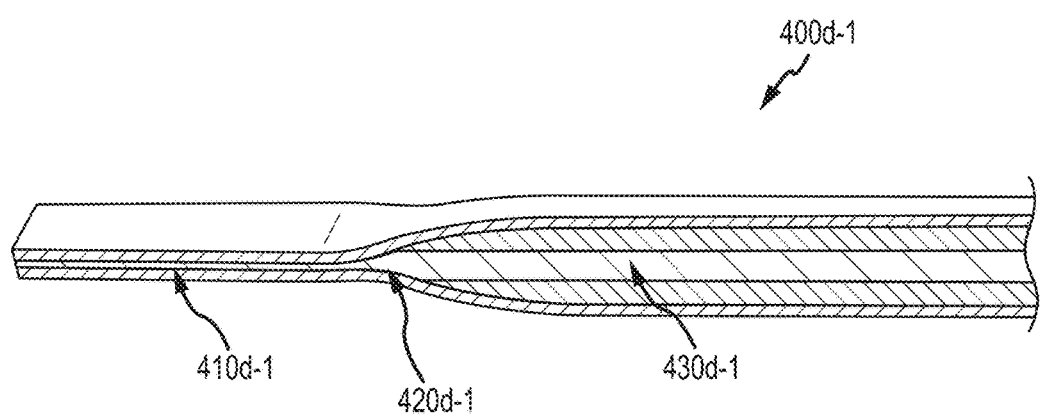

FIG. 4C depicts features of an exemplary cannula or sample feed tube 400c according to embodiments of the present invention, where the cannula has a length L. FIG. 4D depicts a longitudinal cross-section of cannula 400d. As shown here, the cannula 400d includes a distal flattened section 410d, a central tapered section 420d, and a proximal tubular portion 430d. As depicted in FIG. 4C-1, an exemplary cannula or sample feed tube 400c-1 can have a distal portion 410c-1 and a proximal portion 430c-1. In some cases, the distal portion 410c-1 has a length of about 1.359 mm and a width of about 1.43 mm. In some cases, the exit port of the distal end has an exit width W(E) of about 1.359 mm. According to some embodiments, a cannula may have an internal flowpath geometry that is different from what is depicted in FIGS. 4C and 4D. For example, as illustrated in FIG. 4D-1, the cannula 400d-1 does not include a tapered central section having an expanded flow area cross-section. As depicted in FIG. 4D-1, cannula 400d-1 has a distal section 410d-1, a central tapered section 420d-1 having a tapering inner diameter, and a proximal section 430d-1. Corresponding to the tapering inner diameter of central section 420d-1, the cross-sectional inner area of 410d-1 is smaller than the cross-sectional inner area of 430d-1.

FIG. 4E illustrates a transverse cross-section of a distal flattened section 410e. As shown here, the distal section 410e has an inner width W(I) and an inner height H(I), through which a sample stream flows. Further, the distal section 410e has an outer width W(O) and an outer height H(O). As depicted in FIGS. 4D and 4E taken in combination, the distal portion 410e of the sample fluid injection tube has an outlet port P having a height H(I) and a width W(I), where the height H(I) is less than the width W(I). According to some embodiments, the height H(I) of the outlet port P of distal portion 410e (or the inner height of the distal portion 410d) can have a value of about 150 µm. In some cases, the height H(I) can be within a range from about 50 µm to about 250 µm. According to some embodiments, the width W(I) of the outlet port P of distal portion 410e (or the inner width of the distal portion 410d) can have a value of about 1350 µm. In some cases, the width is about 1194 µm. In some cases, the width W(I) can have a value within a range from about 500 µm to about 3000 µm. In some cases, distal flattened section 410d can be manufactured by applying a clamping force to a tube or conduit.

FIG. 4F illustrates a transverse cross-section of a central tapered section 420f. As shown here, the central tapered section 420f has an inner diameter D(I) through which a sample stream flows. Further, the central tapered section 420f has an outer diameter D(O). FIG. 4G illustrates a transverse cross-section of a proximal section 430g. As shown here, the proximal section 430g has an inner diameter D(I) through which a sample stream flows. Further, the distal section 430g has an outer diameter D(O).

As depicted in FIG. 4D, the injection tube or cannula 400d can have a proximal portion 430d having a first flow cross-section area (e.g. $\pi^*(D/2)^2$ shown in FIG. 4G), a distal portion 410d having a second flow cross-section area (e.g. W(I)*H(I) shown in FIG. 4E) that is less than the first flow cross-section area, and a third portion 420d disposed between the proximal portion 430d and the distal portion 410d. The third portion 420d can have a third flow cross-section (e.g. $\pi^*(D/2)^2$ shown in FIG. 4F) that is larger than the first and second flow cross-sections. In some instance, the outer diameter D(O) of proximal portion 430g is about 1067 µm and the inner diameter D(I) of proximal portion 430g is about 813 µm.

Figure 4H:
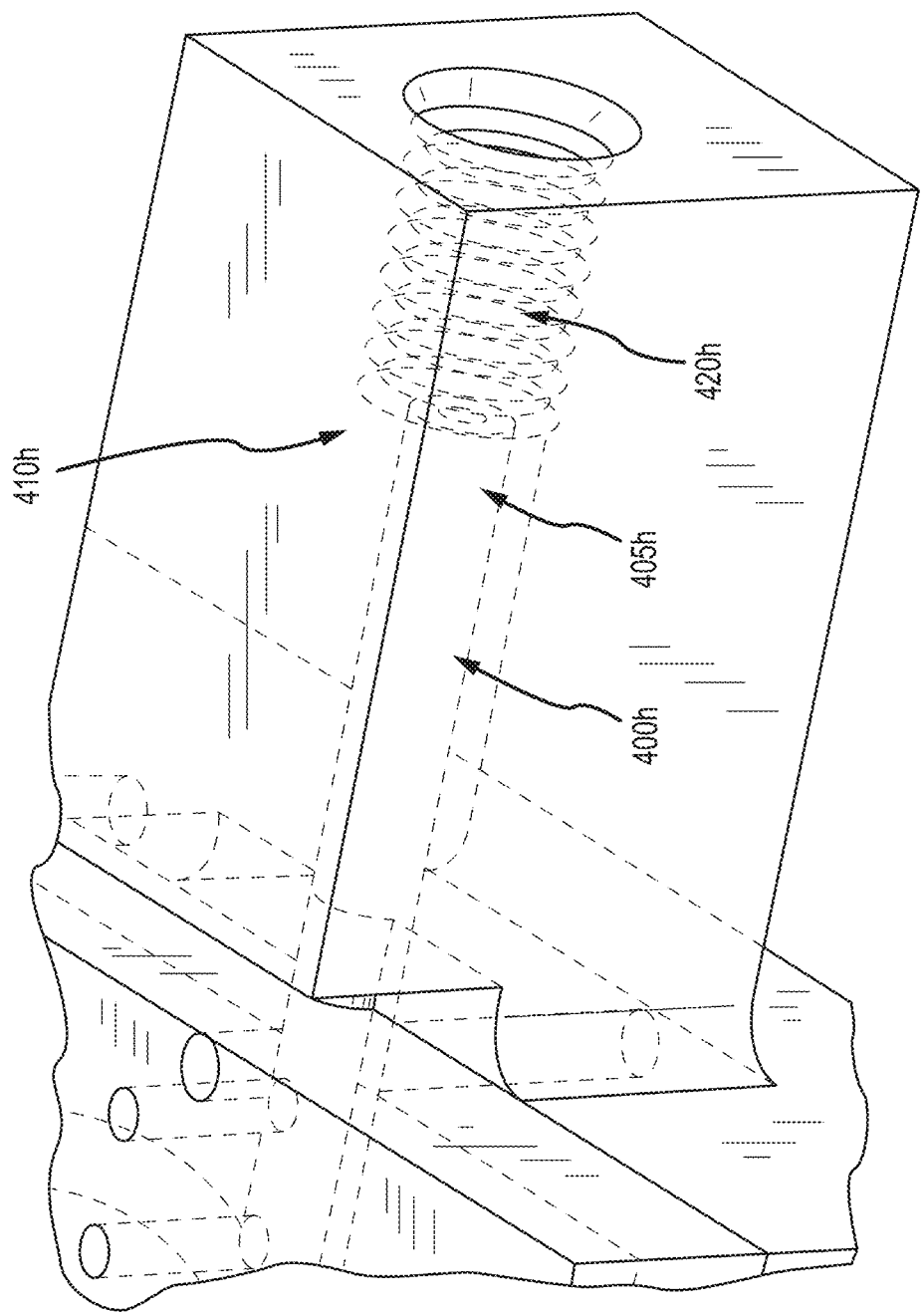
FIG. 4H depicts aspects of a flowcell according to embodiments of the present invention.

According to some embodiments, a proximal portion of an injection tube can be coupled with a sample port of a sample inlet fitting. For example, as shown in FIG. 4H, a proximal portion 405h of a cannula 400h can be coupled directly to a sample port 410h at an exit of a sample inlet fitting 420h.

Figure 4I:
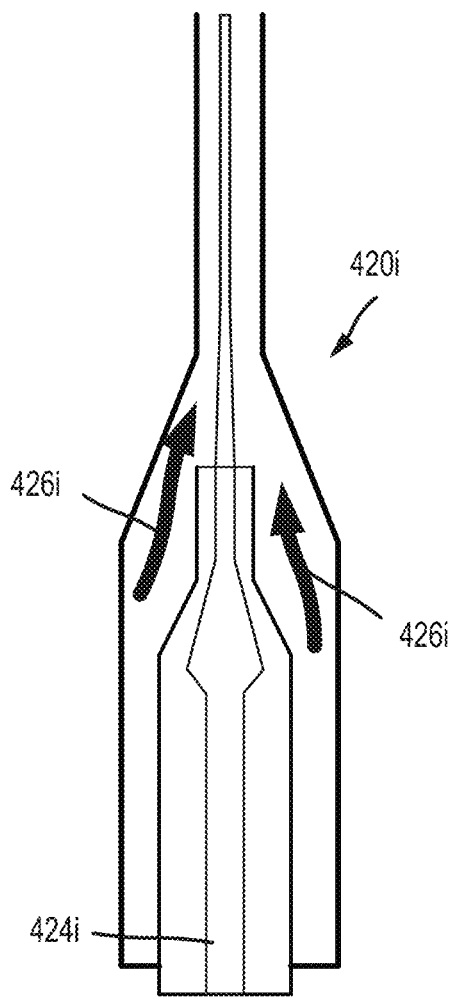
FIGS. 4I and 4J depicts aspects of fluid flow in a flowcell relative to gravity according to embodiments of the present invention.
Figure 4J:
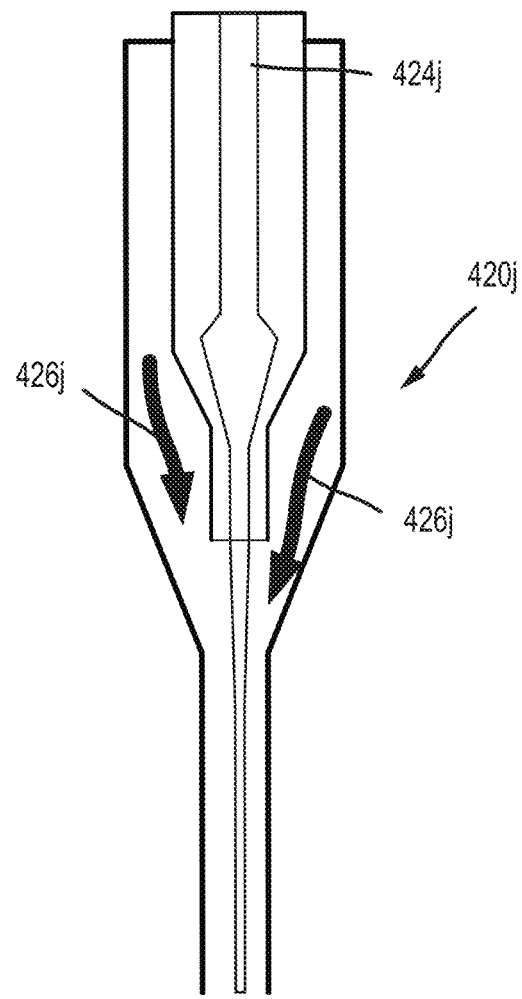
Figure 4K:
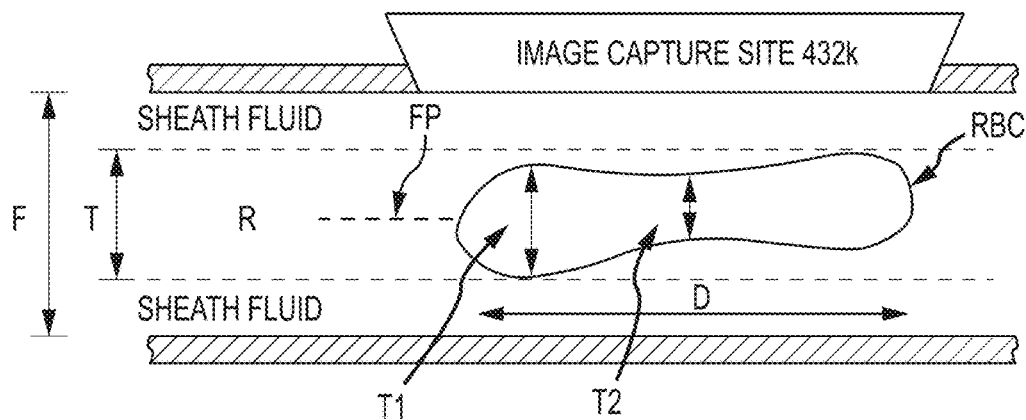
FIGS. 4K and 4L depict aspects of sheath fluid and sample flow within a flowcell at an image capture site, according to embodiments of the present invention.

A flowcell of a system for imaging particles in a blood fluid sample can be oriented at any desired angle or direction relative to the direction of the force of gravity. For example, a flowcell can be oriented in an upward direction, so that fluid flowing within the flowcell (e.g. sheath fluid, optionally in combination with sample fluid) can travel in an upward direction, against the force of gravity. Likewise, a flowcell can be oriented in an downward direction, so that fluid flowing within the flowcell (e.g. sheath fluid, optionally in combination with sample fluid) can travel in a downward direction, with the force of gravity. FIG. 4I depicts a flowcell 420i oriented in an upward direction, so that sample fluid 424i and sheath fluid 426i flowing within the flowcell 420i flow against gravity G. FIG. 4J depicts a flowcell 420j oriented in a downward direction, so that sample fluid 424j and sheath fluid 426j flowing within the flowcell 420j do not flow against gravity G, but rather flow with gravity G.

As shown in FIG. 4K, a sample stream ribbon R flowing through an image capture site 432k of a flowcell 420k can have a thickness T of about 2 µm. In some cases, thickness T of the sample stream ribbon can be up to about 3 µm. Typically, cells or particles that are smaller than the sample stream thickness will be contained within the ribbon. An exemplary red blood cell (RBC) can be present as a biconcave disk and can have a diameter D of between about 6.2 µm and about 8.2 µm. Further, an exemplary red blood cell can have a maximum thickness T1 of between about 2 µm and about 2.5 µm and a minimum thickness T2 of between about 0.8 µm and about 1 µm. In some cases, red blood cells can have a thickness of up to about 3 µm. Exemplary human platelets can vary in size, and can also have a thickness or diameter of about 2 µm. Although not shown to scale here, the flowcell can define a flow path thickness F having a value of about 150 µm, at the image capture site. In some cases, the flowpath thickness F has a value between 50 µm and 400 µm. This flowpath thickness F can also correspond to the distal height 418b of distal portion 461b depicted in FIGS. 4B-1 and 4B-2.

As shown in FIG. 4K, the ratio of the thickness T of the sample fluid stream to the thickness of the particle (red blood cell) is about 1:1. According so some embodiments, a ratio of the thickness T of the sample fluid stream at the image capture site to a size of one of the particles is within a range from 0.25 to 25. In some cases, the thickness T can have a value within a range from 0.5 µm to 5 µm.

As discussed elsewhere herein, as well as in co-pending U.S. patent application Ser. No. 14/215,834, filed Mar. 17, 2014, viscosity differences between fluid of the sample ribbon R and the sheath fluid can operate to align or orient particles in the sample stream, for example red blood cells, along the direction of the flow. When so aligned, as shown in FIG. 4K, the imaging device or camera can obtain images of the red blood cells such they appear round, because the major surface of the blood cell is facing toward the camera. In this way, the red blood cell assumes an alignment that presents a low resistance relative to the flow. Hence, the relative viscosity characteristics of the sheath fluid and the sample fluid can contribute to a high percentage or number of red blood cells facing toward the camera, thus enhancing the evaluation capability of the particle analysis system.

According to some embodiments, the viscosity characteristics of the sheath fluid operate to limit particle misalignment in the blood fluid sample. For example, viscosity differentials can be effective to limit red blood cells imaging orientation misalignment in the blood fluid sample to less than about 10%. That is, 90 or more red blood cells out of 100 red blood cells in a sample can be aligned so that their major surfaces face toward the imaging device. A symmetrical narrowing transition zone can provide a value of 20%. As discussed elsewhere herein, for example with reference to FIG. 4R, it is possible to compare alignment results obtained from an analyzer configuration that involves a symmetrical narrowing flowcell transition zone and a viscous sheath fluid to alignment results obtained from an analyzer configuration that involves a symmetrical narrowing flowcell transition zone without the use of a viscous sheath fluid. Use of a viscous sheath fluid can reduce the percentage of misaligned cells. According to some embodiments, the sheath fluid has an index of refraction similar to that of water (i.e. n=1.3330). In some cases, the sheath fluid has a water content of about 89%. In addition to alignment effects observed as a result of the viscosity differential, alignment effects are also observed as a result of a bilateral tapered transition zone. In some cases, it is observed that a bilateral (i.e. symmetrical) tapered transition zone is twice as effective at aligning particles as compared to an asymmetric tapered transition zone design.

Efficient alignment of the red blood cells can contribute to improved diagnosis. In some cases, the shape of the imaged red blood cells can be used to determine whether a patient from whom the sample is obtained has a particular physiological condition or disease. For example, patients with sickle cell disease present with blood cells having an abnormal shape (i.e. in the shape of a sickle). Hence, by obtaining high quality images of aligned red blood cells, it is possible to ensure an accurate diagnosis. Other shape variations in red blood cells, for example red blood cells having thin peripheral area and a large flat central area, whereby the red blood cell appears to have the profile of a bicycle tire, can effectively be imaged using the instant alignment techniques. Similarly, red blood cells having a small central portion, and a thick peripheral area, whereby the red blood cell appears to have the profile of a truck tire, can be imaged for diagnostic purposes. The improved imaging techniques disclosed herein are also useful for evaluating other red blood cell characteristics, such as hemoglobin content, iron content, and the like.

Without being bound by any particular theory, it is believed that a high viscosity differential between the viscosity of the sheath fluid and the viscosity of the sample fluid produces a modified parabolic profile, wherein the profile is generally parabolic and has a central bump corresponding to a center area of the flow where the acceleration is increased, and the central bump contributes to alignment of sample particles or intraparticle organelles. According to some embodiments, the velocity difference between the sheath and sample ribbon and the viscosity difference generate shear forces to increase alignment of the organelles or intracellular particles. Exemplary aspects of the sheath fluid parabolic profile are discussed in co-pending U.S. patent application Ser. No. 14,215,834, filed Mar. 17, 2014, the content of which is incorporated herein by reference.

Figure 4L:
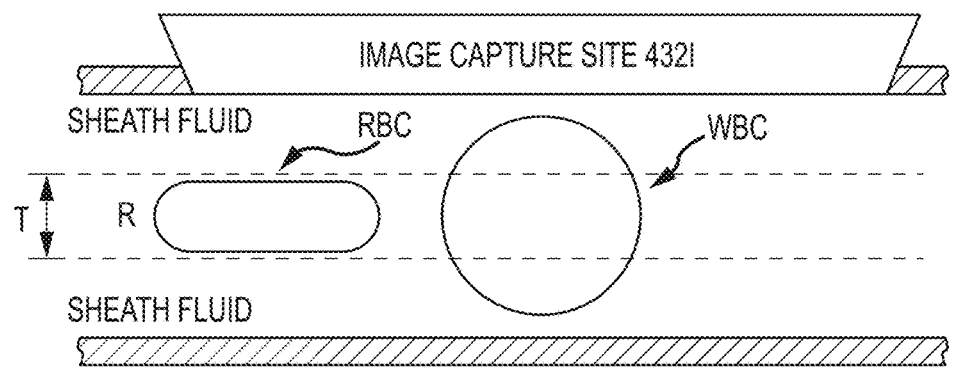
Figures 1, 4L:
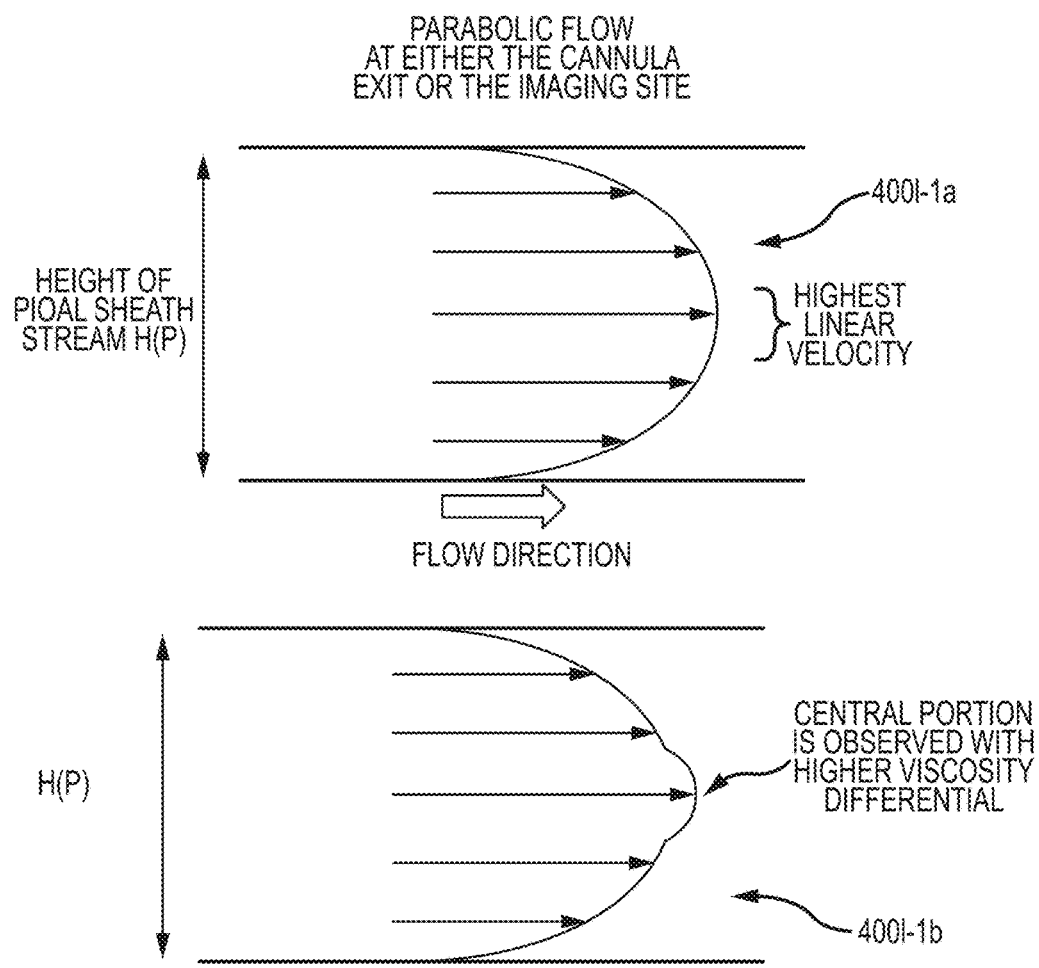

White blood cells are typically larger than red blood cells and platelets. For example, exemplary neutrophils and eosinophils can have a diameter of between about 10 µm and about 12 µm. Exemplary basophils can have a diameter of between about 12 µm and about 15 µm. Exemplary lymphocytes (small) can have a diameter of between about 7 µm and about 8 µm, and exemplary lymphocytes (large) can have a diameter of between about 12 µm and about 15 µm. Exemplary monocytes can have a diameter of between about 12 µm and about 20 µm. The configuration of the particle analysis system, including interaction between the sheath fluid and the fluid sample ribbon as they pass through the flowcell, can operate to compress white blood cells as they travel through the image capture site 432l, as indicated in FIG. 4L. Hence, for example, a central portion of the white blood cell (WBC) can be positioned within the sample fluid ribbon R, and peripheral portions of the white blood cell can be positioned within the sheath fluid. Hence, as the white blood cell is transported through the flowcell by the ribbon, the sides of the white blood cell can extend into the sheath fluid. The numerical values or ranges for the thickness T of sample stream ribbon R, and the thickness F of the flowpath as discussed above with regard to FIG. 4K are similarly applicable to FIG. 4L.

According to some embodiments, viscosity differences between the sheath fluid and the sample fluid can operate to align organelles or other intracellular features which are present within cells such as white blood cells. Without being bound by any particular theory, it is believed that shear forces associated with the viscosity differential between the sheath fluid and the sample fluid may act upon the white blood cells so as to align the intracellular features. In some cases, shear forces associated with velocity differentials between the sheath fluid and sample fluid may contribute to such alignment. These alignment effects may be impacted by a size differential between the particles and the sample fluid ribbon as well. For example, where portions of the particles extend out of the sample fluid ribbon and into the surrounding sheath fluid, shear forces associated with the difference in viscosity may have a pronounced effect on the intracellular feature alignment.

With reference to FIGS. 4K and 4L, in some instances portions of the cell or particle may extend out of the thin sample fluid ribbon R and into the surrounding sheath fluid. As discussed in co-pending U.S. patent application Ser. No. 14/215,834, filed Mar. 17, 2014, the sheath fluid may contain cellular protectants that inhibit or prevent the sheath fluid from disrupting or lysing the cells or particles. For example, the sheath fluid may contain cellular protectants that preserve the structural integrity of the cells walls as the cells are exposed to the chemical environment of the sheath fluid. Similarly, the cellular protectants may also operate to preserve the structural integrity of the cells walls as the cells experience any shear forces induced by flowcell geometry, and a difference in velocity and/or viscosity between the sample fluid and the sheath fluid. Relatedly, the protectorants can protect the cells or particles from forces resulting from the difference in velocity between the sample fluid and sheath fluid. In this way, the cells retain their viability as they reach the image capture site.

The shear forces can be significant at the interface between the sample fluid ribbon and the sheath fluid envelope. According to some embodiments, flow within the flowcell flowpath can be characterized by a parabolic flow profile. FIG. 4L-1 depicts exemplary aspects of parabolic flow profiles 4001-1a and 4001-1b. The parabolic profile 4001-1a in the upper panel is a typical velocity profile found in flows within certain flowcell embodiments of the present invention (e.g. where there is little or no viscosity differential between a sample fluid flowstream that is enveloped within a sheath fluid flowstream). As can be seen, a highest linear velocity is observed in the middle of the fluid stream and slower linear velocities are observed near the flowcell wall. Profile 4001-1a can also be observed in fluid stream with a slight viscosity difference between the sheath and sample fluids. In a case where there is a high viscosity differential between the sheath and fluid streams, a central bump is observed as shown in profile 4001-1b, where there is a localized central area with amplified linear velocities. According to some embodiments, particles that are sufficiently large in size will be subjected to some amount of shear force, even where such particles are fully contained within a single fluid phase (i.e. either within the sheath fluid envelope, or alternatively within the sample fluid ribbon).

In some instances, the velocity of the sheath fluid may be different from the velocity of the sample fluid. For example, the sheath fluid may be traveling at 80 mm/second and the sample fluid may be traveling at 60 mm/second. Hence, in some instances, the sample fluid exits the distal cannula port at a sample fluid speed that is slower than the sheath fluid speed of the surrounding envelope. Hence, the sheath fluid can operate to drag the sample fluid along the flowpath of the cannula, thus accelerating the sample fluid and reducing the thickness of the sample fluid ribbon. The sample fluid ribbon maintains the overall volume and mass, so as it travels faster it becomes thinner. According to some embodiments, both the sheath fluid and the sample fluid have a velocity of between about 20 and 200 mm/second at the image capture site.

Typically, the velocity of the sample fluid increases as the sample fluid travels from the cannula exit port to the image capture site. In some instances, the velocity of the sample fluid at the image capture site is 40 times the velocity of the sample fluid as it exits the cannula port at the cannula distal portion. According to some embodiments, the decrease in cross sectional area of the sample ribbon is linear to the increase in velocity. According to some embodiments, if the sheath velocity at the cannula exit is higher than the sample ribbon velocity this will also increase the final sample ribbon velocity at the imaging area.

The sheath fluid can operate to apply significant shear forces on the sample fluid ribbon and on particles within the sample fluid ribbon. Some forces are parallel to the direction of flow, and particles may also encounter forces which are perpendicular to the direction of flow. Often, as the sheath fluid and sample fluid approach the image capture site or zone, the sheath and sample fluids are traveling at or near the same velocity. Hence, the boundary or interface between the sheath and sample fluids as they pass the image capture site may present lower shear forces, as compared to the boundary or interface at the distal cannula exit port or at the tapered transition zone. For example, at the tapered transition zone, the boundary or interface between the sheath fluid envelope and sample fluid ribbon can be in transition, such that the sample ribbon which is initially slower and thicker becomes faster and thinner, and particles in the sample fluid become more aligned. Put another way, the shear forces may be prominent at the tapered transition zone, and can dissipate toward the image capture site. The shear forces at the image capture site can be represented by a parabolic profile, and can be much lower than the shear forces at the tapered transition zone. Hence, cells or particles can experience higher shear forces as they pass through the transition zone, and lower shear forces as they pass through the image capture site. According to some embodiments, the viscosity difference between the sheath and sample fluids can bring the red blood cells into alignment and thereby into focus. According to some embodiments, the viscosity difference between the sheath and sample fluids can bring white blood cell organelles into alignment and thereby into focus. Relatedly, enhanced imaging results can be obtained for cellular and organelle components that are aligned and brought into focus, resulting from the geometric narrowing of the stream and the velocity difference between the sheath and sample fluids.

Figure 4M:
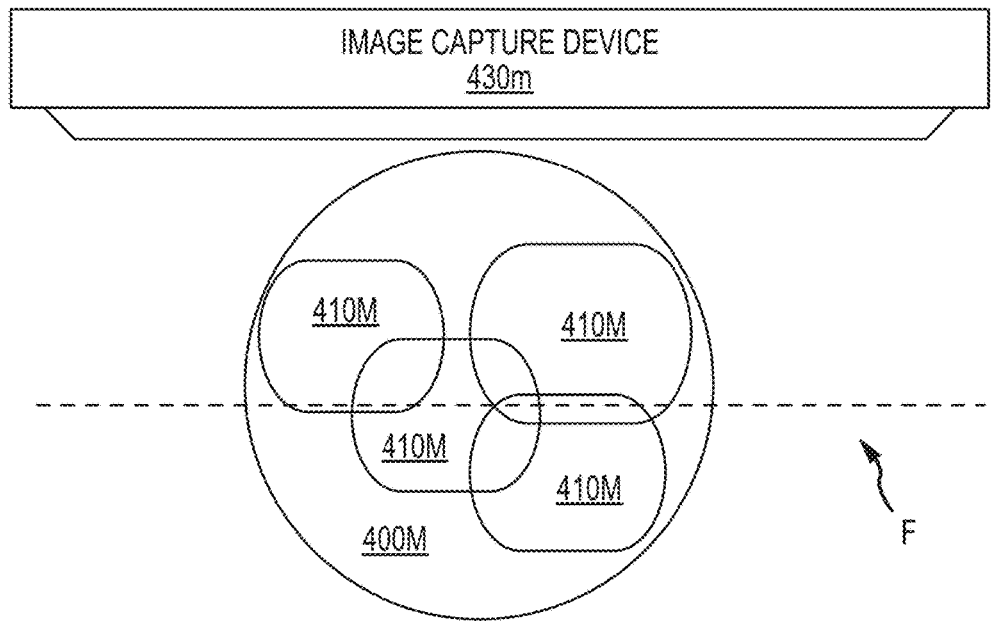
FIGS. 4M and 4N depict aspects of intracellular alignment and imaging, according to embodiments of the present invention.
Figure 4N:
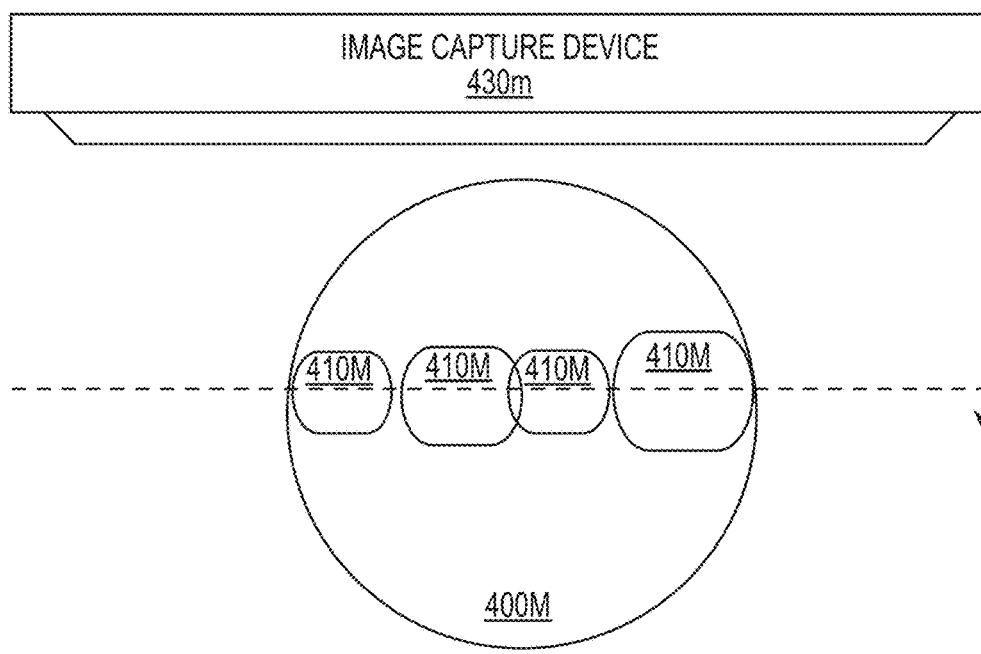

FIG. 4M depicts an exemplary neutrophil 400m (a type of white blood cell) having internal organelles such as lobes 410m. As a result of the viscosity differential between the sample fluid and the sheath fluid, the internal organelles can align within the cell, as indicated by FIG. 4N. Hence, the intracellular organelles can be effectively imaged with an image capture device 430*m*, without the organelles overlapping one another. That is, instead of the lobes being stacked upon one another as depicted in FIG. 4M, when viewed from the imaging or optical axis of the image capture device the lobes are aligned and sitting side by side as depicted in FIG. 4N. Hence, the lobes can be visualized in the captured imaged more effectively. The internal organelle alignment is a surprising and unexpected result of the viscosity differential between the sample and sheath fluids.

Any of a variety of hematology or blood particle analysis techniques can be performed using images of sample fluid flowing through the flowcell. Often, image analysis can involve determining certain cell or particle parameters, or measuring, detecting, or evaluating certain cell or particle features. For example, image analysis can involve evaluating cell or particle size, cell nucleus features, cell cytoplasm features, intracellular organelle features, and the like. Relatedly, analysis techniques can encompass certain counting or classification methods or diagnostic tests, including white blood cell (WBC) differentials. In some cases, images obtained using the flowcell can support a 5-part WBC differential test. In some cases, images obtained using the flowcell can support a 9-part WBC differential test. Relatedly, with reference to FIG. 4, the processor 440 can include or be in operative association with a storage medium having a computer application that, when executed by the processor, is configured to cause the system 400 to differentiate different types of cells based on images obtained from the image capture device. For example, diagnostic or testing techniques can be used to differentiate various cells (e.g. neutrophils, lymphocytes, monocytes, eosinophils, basophils, metamyelocytes, myelocytes, pro-myelocytes, and blasts).

Figure 4O:
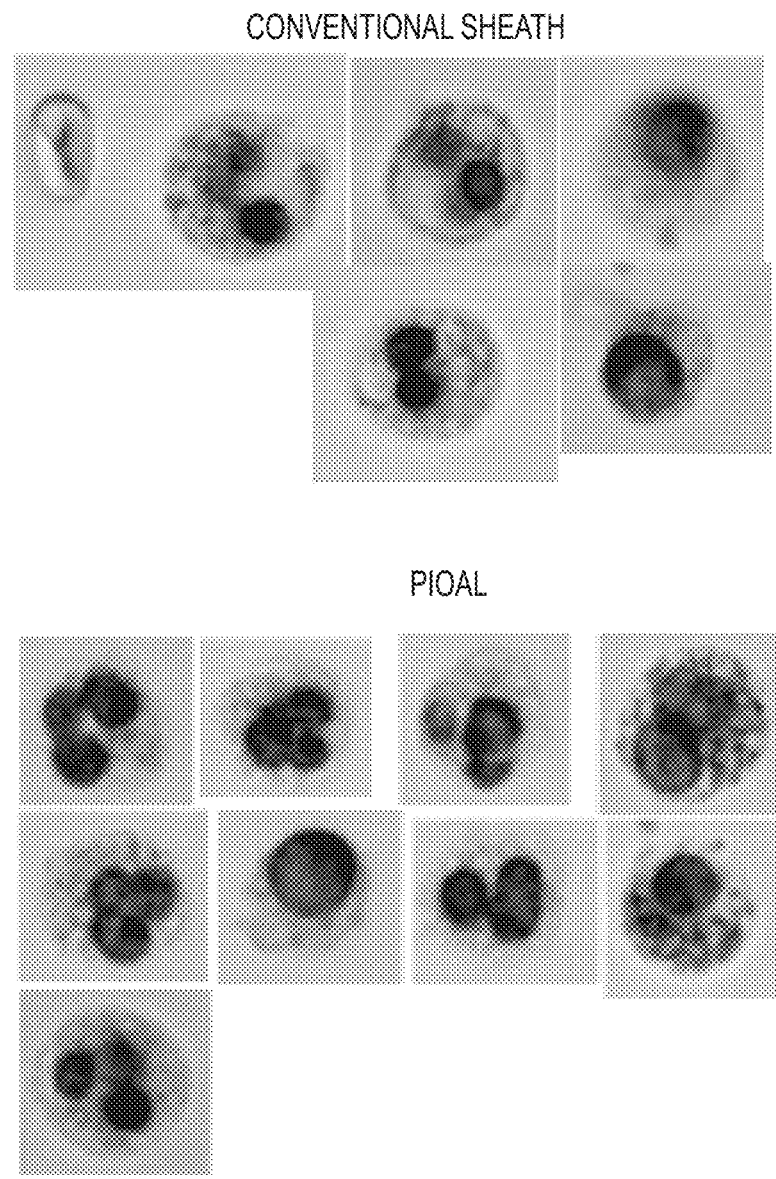
FIG. 4O depicts aspects of the effect of PIOAL on particle and/or intracellular particle alignment and imaging according to embodiments of the present invention. In this comparison of images obtained using PIOAL versus images obtained using a non PIOAL sheath fluid, it can be seen that use of the PIOAL resulted in more in-focus cellular contents such as lobes, cytoplasm, and/or granule.

FIG. 4O shows a comparison of images obtained using PIOAL versus images obtained using a non PIOAL sheath fluid. Use of the PIOAL resulted in more in-focus cellular contents such as lobes, cytoplasm, and/or granule. In this example, a PIOAL comprising a viscosity agent (about 30% glycerol) was used to process the sample. The pH was adjusted to a pH of about 6.8 to 7.2 and the sample mixture was made isotonic by (0.9% sodium chloride). The results shown here demonstrate the efficacy of an exemplary PIOAL used on an image analyzer to align cells and intracellular organelles.

Figure 4P:
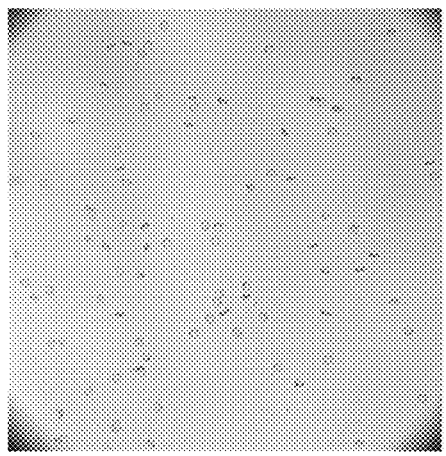
FIGS. 4P and 4Q show comparison of images obtained using PIOAL versus images obtained using standard sheath fluid. It can be seen that use of PIOAL resulted in an improved RBC alignment.
Figure 4P:
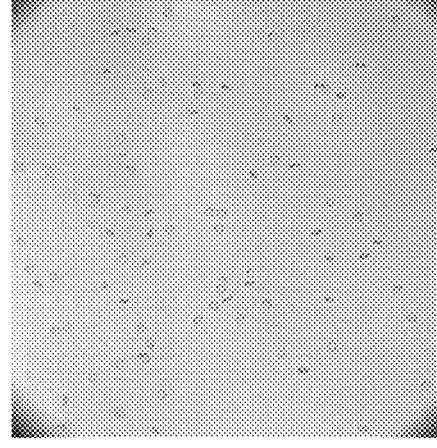
Figure 4P:
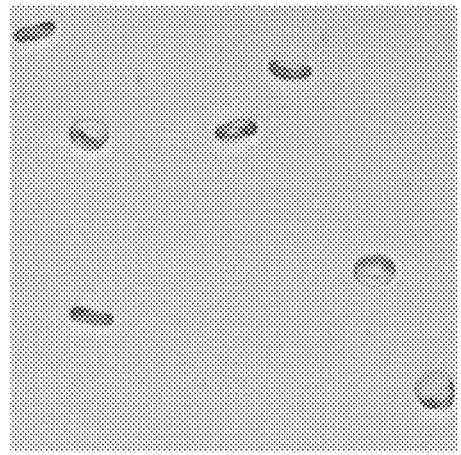
Figure 4Q:
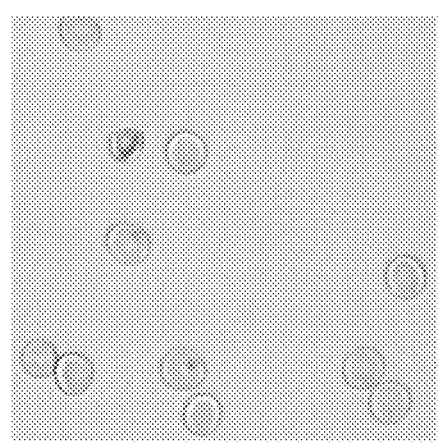

FIGS. 4P and 4Q show a comparison of images obtained using a standard sheath fluid (FIG. P upper and lower panels) versus images obtained using an exemplary PIOAL fluid (FIG. 4Q upper and lower panels). As shown here, the use of PIOAL resulted in an improved RBC alignment. The sample was analyzed using an instrument focusing protocol (on an exemplary target 44 as depicted in FIG. 1) and the target was brought into focus by a visual analyzer. The focusing system was then offset by displacement distance 52, resulting in the particles in the ribbon-shaped sample stream being in focus. The blood sample was previously diluted using a sample diluent. The sample flowed through a cannula and along a flowpath of a flowcell, thereby generating a ribbon-shaped sample stream (e.g. 2 microns in thickness) which was between two layers of PIOAL or standard sheath (in controls). The visual analyzer then generates focused images of the particles in the ribbon-shaped sample stream (e.g. at about 60 frames per second) to be used for analysis. The blood sample is obtained from a subject and processed for analysis by the blood analyzer. Images of RBCs in a flowcell are captured while the sample is processed using a standard sheath fluid or a PIOAL. Relative percentages demonstrate significant improvement in the number of aligned RBCs based on imaging data (e.g. 4P and 4Q). The result demonstrated that PIOAL was efficacious at increasing the percentage of RBC alignment while in flow in the ribbon-shaped sample stream using the focusing instrument/protocols as described herein.

It was also observed that the implementation of PIOAL results in improved alignment based on using increasing levels of glycerol (gly) in symmetric and asymmetric flowcells.

Figure 4R:
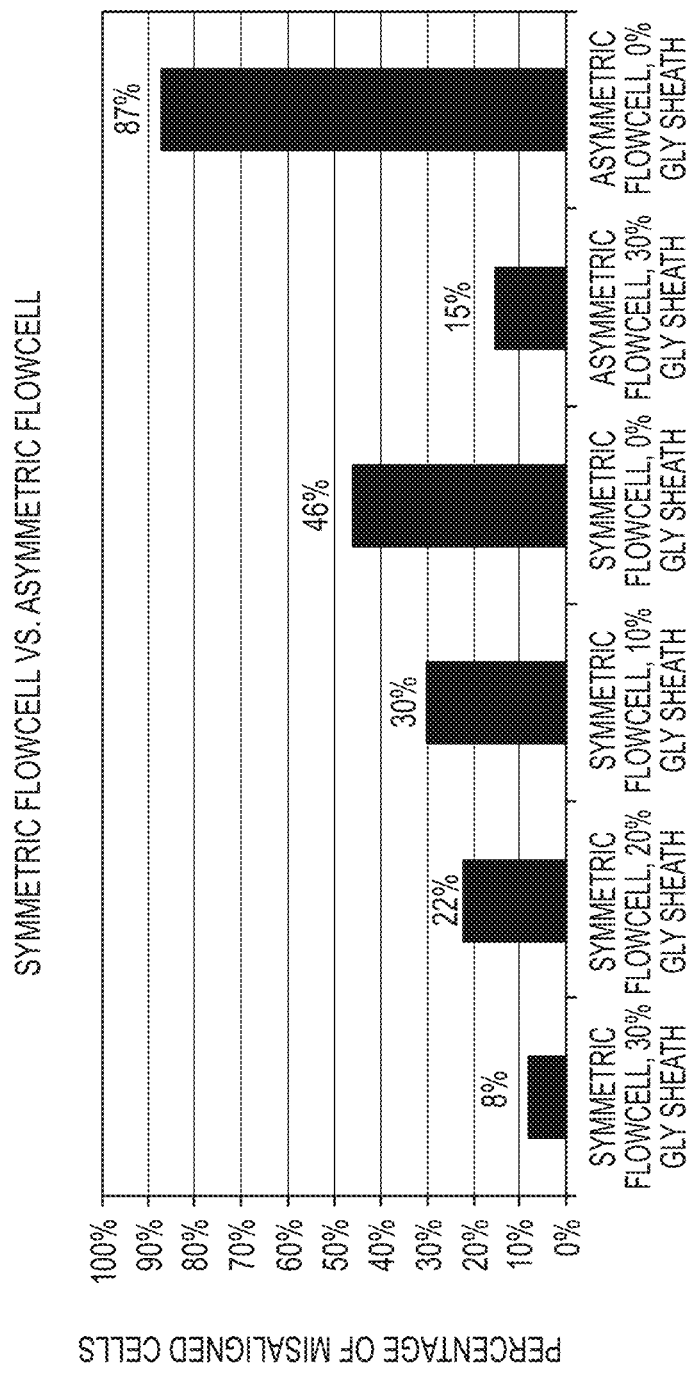
FIG. 4R illustrates certain particle alignment results obtains using flowcell configurations and sheath fluid compositions according to embodiments of the present invention.

The chart in FIG. 4R shows the percentage of non-aligned cells obtained using 0%-30% glycerol in the PIOAL with symmetric vs. asymmetric flow cells. Using 30% glycerol in the PIOAL and a symmetric flowcell results in reducing the percentage of misaligned cells to only 8%. Note without glycerol in the PIOAL, and with an asymmetric cell, the percentage of misaligned cells increased to 87%. Hence, this chart demonstrates the effect of glycerol percentage and flowcell geometry on particle (e.g. RBC) alignment. The addition of glycerol decreases the percentage of misaligned RBC cells using either symmetric or asymmetric flowcell geometry. The % non-aligned RBCs was reduced from 87% down to 15% in the asymmetric and 46% to 8% in symmetrical cells. Thus, the chart provides a comparison between misalignment results (8%) obtained from an analyzer configuration that involves a symmetrical narrowing flowcell transition zone and a viscous sheath fluid and misalignment results (46%) obtained from an analyzer configuration that involves a symmetrical narrowing flowcell transition zone without the use of a viscous sheath fluid.

These results provide evidence for the surprising and unexpected discovery that certain PIOAL compositions have unexpected properties aligning cells and re-positioning intracellular structures when used to perform image-based particle/cell analysis.

By way of example, several exemplary PIOAL formulations and methods of use thereof were developed. The following are some exemplars of PIOAL formulations with the desired properties. The PIOAL comprises a diluent and at least one viscosity modifying agent.

Exemplary PIOAL formulation A includes a 30% (v/v) glycerol solution having 300 mL glycerol and QS (quantity sufficient or to bring the final volume up to) to 1 L with diluent containing 9.84 g sodium sulfate, 4.07 g sodium chloride, 0.11 g Procaine HCl, 0.68 g potassium phosphate monobasic, 0.71 g sodium phosphate dibasic, and 1.86 g disodium EDTA. The initial mixture was followed by QS to 1 L with deionized water while adjusting pH to 7.2 with sodium hydroxide.

Exemplary PIOAL formulation B includes a 6.5% (v/v) glycerol solution having 65 mL glycerol and QS to 1 L with suitable exemplary diluent containing 9.84 g sodium sulfate, 4.07 g sodium chloride, 0.11 g Procaine HCl, 0.68 g potassium phosphate monobasic, 0.71 g sodium phosphate dibasic, and 1.86 g disodium EDTA. The initial mixture was followed by QS to 1 L with deionized water while adjusting pH to 7.2 with sodium hydroxide.

Exemplary PIOAL formulation C includes a 5% glycerol (v/v) solution with 1% PVP (w/v) in buffer having 50 mL glycerol, 10 g PVP (MW: 360,000), 1 packet of Sigma PBS powder, at pH 7.4 (0.01M phosphate buffered saline; 0.138M sodium chloride; 0.0027M potassium chloride), and QS to 1 L with deionized water.

Exemplary PIOAL formulation D includes a 1.6% PVP (w/v) solution having 16 g PVP (MW: 360,000) and 1 packet of Sigma PBS powder, at pH 7.4 (0.01M phosphate buffered saline; 0.138M sodium chloride; 0.0027M potassium chloride), and QS to 1 L with deionized water.

Throughput

Figure 5:
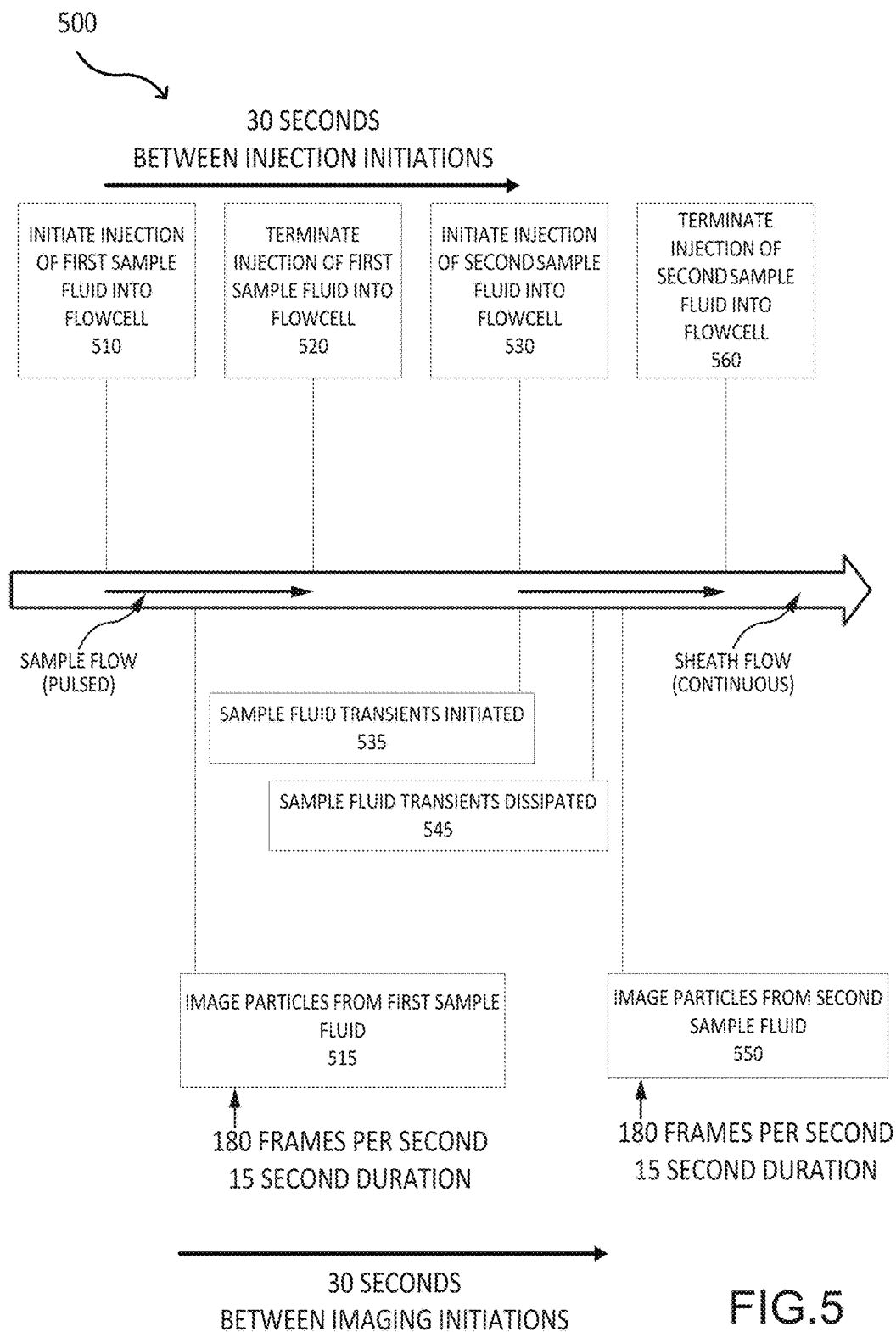
FIG. 5 depicts aspects of particle imaging methods according to embodiments of the present invention.

FIG. 5 depicts a timeline 500 corresponding to the injection of one or more sample fluids in a flowcell. As shown here, injection of a first sample fluid can be initiated into a flowcell, as indicated by step 510. Thereafter, particles from the first sample fluid can be imaged in the flowcell, as indicated by step 515. According to some embodiments, the first sample fluid can have a volume in a range from about 5 μL to about 150 μL. In some cases, the flow is 0.232 μL/sec (or within a range from 0.2 μL/sec to 0.35 μL/sec) at the imaging area. The injection of the first sample fluid can be terminated, as indicated by step 520, and injection of a second sample fluid can be initiated into the flowcell, as indicated by step 530. Sample fluid transients can be initiated, as indicated by step 535, as a result of termination of the first sample fluid injection and initiation of the second sample fluid injection. Subsequently, sample fluid transients in the flowcell can dissipate, as indicated by step 445. Particles from the second sample fluid can be imaged in the flowcell, as indicated by step 550. The injection of the second sample fluid can be terminated, as indicated by step 560. In some instances, the injection and flow procedures are performed at temperatures within a range from about 18° C. to about 40° C.

Typically, the stream of the sheath fluid remains flowing within the flowcell as the sample is injected, and as the injection is terminated. Hence, according to some embodiments, a continuous flow of sheath fluid is maintained while injections of sample fluid are pulsed into the flowing sheath. The continuous flow of the sheath fluid can contribute to preservation of a ribbon shape in the sample fluid as the sample fluid flows along the flowcell.

According to some embodiments, the image capture associated with step 550 can be performed within four seconds of the image capture associated with step 515. According to some embodiments, the time between first and second sample fluid injections (e.g. between steps 510 and 530) is about 30 seconds. Relatedly, according to some embodiments, the time between initiation of imaging of the first and second sample fluids (e.g. between initiation of step 515 and initiation of step 550) is about 30 seconds. In this way, it is possible to process 120 sample fluids per hour. In some cases, an image capture device operates at a frame rate of 180 frames per second (FPS), thus producing multiple unique consecutive images or frames at a high frequency or rate. As shown here, the duration of an imaging step (e.g. 515 or 550) can be 15 seconds, thus producing 2,700 images per sample fluid.

In some instances, the first sample fluid reaches a stabilized state within about 1 to 3 seconds following injection (e.g. step 510) of the first sample fluid from the sample fluid injection tube into the flowing sheath fluid. In some instances, the first sample fluid reaches a stabilized state within less than 1 second following injection (e.g. step 510) of the first sample fluid from the sample fluid injection tube into the flowing sheath fluid. The injection of the sample into the flowcell can be a two-step process. According to this embodiment, the first step is a high speed push that clears all the diluent out of the cannula, and after the initial push the flow rate of the sample is reduced significantly. The transition time can be defined as the time it takes the sample (e.g. a cell) to travel from the cannula exit to the imaging area under the imaging flow conditions (slower sample flow rate). In some cases, it can take about 4 seconds for the sample fluid to travel from the cannula exit to the imaging area. In some instances, the first sample fluid reaches a stabilized state within about 1.8 seconds from injection (e.g. step 510) of the first sample fluid from the sample fluid injection tube into the flowing sheath fluid. In some instances, the sample fluid has a transit time through the flowcell (e.g. from an cannula exit port to an image capture site) within a range from about 2 to 4 seconds. In some cases, the sample fluid has a transit time through the flowcell within a range from about 1 to 4 seconds.

According to some embodiments, it takes between about 2 and about 5 seconds for the flow to stabilize, or to travel from a distal exit port of the cannula to the imaging area. In some cases, an image capture duration period can be about 20 seconds.

A hematology system according to embodiments of the present invention can process a blood sample having a volume of about 150 μL. The aspirated blood volume can be about 120-150 μL. In some cases, the minimum available blood volume in the sample tube is about 500 μL for an automatic sampling mode and about 250 μL for manual sampling mode. The cannula or injection tube 400d shown in FIG. 4D has an internal volume of about 13 uL. According to some embodiments, the cannula or injection tube has an internal volume of less than about 30 uL. The volume of blood sample is effective to flush the cannula before starting image collection, and thus can avoid extended periods of time where the sample flow is not stable. For example, use of a cannula having an internal volume of about 13 uL can correspond to a sample flow instability period of about 2 to 3 seconds. According to some embodiments, the cannula internal volume may not impact sample flow stability. According to some embodiments, the cannula internal volume may impact the cell concentration stability in the sample ribbon itself if the initial high speed sample push is insufficient to replace all diluent inside the cannula. Relatedly, the cannula can be cleaned in between samples in a short amount of time using a small amount of diluent. In this way, it is possible to achieve a stable sample flow which facilitates the capture of a high quality image, and at the same time achieve a high throughput, with a low carry-over. According to some embodiments, a cannula with a high internal volume may require a high volume initial high speed push of sample to clear out all diluent in the lines and cannula. Embodiments of the present invention encompass the implementation of lower internal cannula volumes, which are suitable for hematological applications where the available sample volumes are low, and where a lower volume push can be accomplished in a shorter amount of time.

According to some embodiments, hematology systems can be configured to limit transients and sequential sample cross-contamination so as to speed image acquisition from blood fluid samples.

Methods

Figure 6:
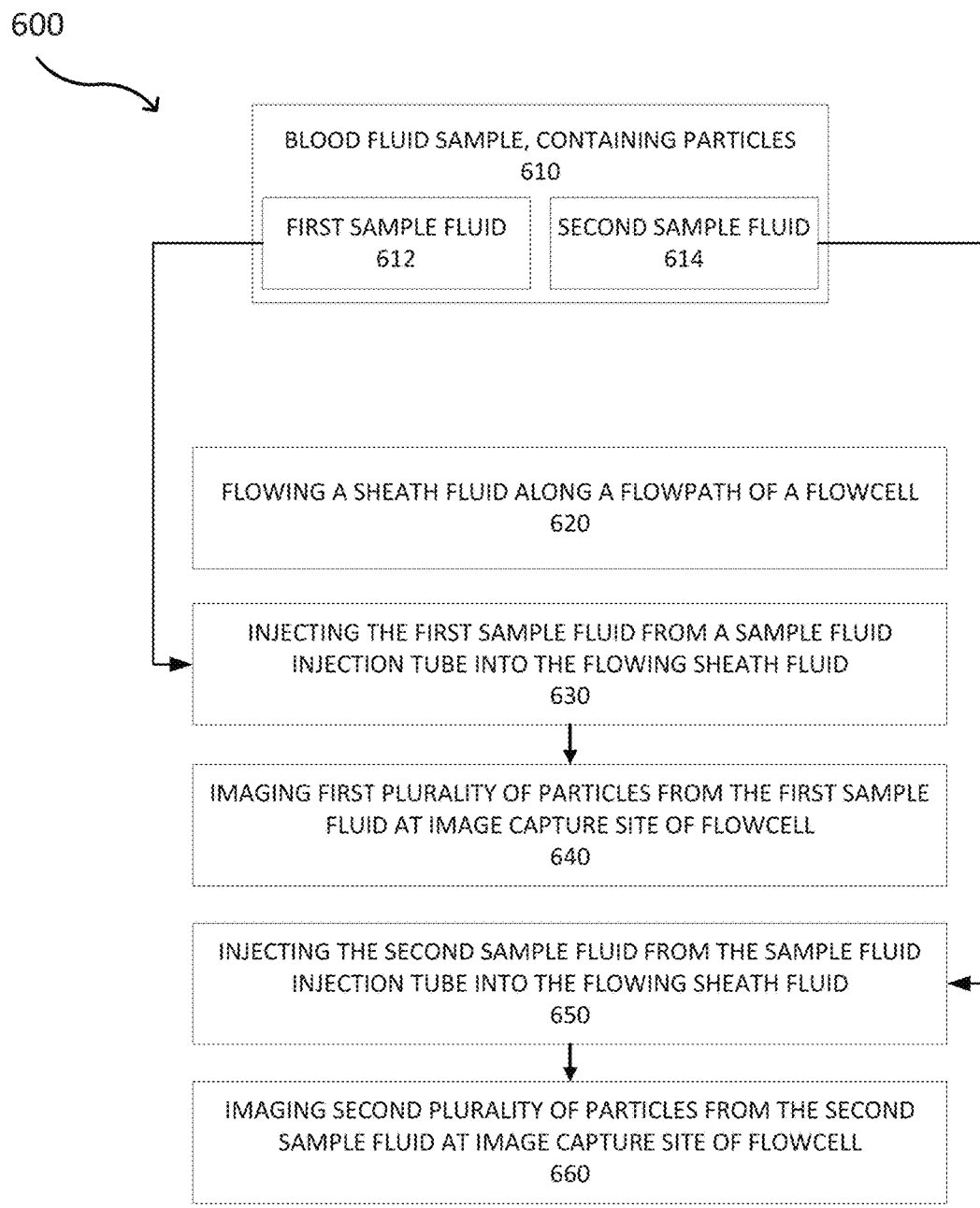
FIG. 6 depicts aspects of particle imaging methods according to embodiments of the present invention.

FIG. 6 depicts aspects of an exemplary method 600 for imaging particles in a blood fluid sample, according to embodiments of the present invention. As shown here, the blood sample 610 includes particles, and can be portioned into one or more sample fluids, such as a first sample fluid 612 containing particles and a second sample fluid 614 containing particles. The method can include flowing a sheath fluid along a flowpath of a flowcell, as indicated by step 620. Further, the method can include injecting the first sample fluid 612 from a sample fluid injection tube into the flowing sheath fluid within the flowcell, as indicated by step 630, so as to provide a sample fluid stream having a first thickness adjacent the injection tube. The flowpath of the flowcell can have a decrease in flowpath size, such that a thickness of the sample fluid stream decreases from the initial thickness to a second thickness adjacent an image capture site. The method 600 may further include imaging a first plurality of the particles from the first sample fluid at the image capture site of the flowcell, as indicated by step 640.

The method 600 can also include initiating sample fluid transients. For example, sample fluid transients can be initiated by terminating injection of the first sample fluid into the flowing sheath fluid, and injecting the second sample fluid into the flowing sheath fluid as indicated by step 650. Further, the method 600 can include imaging a second plurality of the particles from the second sample fluid at the image capture site of the flowcell, as indicated by step 660. According to some embodiments, the imaging of the second plurality of particles can be performed substantially after the sample fluid transients and within 4 seconds of the imaging of the first plurality the particles.

Shear Strain Rate

Figure 7:
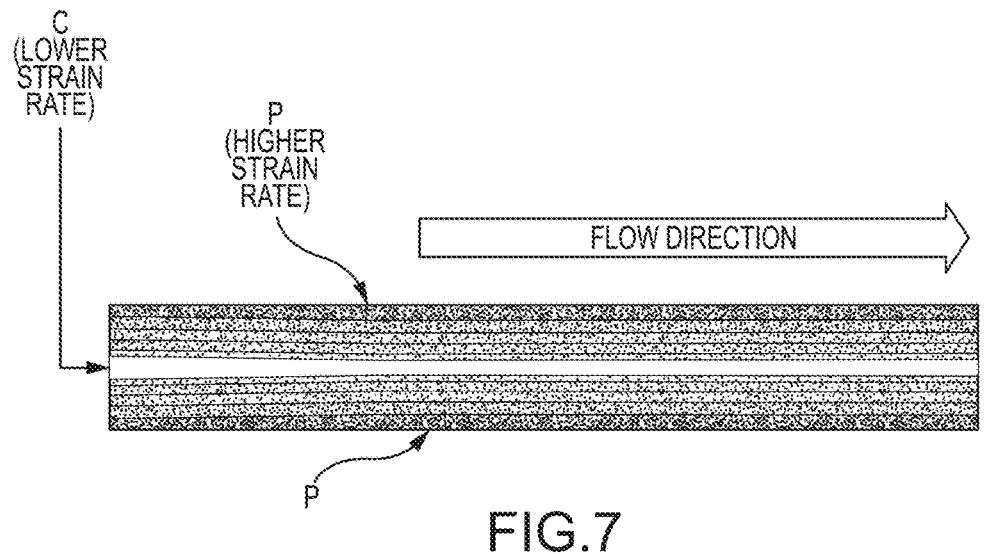
FIGS. 7 and 8 depict aspects of flowstream strain rate according to embodiments of the present invention.
Figure 8:
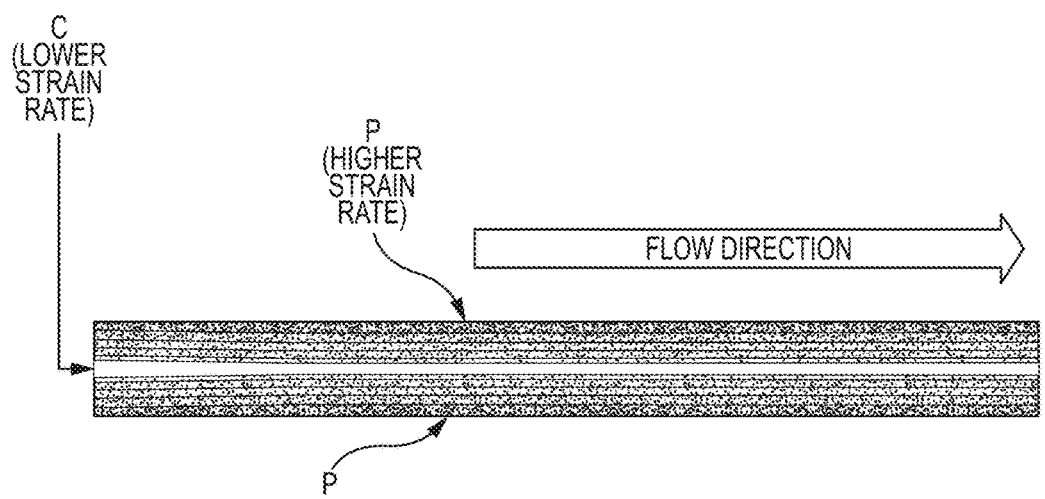

FIGS. 7 and 8 depict aspects of shear strain rate values for certain flow conditions in a flowcell according to embodiments of the present invention. In each of these drawings, a 30% glycerol sheath fluid is used. In some cases, the viscosity can have a value of $2.45 \times 10^{-3}$. A shear stress value can be equal to the product obtained by multiplying a viscosity value with a strain rate value. With regard to FIG. 7, the sample can have a flow rate of 0.3 μL/sec and the sheath fluid can have a flow rate of 21 μL/sec. With regard to FIG. 8, the sample can have a flow rate of 1 μL/sec and the sheath fluid can have a flow rate of 70 μL/sec. In each of these figures, it can be seen that the flow presents a lower strain value toward the center (C) and a higher strain value toward the periphery (P). Such strain values can correspond to an asymmetric flowcell configuration, in some embodiments.

As depicted in FIG. 7, according to some embodiments, the lower strain rate toward the center (C) portion of the flowstream can have a value of about 500 (1/s) or lower and the higher strain rate toward the periphery (P) of the flowstream can have a value of about 3000 (1/s) or higher. As depicted in FIG. 8, according to some embodiments, the lower strain rate toward the center (C) portion of the flowstream can have a value of about 1000 (1/s) or lower and the higher strain rate toward the periphery (P) of the flowstream can have a value of about 9000 (1/s) or higher.

Hence, it can be seen that lower sample and sheath fluid rates (e.g. FIG. 7) correspond to lower strain rates, and higher sample and sheath fluid rates (e.g. FIG. 8) correspond to higher strain rates. It is understood that embodiments of the present invention encompass the use of sample and/or sheath fluids corresponding to various viscosity values, various strain rate values, and/or various shear stress values.

Autofocus Target

With returning reference to FIG. 1, particle imaging systems can include an autofocus pattern or target 44 that is fixed relative to the flowcell 22. The autofocus target 44 can be used to achieve focused images of blood fluid particles that flow through the flowcell.

Figure 9A:
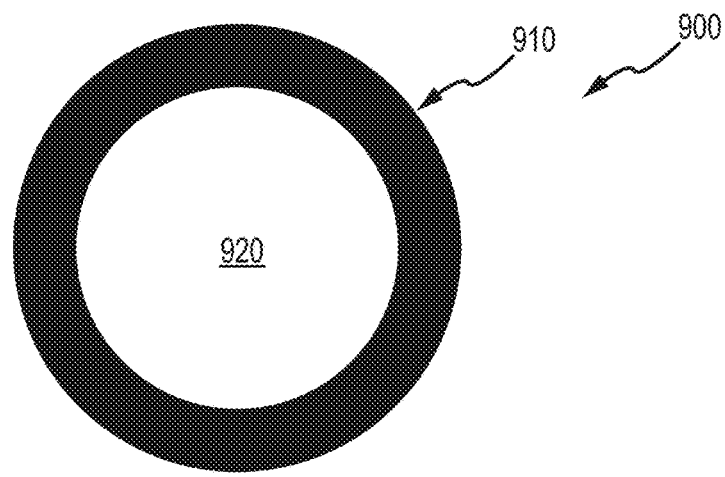
FIGS. 9A and 9B depict aspects of autofocus targets according to embodiments of the present invention.
Figure 9B:
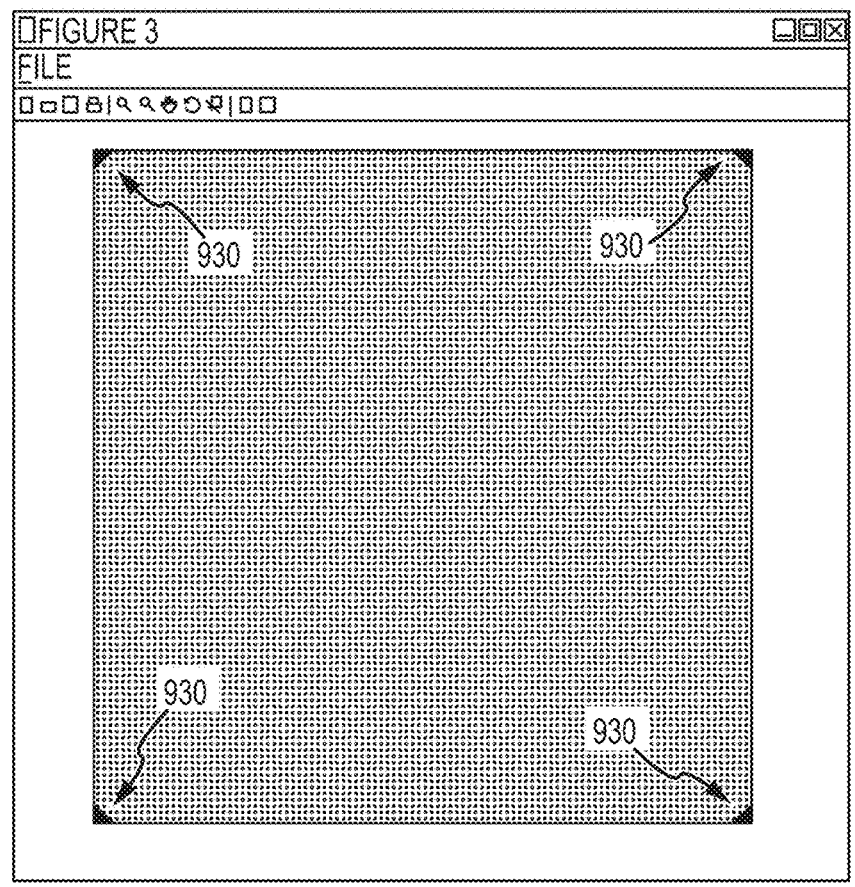

FIG. 9A depicts an exemplary autofocus target 900 according to embodiments of the present invention. As shown here, the target 900 includes an opaque annular band 910 and a transparent center or aperture 920. In operation, the imaging device focuses on the band 910, and captures the image through the aperture. As discussed elsewhere herein, and in co-pending U.S. patent application Ser. No. 14/618,811, filed Mar. 17, 2014, an image capture process can involve first focusing (or auto-focusing) on the band 910, and then adjusting a distance between the image capture device and the sample fluid stream prior to obtaining the image through the aperture 920. Accordingly, the band 910 can present a target upon which an auto-focus system of the image capture device can detect and focus upon, and certain portions of the target (e.g. edges or segments) can be included in the image. In some cases, the target can be provided as a chrome disc having a central aperture. An exemplary target can be provided with a central pinhole, having a diameter of about 0.5 mm, that is glued or fixed to the flowcell. The size of the central pinhole or aperture 920 can be selected so that only four edge portions 930 of the opaque annular band 910 are visible in the captured image 940, as illustrated in FIG. 9B. Hence, the annular band 910 does not interfere with the capturing of cell images (e.g. light can pass through the aperture 920 so as to illuminate the sample particles, and the field of view is substantially unimpeded by the annular band). In this way, the band 910 shows up only in the corners of the image.

Figure 11:
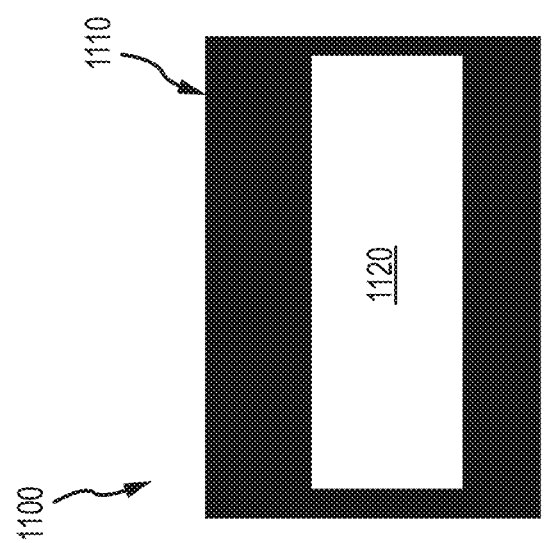
FIGS. 10 and 11 depict aspects of autofocus targets according to embodiments of the present invention.
Figure 10:
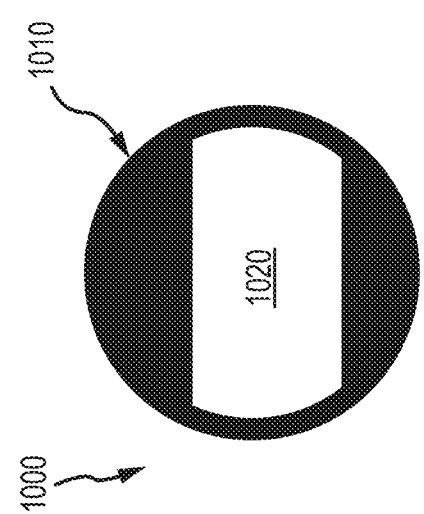

FIG. 10 depicts an exemplary autofocus target 1000 according to embodiments of the present invention. The target 1000 includes a band or border 1010 and a central aperture 1020. FIG. 11 shows another exemplary autofocus target 1100 according to embodiments of the present invention. The target 1100 includes a band or border 1110 and a central aperture 1120. According to some embodiments, the autofocus target 1100 provides an image having 50 pixels of black on the top and the bottom. In some cases, the autofocus target 1100 provides a flowcell focus offset (FCFO) of about 65.3 μm. Aspects of the FCFO are further discussed in co-pending U.S. patent application Ser. No. 14/217,228, filed Mar. 17, 2014, the content of which is incorporated herein by reference.

Figure 12A:
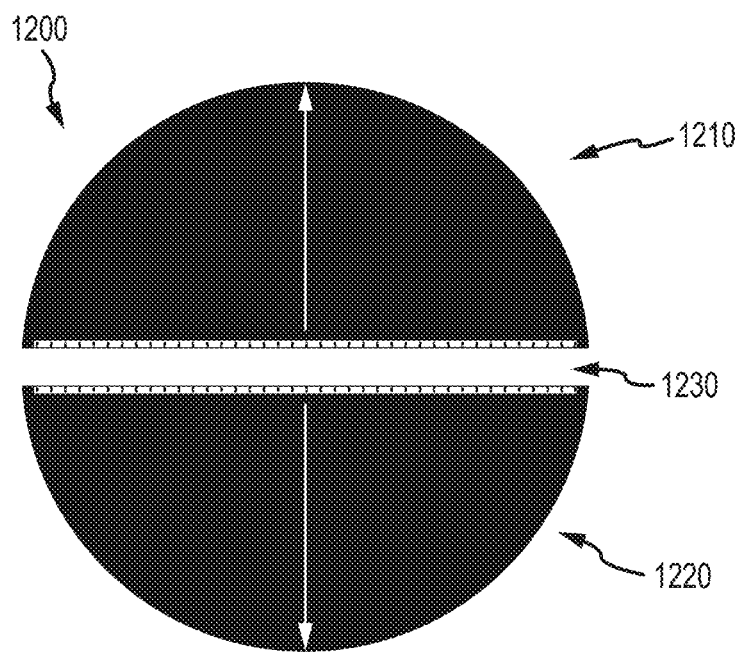
FIGS. 12A and 12B depict aspects of autofocus targets according to embodiments of the present invention.

FIG. 12A depicts an exemplary autofocus target 1200 according to embodiments of the present invention. The target 1200 is presented as a letterbox design, and includes a first or upper border 1210 and a second or lower border 1220. The target 1200 also includes an aperture or transparent passage 1230 between the first and second borders. According to some embodiments, the target has a diameter of about 4 mm, and the height of the letterbox is 265 μm. In some cases, the upper and lower borders can be present as half circles, and can be produced with a deposited metal such as chromium oxide or some other opaque material.

Figure 12B:
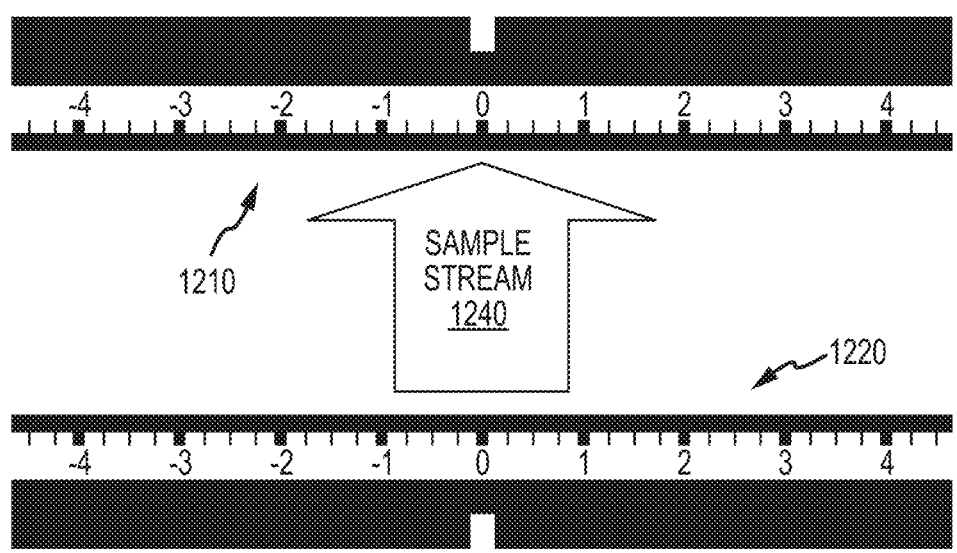

FIG. 12B shows a close-up view of the central portion of the autofocus target 1200. As shown here, the first border 1210 includes a negative/positive numerical scale, with a centered zero value. The second border 1220 includes a similar scale. In some cases, the scale increments are 100 μm. According to some embodiments, the scales can be used to facilitate positioning of the flow cell so that the field of view of the imaging device or camera can be centered on the sample stream. As shown here, the sample stream 1240 flows in a direction perpendicular to the scales of the first and second borders. As part of a focusing protocol, the image capture device can operate to focus on the numbers or other characters or imageable objects present on the borders 1210, 1220.

Figure 13A:
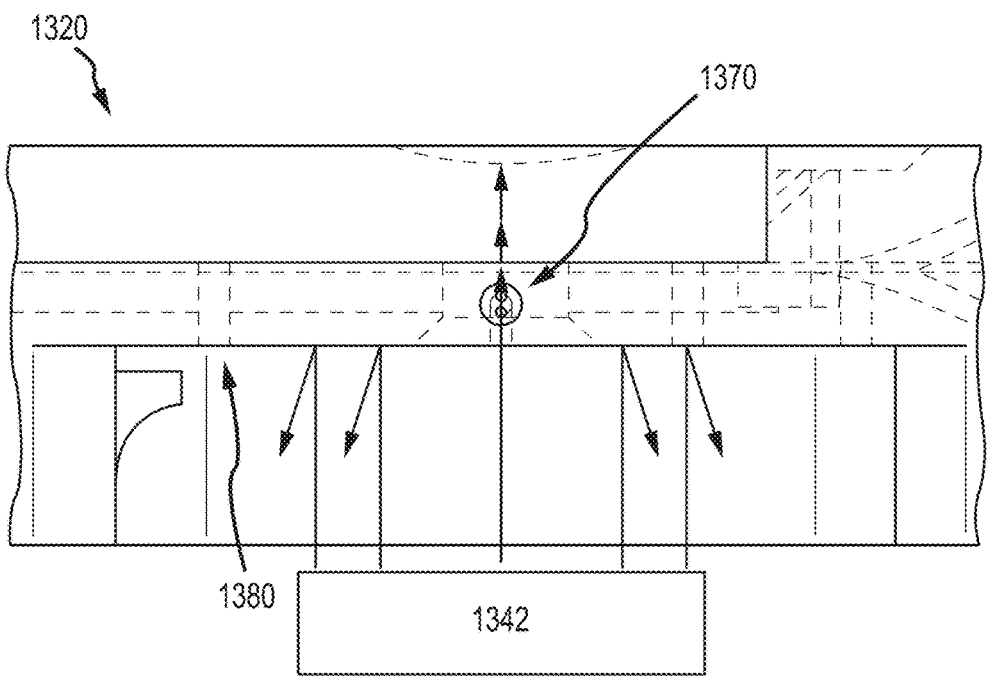
Figure 13B:
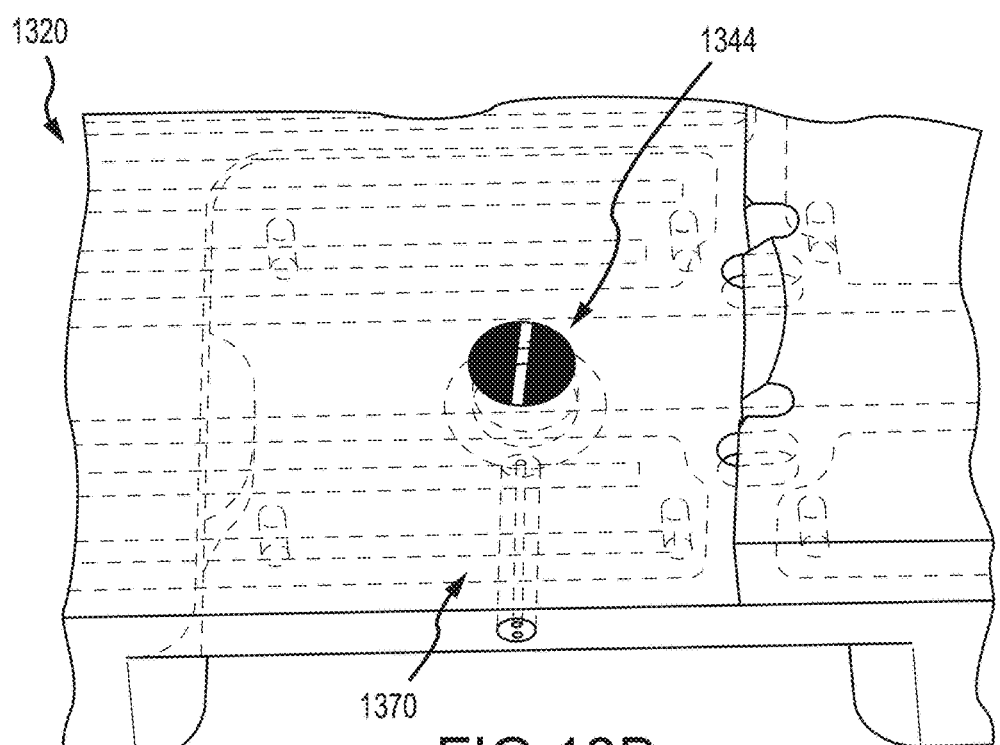

Embodiments of the present invention encompass techniques for addressing thermal drift associated with use of the particle analysis system, whereby such thermal effects may otherwise compromise the quality of images obtained with the imaging device. FIG. 13A depicts a partial side view of a flowcell 1320 having a thermal sensor 1370, a reflector 1380, and an autofocus target 1344. During operation of a particle analysis system, thermal effects may cause the sample stream to slowly drift out of focus of the imaging device. For example, thermal effects can be caused by thermal expansion of the flow cell through radiated heat coming from the lamp. Further, thermal effects can be caused by thermal expansion of the flowcell and optical bench assembly (OBA) assembly through conductive and radiative heating. In some embodiments, certain components of the OBA can expand, which may contribute to focusing errors. For example, such components may include metal plates that hold camera 24 together, a metal plate that holds or is connected to the flow cell, or a metal plate that holds both the flowcell and camera 24 together. FIG. 13B depicts a partial perspective view of flowcell 1320 having thermal sensor 1370 and autofocus target 1344. Further, FIG. 13C depicts another perspective view of flowcell 1320 having a thermal sensor 1370, reflector 1380, and autofocus target 1344.

Reflector 1380 can operate to reduce or limit the amount of heat absorbed by flowcell 1320. For example, reflector 1380 can block heat radiated by a flash lamp 1342 as indicated in FIG. 13A. Hence, reflector 1380 can minimize the thermal impact of the lamp. Reflector 1342 can also reduce glare and light scatter generated by the lamp, thus resulting in improved image quality. Thermal sensor 1370 is positioned near the fluid flow channel and adjacent to the image capture site, so that accurate temperature readings can be obtained. Information from the temperature sensor can be used to focus the image capture device on the sample fluid ribbon stream.

Figure 13D:
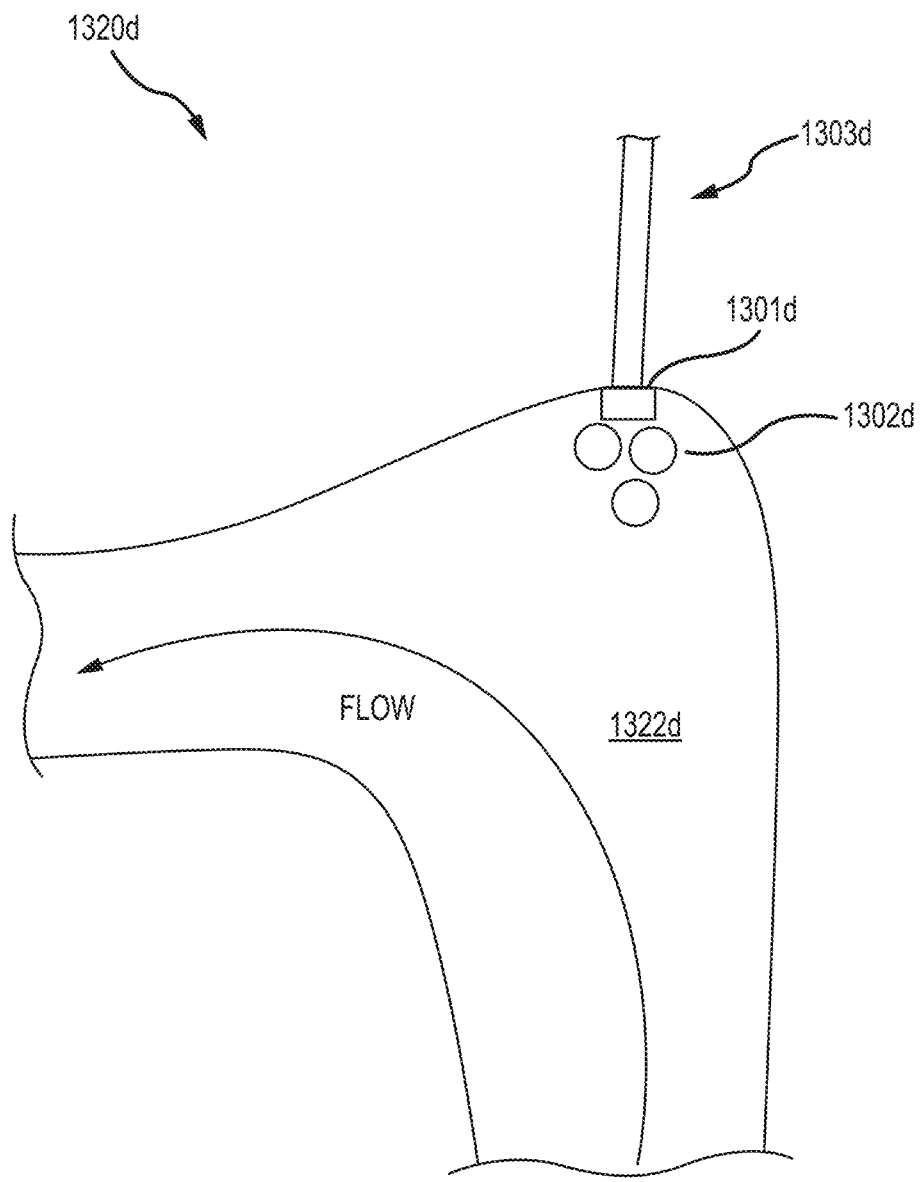
FIG. 13D depicts aspects of flowcell bubble removal techniques according to embodiments of the present invention.

As depicted in FIG. 13D, a flowcell 1300$d$ can include a flowpath 1322$d$ having a port or vent 1301$d$ through which bubbles 1302$d$ may be released or removed. As depicted here, a tube 1303$d$, through which vacuum can be applied, can be contacted with the port 1301$d$ so as to withdraw bubbles 1302$d$ from the flowstream. Such a bubble removal mechanism is suitable for removing bubbles from the flowing fluid within the flowcell, and can operate to prevent bubbles or microbubbles from becoming lodged or stuck inside of the flowcell.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

All patents, patent publications, patent applications, journal articles, books, technical references, and the like discussed in the instant disclosure are incorporated herein by reference in their entirety for all purposes.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention. Accordingly, the present invention is not limited to the embodiments described above or depicted in the drawings, and various embodiments and modifications can be made without departing from the scope of the claims below.

What is claimed is:

1. A method for imaging particles using a particle analysis system configured for combined viscosity and geometric hydrofocusing, the particles included within a body fluid sample, the method comprising:

injecting a sheath fluid along a flowpath of a flowcell of a particle analyzer, the sheath fluid having a viscosity that is different from a viscosity of the body fluid sample;

injecting the body fluid sample from a sample fluid injection tube at a flow rate into the flowing sheath fluid within the flowcell so as to provide a sample fluid stream having a first thickness adjacent the injection tube, the flowpath of the flowcell having a decrease in flowpath size such that thickness of the sample fluid stream decreases from an initial thickness to a second thickness adjacent an image capture site;

imaging a first plurality of the particles from the sample fluid stream at the image capture site of the flowcell; and limiting cell imaging orientation misalignment in the body fluid sample to less than about 20% using symmetry in the decrease in flowpath size;

wherein the decrease in flowpath size is defined by a proximal flowpath portion having a proximal thickness, and distal flowpath portion having a distal thickness less than the proximal thickness, wherein a downstream end of the sample fluid injection tube is positioned distal to the proximal flowpath portion, wherein the body fluid sample comprises serum, bone marrow aspirate, lavage fluid, effusions, exudates, cerebrospinal fluid, pleural fluid, peritoneal fluid, amniotic fluid, saliva, a seminal fluid, tears, sweat, milk, a cell suspension produced from a biopsy sample or a fecal sample, or a cell culture sample.

2. The method of claim 1, wherein:

the sheath fluid has a flow rate of about 35 µL/s, the body fluid sample has a flow rate of about 0.5 µL/s, and the method further comprising:

delivering viable cells in the body fluid sample from the sample fluid injection tube to the image capture site in a nonzero transit time that is four seconds or less, wherein viable cells have structure and internal content of the cells intact when the viable cells extend from the sample fluid stream into the flowing sheath fluid as the viable cells travel from the sample fluid injection tube to the image capture site.

3. The method of claim 1, wherein:
the body fluid sample has a velocity of between about 20 and 200 mm/second at the image capture site, and
the method further comprising:
delivering viable cells in the body fluid sample from the sample fluid injection tube to the image capture site in a nonzero transit time that is four seconds or less, wherein viable cells have structure and internal content of the cells intact when the viable cells extend from the sample fluid stream into the flowing sheath fluid as the viable cells travel from the sample fluid injection tube to the image capture site.

4. The method of claim 1, wherein:
the second thickness of the sample fluid stream is within a range from about 2 µm to about 4 µm, and
the method further comprising:
delivering viable cells in the body fluid sample from the sample fluid injection tube to the image capture site in a nonzero transit time that is four seconds or less, wherein viable cells have structure and internal content of the cells intact when the viable cells extend from the sample fluid stream into the flowing sheath fluid as the viable cells travel from the sample fluid injection tube to the image capture site.

5. The method of claim 1, wherein:
a ratio of the proximal thickness of the proximal flowpath portion to the distal thickness of the distal flowpath portion has a geometric thinning value selected form the group consisting of 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 125:1, 130:1, 140:1, 150:1, 160:1, 170:1, 180:1, 190:1, and 200:1, and
the method further comprising delivering viable cells in the body fluid sample from the sample fluid injection tube to the image capture site in a nonzero transit time that is four seconds or less, wherein viable cells have structure and internal content of the cells intact when the viable cells extend from the sample fluid stream into the flowing sheath fluid as the viable cells travel from the sample fluid injection tube to the image capture site.

6. The method of claim 1, further comprising:
delivering viable cells in the body fluid sample from the sample fluid injection tube to the image capture site in a nonzero transit time that is four seconds or less.

7. The method of claim 1, further comprising extending cells from the sample fluid stream into the flowing sheath fluid as the viable cells travel from the sample fluid injection tube to the image capture site.

8. The method of claim 1, wherein:
injecting the sheath fluid the sheath fluid along the flowpath comprises injecting the sheath fluid at a sheath fluid flow rate,
the sheath fluid flow rate and a flow area cross-section of the flowcell correspond to a sheath fluid velocity,
the flow rate of the body fluid sample and a flow area cross section of an exit port of the injection tube correspond to a body fluid sample velocity, and
there is a velocity difference between the sheath fluid velocity and the body fluid sample velocity.

9. The method of claim 8, the method further comprising hydrofocusing cells in the body fluid sample at the image capture site.

10. The method of claim 1, wherein the body fluid sample comprises spherical particles, and
the method further comprising:
aligning intracellular organelles of the spherical particles within a focal plane at the image capture site of the flowcell.

11. The method of claim 1, wherein the injection tube comprises a proximal portion having a first flow cross-section area and a distal portion having a second flow cross-section area, and wherein the first flow cross-section area of the proximal portion is greater than 1.5 times the second flow cross-section area of the distal portion.

12. The method of claim 1, wherein a ratio of sheath fluid flow rate to sample fluid flow rate is about 200.

13. The method of claim 1, wherein the second thickness of the sample fluid stream is within a range from about 2 µm to about 10 µm.

14. The method of claim 1, wherein a ratio of the first thickness of the sample fluid stream to the second thickness of the sample fluid stream has a value within a range from about 20:1 to about 70:1.

15. The method of claim 1, wherein:
imaging the first plurality of the particles comprises capturing an image with a high optical resolution imaging device.

16. The method of claim 1, wherein:
imaging the first plurality of the particles comprises capturing an image with a high optical resolution imaging device with an optical resolution of 1 µm or lower.

17. The method of claim 1, wherein:
imaging the first plurality of the particles comprises capturing an image with a digital image capture device.

18. The method of claim 1, wherein:
imaging the first plurality of the particles generates images comprising in-focus cellular contents of the first plurality of the particles.

* * * * *

UNITED STATES PATENT AND TRADEMARK OFFICE
CERTIFICATE OF CORRECTION

PATENT NO. : 10,345,217 B2
APPLICATION NO. : 15/880328
DATED : July 9, 2019
INVENTOR(S) : Wanders et al.

Page 1 of 1

It is certified that error appears in the above-identified patent and that said Letters Patent is hereby corrected as shown below:

In the Claims

In Column 41, Line 31, in Claim 5, delete "form" and insert --from-- therefor

Signed and Sealed this
Second Day of June, 2020

Andrei Iancu
*Director of the United States Patent and Trademark Office*